(12) United States Patent
Wang et al.

(10) Patent No.: US 7,888,464 B2
(45) Date of Patent: Feb. 15, 2011

(54) HEPATITIS C VIRUS INHIBITORS

(75) Inventors: Alan Xiangdong Wang, Guilford, CT (US); Barbara Zhizhen Zheng, Cheshire, CT (US); Stanley D'Andrea, Wallingford, CT (US); Qian Zhao, Wallingford, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 723 days.

(21) Appl. No.: 11/939,780

(22) Filed: Nov. 14, 2007

(65) Prior Publication Data
US 2009/0274648 A1 Nov. 5, 2009

Related U.S. Application Data

(60) Provisional application No. 60/866,130, filed on Nov. 16, 2006.

(51) Int. Cl.
*A61K 38/06* (2006.01)
(52) U.S. Cl. .................................................. 530/331
(58) Field of Classification Search ........................ None
See application file for complete search history.

(56) References Cited

U.S. PATENT DOCUMENTS

| 5,223,432 | A | 6/1993 | Wirz et al. |
|---|---|---|---|
| 2005/0153877 | A1 | 7/2005 | Miao et al. |
| 2006/0172950 | A1 | 8/2006 | Wang et al. |
| 2006/0199773 | A1 | 9/2006 | Sausker et al. |
| 2006/0257980 | A1 | 11/2006 | Li |
| 2007/0078081 | A1 | 4/2007 | Casarez et al. |
| 2008/0032936 | A1 | 2/2008 | Gai et al. |
| 2008/0039375 | A1 | 2/2008 | Moore et al. |
| 2008/0039470 | A1 | 2/2008 | Niu et al. |

FOREIGN PATENT DOCUMENTS

| WO | WO 98/17679 | 4/1998 |
|---|---|---|
| WO | WO 99/07733 | 2/1999 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 02/008244 | 1/2002 |
| WO | WO 02/060926 | 8/2002 |
| WO | WO 03/053349 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/066103 | 8/2003 |
| WO | WO 03/099274 | 12/2003 |
| WO | WO 03/099316 | 12/2003 |
| WO | WO 2004/009121 | 1/2004 |
| WO | WO 2004/032827 | 4/2004 |
| WO | WO 2004/037855 | 5/2004 |
| WO | WO 2004/043339 | 5/2004 |
| WO | WO 2004/072243 | 8/2004 |
| WO | WO 2004/093798 | 11/2004 |
| WO | WO 2004/093915 | 11/2004 |
| WO | WO 2004/094452 | 11/2004 |
| WO | WO 2004/101602 | 11/2004 |
| WO | WO 2004/101605 | 11/2004 |
| WO | WO 2004/103996 | 12/2004 |
| WO | WO 2004/113365 | 12/2004 |
| WO | WO 2005/010029 | 2/2005 |
| WO | WO 2005/028501 | 3/2005 |
| WO | WO 2005/037214 | 4/2005 |
| WO | WO 2005/037860 | 4/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/070955 | 8/2005 |
| WO | WO 2005/073216 | 8/2005 |
| WO | WO 2005/095403 | 10/2005 |
| WO | WO 2005/116054 | 12/2005 |
| WO | WO 2006/000085 | 1/2006 |
| WO | WO 2006/007700 | 1/2006 |
| WO | WO 2006/007708 | 1/2006 |
| WO | WO 2006/016930 | 2/2006 |
| WO | WO 2006/020276 | 2/2006 |
| WO | WO 2006/026352 | 3/2006 |
| WO | WO 2006/033878 | 3/2006 |
| WO | WO 2006/043145 | 4/2006 |
| WO | WO 2006/086381 | 8/2006 |
| WO | WO 2006/096652 | 9/2006 |

(Continued)

OTHER PUBLICATIONS

U.S. Appl. No. 11/923,918, filed Oct. 25, 2007, D'Andrea et al.

(Continued)

*Primary Examiner*—Cecilia Tsang
*Assistant Examiner*—Thomas S Heard
(74) *Attorney, Agent, or Firm*—Pamela A. Mingo

(57) ABSTRACT

Hepatitis C virus inhibitors having the general formula

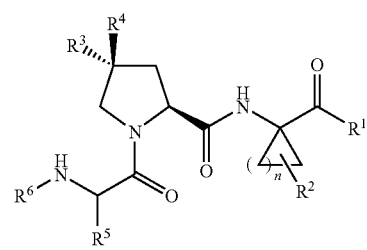

are disclosed. Compositions comprising the compounds and methods for using the compounds to inhibit HCV are also disclosed.

18 Claims, No Drawings

FOREIGN PATENT DOCUMENTS

| | | |
|---|---|---|
| WO | WO 2006/119061 | 11/2006 |
| WO | WO 2006/122188 | 11/2006 |
| WO | WO 2006122188 * | 11/2006 |
| WO | WO 2006/130552 | 12/2006 |
| WO | WO 2006/130553 | 12/2006 |
| WO | WO 2006/130554 | 12/2006 |
| WO | WO 2006/130607 | 12/2006 |
| WO | WO 2006/130626 | 12/2006 |
| WO | WO 2006/130627 | 12/2006 |
| WO | WO 2006/130628 | 12/2006 |
| WO | WO 2006/130666 | 12/2006 |
| WO | WO 2006/130686 | 12/2006 |
| WO | WO 2006/130687 | 12/2006 |
| WO | WO 2006/130688 | 12/2006 |
| WO | WO 2007/001406 | 1/2007 |
| WO | WO 2007/008657 | 1/2007 |
| WO | WO 2007/009109 | 1/2007 |
| WO | WO 2007/009227 | 1/2007 |
| WO | WO 2007/014918 | 2/2007 |
| WO | WO 2007/014919 | 2/2007 |
| WO | WO 2007/014920 | 2/2007 |
| WO | WO 2007/014921 | 2/2007 |
| WO | WO 2007/014922 | 2/2007 |
| WO | WO 2007/014923 | 2/2007 |
| WO | WO 2007/014924 | 2/2007 |
| WO | WO 2007/014925 | 2/2007 |
| WO | WO 2007/014926 | 2/2007 |
| WO | WO 2007/014927 | 2/2007 |
| WO | WO 2007/015787 | 2/2007 |
| WO | WO 2007/015824 | 2/2007 |
| WO | WO 2007/015855 | 2/2007 |
| WO | WO 2007/016441 | 2/2007 |
| WO | WO 2007/016476 | 2/2007 |
| WO | WO 2007/017144 | 2/2007 |
| WO | WO 2007/025307 | 3/2007 |
| WO | WO 2007/044893 | 4/2007 |
| WO | WO 2007/044933 | 4/2007 |
| WO | WO 2007/056120 | 5/2007 |
| WO | WO 2007/082131 | 7/2007 |
| WO | WO 2007/106317 | 9/2007 |
| WO | WO 2007/131966 | 11/2007 |
| WO | WO 2007/143694 | 12/2007 |
| WO | WO 2007/148135 | 12/2007 |
| WO | WO 2008/002924 | 1/2008 |
| WO | WO 2008/005511 | 1/2008 |
| WO | WO 2008/008502 | 1/2008 |
| WO | WO 2008/008776 | 1/2008 |
| WO | WO 2008/019266 | 2/2008 |
| WO | WO 2008/019289 | 2/2008 |
| WO | WO 2008/019303 | 2/2008 |
| WO | WO 2008/021733 | 2/2008 |
| WO | WO 2008/021871 | 2/2008 |
| WO | WO 2008/021956 | 2/2008 |
| WO | WO 2008/021960 | 2/2008 |
| WO | WO 2008/022006 | 2/2008 |

OTHER PUBLICATIONS

U.S. Appl. No. 11/923,948, filed Oct. 25, 2007, D'Andrea et al.
U.S. Appl. No. 11/923,977, filed Oct. 25, 2007, D'Andrea et al.
U.S. Appl. No. 11/934,840, filed Nov. 5, 2007, Sin et al.
U.S. Appl. No. 11/939,753, filed Oct. 14, 2007, Wang et al.
U.S. Appl. No. 11/939,768, filed Nov. 14, 2007, Wang et al.
Lauer G. M. et al., "Hepatitis C Virus Infection," New England Journal of Medicine, vol. 345 No. 1, pp. 41-52, (2001).
Poupart, M.-A. et al., "Solid-Phase Synthesis of Peptidomimetic Inhibitors for the Hepatitis C Virus NS3 Protease," The Journal of Organic Chemistry, vol. 66 No. 14, pp. 4743-4751, (2001).
Llinas-Brunet et al. (2004) Journal of Medicinal Chemistry, vol. 47 pp. 6584-6594.

* cited by examiner

HEPATITIS C VIRUS INHIBITORS

CROSS-REFERENCE TO RELATED APPLICATIONS

This application claims the benefit of U.S. Provisional Application Ser. No. 60/866,130 filed Nov. 16, 2006.

The present disclosure is generally directed to antiviral compounds, and more specifically directed to compounds which inhibit the function of the NS3 protease (also referred to herein as "serine protease") encoded by Hepatitis C virus (HCV), compositions comprising such compounds, and methods for inhibiting the function of the NS3 protease.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and unmet need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. Six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one cleaves at the NS2-NS3 junction; the second one is a serine protease contained within the N-terminal region of NS3 and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a co-factor for the NS3 protease and possibly assisting in the membrane localization of NS3 and other viral replicase components. The complex formation of the NS3 protein with NS4A is essential for efficient polyprotein processing, enhancing the proteolytic cleavage at all of the sites. The NS3 protein also exhibits nucleoside triphosphatase and RNA helicase activities. NS5B is a RNA-dependent RNA polymerase that is involved in the replication of HCV.

The present disclosure provides peptide compounds that can inhibit the functioning of the NS3 protease, e.g., in combination with the NS4A protease. Further, the present disclosure describes the administration of combination therapy to a patient whereby a compound in accordance with the present disclosure, which is effective to inhibit the HCV NS3 protease, can be administered with one or two additional compounds having anti-HCV activity.

In a first aspect the present disclosure provides a compound of formula (I)

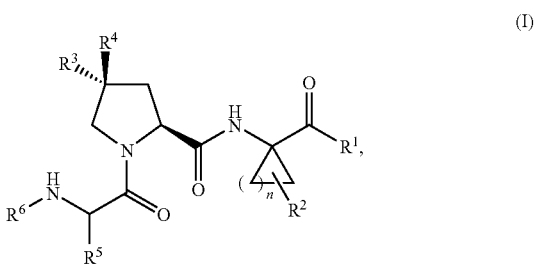

(I)

or a pharmaceutically acceptable salt thereof, wherein n is 1, 2, or 3;

$R^1$ is selected from hydroxy and —NHSO$_2$R$^7$;

$R^2$ is selected from hydrogen, alkenyl, alkyl, cyanoalkyl, cycloalkyl, and haloalkyl;

$R^3$ is selected from alkenyl, alkyl, aryl, arylalkyl, cycloalkyl, (cycloalkyl)alkyl, heterocyclyl, and heterocyclylalkyl;

$R^4$ is —OR$^8$;

$R^5$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, hydroxyalkyl, (NR$^a$R$^b$)alkyl, and (NR$^a$R$^b$)carbonylalkyl;

$R^6$ is selected from alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, (NR$^a$R$^b$)carbonyl, and (NR$^a$R$^b$)sulfonyl; or $R^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —NR$^g$R$^h$, (NR$^j$R$^k$)carbonyl, (NR$^j$R$^k$)sulfonyl, and oxo;

$R^7$ is selected from alkyl, aryl, cycloalkyl, (cycloalkyl)alkyl, heterocyclyl, and —NR$^c$R$^d$;

$R^8$ is selected from alkoxyalkyl, alkyl, alkylcarbonyl, arylalkyl, cycloalkyl, (cycloalkyl)alkyl, cycloalkylcarbonyl, haloalkoxyalkyl, haloalkyl, (NR$^e$R$^f$)carbonyl, and —P(O)(OR')$_2$; wherein R$^e$ and R$^f$ are independently selected from hydrogen, alkyl, and arylalkyl; or R$^e$ and R$^f$, together with the nitrogen atom to which they are attached, form a five or six-membered monocyclic heterocyclic ring optionally containing one additional heteroatom selected from O, NR$^x$, and S; wherein R$^x$ is selected from hydrogen and alkyl; and wherein R' is selected from hydrogen and alkyl;

$R^a$ and $R^b$ are independently selected from hydrogen, alkoxy, alkoxyalkyl, alkyl, aryl, arylalkyl, cycloalkyl, haloalkoxyalkyl, haloalkyl, heterocyclyl, and heterocyclylalkyl;

$R^c$ and $R^d$ are independently selected from alkoxy, alkyl, aryl, arylalkyl, cycloalkyl, (cycloalkyl)alkyl, heterocyclyl, and heterocyclylalkyl; or $R^c$ and $R^d$ together with the nitrogen atom to which they are attached form a five or six-membered monocyclic heterocyclic ring;

$R^g$ and $R^h$ are independently selected from hydrogen, alkoxyalkyl, alkoxycarbonyl, alkyl, alkylcarbonyl, arylalkyl, and haloalkyl; and $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a second aspect the present disclosure provides a compound of formula (II)

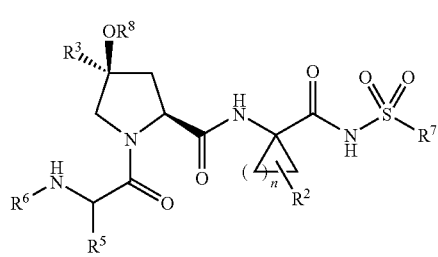

(II)

or a pharmaceutically acceptable salt thereof, wherein n is 1, 2, or 3;

$R^2$ is selected from hydrogen, alkenyl, alkyl, cyanoalkyl, cycloalkyl, and haloalkyl;

$R^3$ is selected from alkenyl, alkyl, aryl, arylalkyl, cycloalkyl, (cycloalkyl)alkyl, heterocyclyl, and heterocyclylalkyl;

$R^5$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, hydroxyalkyl, $(NR^aR^b)$alkyl, and $(NR^aR^b)$carbonylalkyl;

$R^6$ is selected from alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, $(NR^aR^b)$carbonyl, and $(NR^aR^b)$sulfonyl; or $R^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —$NR^gR^h$, $(NR^jR^k)$carbonyl, $(NR^jR^k)$sulfonyl, and oxo;

$R^7$ is selected from alkyl, aryl, cycloalkyl, (cycloalkyl)alkyl, heterocyclyl, and —$NR^cR^d$;

$R^8$ is selected from alkoxyalkyl, alkyl, alkylcarbonyl, arylalkyl, cycloalkyl, (cycloalkyl)alkyl, cycloalkylcarbonyl, haloalkoxyalkyl, haloalkyl, $(NR^eR^f)$carbonyl, and —$P(O)(OR')_2$; wherein $R^e$ and $R^f$ are independently selected from hydrogen, alkyl, and arylalkyl; or $R^e$ and $R^f$, together with the nitrogen atom to which they are attached, form a five or six-membered monocyclic heterocyclic ring optionally containing one additional heteroatom selected from O, $NR^x$, and S; wherein $R^x$ is selected from hydrogen and alkyl; and wherein R' is selected from hydrogen and alkyl;

$R^a$ and $R^b$ are independently selected from hydrogen, alkoxy, alkoxyalkyl, alkyl, aryl, arylalkyl, cycloalkyl, haloalkoxyalkyl, haloalkyl, heterocyclyl, and heterocyclylalkyl;

$R^c$ and $R^d$ are independently selected from alkoxy, alkyl, aryl, arylalkyl, cycloalkyl, (cycloalkyl)alkyl, heterocyclyl, and heterocyclylalkyl; or $R^c$ and $R^d$ together with the nitrogen atom to which they are attached form a five or six-membered monocyclic heterocyclic ring;

$R^g$ and $R^h$ are independently selected from hydrogen, alkoxyalkyl, alkoxycarbonyl, alkyl, alkylcarbonyl, arylalkyl, and haloalkyl; and $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

In a first embodiment of the second aspect the present disclosure provides a compound of formula (II), or a pharmaceutically acceptable salt thereof, wherein n is 1;

$R^2$ is selected from alkenyl, alkyl, and haloalkyl;

$R^3$ is selected from alkenyl, alkyl, aryl, arylalkyl, cycloalkyl, (cycloalkyl)alkyl, heterocyclyl, and heterocyclylalkyl;

$R^5$ is selected from alkenyl, alkyl, and arylalkyl;

$R^6$ is selected from alkoxycarbonyl, cycloalkyloxycarbonyl, haloalkoxycarbonyl, $(NR^aR^b)$carbonyl; or $R^6$ is phenyl optionally substituted with one or two substitutents independently selected from alkoxy and halo; and $R^7$ is cycloalkyl.

In a second embodiment of the second aspect the present disclosure provides a compound of formula (II), or a pharmaceutically acceptable salt thereof, wherein n is 1;

$R^2$ is selected from alkenyl, alkyl, and haloalkyl;

$R^3$ is selected from aryl and heterocyclyl;

$R^5$ is selected from alkenyl, alkyl, and arylalkyl;

$R^6$ is selected from alkoxycarbonyl, cycloalkyloxycarbonyl, haloalkoxycarbonyl, $(NR^aR^b)$carbonyl; or $R^6$ is phenyl optionally substituted with one or two substitutents independently selected from alkoxy and halo; and $R^7$ is cycloalkyl.

In a third embodiment of the second aspect the present disclosure provides a compound of formula (II), or a pharmaceutically acceptable salt thereof, wherein n is 1;

$R^2$ is selected from alkenyl, alkyl, and haloalkyl;

$R^3$ is aryl;

$R^5$ is selected from alkenyl, alkyl, and arylalkyl;

$R^6$ is selected from alkoxycarbonyl, cycloalkyloxycarbonyl, haloalkoxycarbonyl, $(NR^aR^b)$carbonyl; or $R^6$ is phenyl optionally substituted with one or two substitutents independently selected from alkoxy and halo; and $R^7$ is cycloalkyl.

In a third aspect the present disclosure provides a composition comprising the compound of formula (I), or a pharmaceutically acceptable salt thereof, and a pharmaceutically acceptable carrier. In a first embodiment of the third aspect the composition further comprises at least one additional compound having anti-HCV activity. In a second embodiment of the third aspect at least one of the additional compounds is an interferon or a ribavirin. In a third embodiment of the third aspect the interferon is selected from interferon alpha 2B, pegylated interferon alpha, consensus interferon, interferon alpha 2A, and lymphoblastiod interferon tau.

In a fourth embodiment of the third aspect the present disclosure provides a composition comprising the compound of formula (I), or a pharmaceutically acceptable salt thereof, a pharmaceutically acceptable carrier, and at least one additional compound having anti-HCV activity, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the third aspect the present disclosure provides a composition comprising the compound of formula (I), or a pharmaceutically acceptable salt thereof, a pharmaceutically acceptable carrier, and at least one additional compound having anti-HCV activity, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fourth aspect the present disclosure provides a method of treating an HCV infection in a patient, comprising administering to the patient a therapeutically effective amount of a compound of formula (I), or a pharmaceutically acceptable salt thereof. In a first embodiment of the fourth aspect the method further comprises administering at least one additional compound having anti-HCV activity prior to, after, or simultaneously with the compound of formula (I), or a pharmaceutically acceptable salt thereof. In a second embodiment of the fourth aspect at least one of the additional compounds is an interferon or a ribavirin. In a third embodiment of the fourth aspect the interferon is selected from interferon alpha 2B, pegylated interferon alpha, consensus interferon, interferon alpha 2A, and lymphoblastiod interferon tau.

In a fourth embodiment of the fourth aspect the present disclosure provides a method of treating an HCV infection in a patient, comprising administering to the patient a therapeutically effective amount of a compound of formula (I), or a pharmaceutically acceptable salt thereof and at least one additional compound having anti-HCV activity prior to, after, or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the fourth aspect the present disclosure provides a method of treating an HCV infection in a patient, comprising administering to the patient a therapeutically effective amount of a compound of formula (I), or a pharmaceutically acceptable salt thereof and at least one additional compound having anti-HCV activity prior to, after, or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In a fifth aspect the present disclosure provides a composition comprising a compound of formula (I), or a pharmaceutically acceptable salt thereof, one, two, three, four, or five additional compounds having anti-HCV activity, and a pharmaceutically acceptable carrier. In a first embodiment of the fifth aspect the composition comprises three or four additional compounds having anti-HCV activity. In a second embodiment of the fifth aspect the composition comprises one or two additional compounds having anti-HCV activity.

In a sixth aspect the present disclosure provides a method of treating an HCV infection in a patient, comprising administering to the patient a therapeutically effective amount of a compound of formula (I), or a pharmaceutically acceptable salt thereof and one, two, three, four, or five additional compounds having anti-HCV activity prior to, after, or simultaneously with the compound of formula (I), or a pharmaceutically acceptable salt thereof. In a first embodiment of the sixth aspect the method comprises administering three or four additional compounds having anti-HCV activity. In a second embodiment of the sixth aspect the method comprises administering one or two additional compounds having anti-HCV activity.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substitutent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

The term "alkenyl," as used herein, refers to a straight or branched chain group of two to six carbon atoms containing at least one carbon-carbon double bond.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to ten carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure can be optionally substituted with one, two, three, four, or five substituents independently selected from alkoxy, alkoxycarbonyl, alkyl, a second aryl group, cyano, halo, haloalkoxy, haloalkyl, heterocyclyl, heterocyclylalkyl, hydroxy, hydroxyalkyl, nitro, —$NR^xR^y$, ($NR^xR^y$)alkoxy, ($NR^xR^y$)alkyl, ($NR^xR^y$)carbonyl, and oxo; wherein the second aryl group, the heterocyclyl, and the heterocyclyl part of the heterocyclylalkyl can be further optionally substituted with one, two, three, four, or five substituents independently selected from alkoxy, alkyl, cyano, halo, haloalkoxy, haloalkyl, hydroxy, and nitro.

The term "arylalkyl," as used herein, refers to an alkyl group substituted with one, two, or three aryl groups.

The term "carbonyl," as used herein, refers to —C(O)—.

The term "carboxy," as used herein, refers to —$CO_2H$.

The term "carboxyalkyl," as used herein, refers to an alkyl group substituted with one, two, or three carboxy groups.

The term "cyano," as used herein, refers to —CN.

The term "cyanoalkyl," as used herein, refers to an alkyl group substituted with one, two, or three cyano groups.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl. The cycloalkyl groups of the present disclosure can be optionally substituted with one, two, three, or four substituents independently selected from alkenyl, alkoxy, alkoxyalkyl, alkyl, arylalkyl, arylcarbonyl, cyano, cycloalkenyl, (cycloalkyl)alkyl, halo, haloalkoxy, haloalkyl, and ($NR^jR^k$)carbonyl; wherein $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

The term "(cycloalkyl)alkyl," as used herein, refers to an alkyl group substituted with one, two, or three cycloalkyl groups.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkoxyalkyl," as used herein, refers to an alkyl group substituted with one, two, or three haloalkoxy groups.

The term "haloalkoxycarbonyl," as used herein, refers to a haloalkoxy group attached to the parent molecular moiety through a carbonyl group.

The term "haloalkyl," as used herein, refers to an alkyl group substituted with one, two, three, or four halogen atoms.

The term "haloalkylcarbonyl," as used herein, refers to a haloalkyl group attached to the parent molecular moiety through a carbonyl group.

The term "heterocyclyl," as used herein, refers to a five-, six-, or seven-membered ring containing one, two, or three heteroatoms independently selected from nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a four- to six-membered aromatic or non-aromatic carbocyclic ring or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl. The heterocyclyl groups of the present disclosure can be optionally substituted with one, two, three, four, or five substituents independently selected from alkoxy, alkoxycarbonyl, alkyl, aryl, cyano, halo, haloalkoxy, haloalkyl, a second heterocyclyl group, heterocyclylalkyl, hydroxy, hydroxyalkyl, nitro, —$NR^xR^y$, ($NR^xR^y$)alkoxy, ($NR^xR^y$)alkyl, ($NR^xR^y$)carbonyl, and oxo; wherein the aryl, the second heterocyclyl group, and the heterocyclyl part of the heterocyclylalkyl can be further optionally substituted with one, two, three, four, or five substituents independently selected from alkoxy, alkyl, cyano, halo, haloalkoxy, haloalkyl, hydroxy, and nitro.

The term "heterocyclylalkyl," as used herein, refers to an alkyl group substituted with one, two, or three heterocyclyl groups.

The term "hydroxy," as used herein, refers to —OH.

The term "hydroxyalkyl," as used herein, refers to an alkyl group substituted with one, two, or three hydroxy groups.

The term "—$NR^aR^b$," as used herein, refers to two groups, $R^a$ and $R^b$, which are attached to the parent molecular moiety through a nitrogen atom. $R^a$ and $R^b$ are each independently selected from hydrogen, alkoxy, alkoxyalkyl, alkyl, aryl, arylalkyl, cycloalkyl, haloalkoxyalkyl, haloalkyl, heterocyclyl, and heterocyclylalkyl.

The term "($NR^aR^b$)alkyl," as used herein, refers to an alkyl group substituted with one, two, or three —$NR^aR^b$ groups.

The term "($NR^aR^b$)carbonyl," as used herein, refers to an —$NR^aR^b$ group attached to the parent molecular moiety through a carbonyl group.

The term "($NR^aR^b$)carbonylalkyl," as used herein, refers to an alkyl group substituted with one, two, or three ($NR^aR^b$) carbonyl groups.

The term "($NR^aR^b$)sulfonyl," as used herein, refers to an —$NR^aR^b$ group attached to the parent molecular moiety through a sulfonyl group.

The term "—$NR^cR^d$," as used herein, refers to two groups, $R^c$ and $R^d$, which are attached to the parent molecular moiety through a nitrogen atom. $R^c$ and $R^d$ are independently selected from alkoxy, alkyl, aryl, arylalkyl, cycloalkyl, (cycloalkyl)alkyl, heterocyclyl, and heterocyclylalkyl; or $R^c$ and $R^d$ together with the nitrogen atom to which they are attached form a five or six-membered monocyclic heterocyclic ring.

The term "—NR$^e$R$^f$," as used herein, refers to two groups, R$^e$ and R$^f$ which are attached to the parent molecular moiety through a nitrogen atom. R$^e$ and R$^f$ are independently selected from hydrogen, alkyl, and arylalkyl; or R$^e$ and R$^f$, together with the nitrogen atom to which they are attached, form a five or six-membered monocyclic heterocyclic ring optionally containing one additional heteroatom selected from O, NR$^x$, and S; wherein R$^x$ is selected from hydrogen and alkyl; and wherein R' is selected from hydrogen and alkyl.

The term "—NR$^g$R$^h$," as used herein, refers to two groups, R$^g$ and R$^h$, which are attached to the parent molecular moiety through a nitrogen atom. R$^g$ and R$^h$ are independently selected from hydrogen, alkoxyalkyl, alkoxycarbonyl, alkyl, alkylcarbonyl, arylalkyl, and haloalkyl.

The term "—NR$^j$R$^k$," as used herein, refers to two groups, R$^j$ and R$^k$, which are attached to the parent molecular moiety through a nitrogen atom. R$^j$ and R$^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

The term "(NR$^j$R$^k$)carbonyl," as used herein, refers to an —NR$^j$R$^k$ group attached to the parent molecular moiety through a carbonyl group.

The term "(NR$^j$R$^k$)sulfonyl," as used herein, refers to an —NR$^e$R$^f$ group attached to the parent molecular moiety through a sulfonyl group.

The term "—NR$^x$R$^y$," as used herein, refers to two groups, R$^x$ and R$^y$, which are attached to the parent molecular moiety through a nitrogen atom. R$^x$ and R$^y$ are independently selected from hydrogen and alkyl.

The term "(NR$^x$R$^y$)alkoxy," as used herein, refers to an (NR$^x$R$^y$)alkyl group attached to the parent molecular moiety through an oxygen atom.

The term "(NR$^x$R$^y$)alkyl," as used herein, refers to an alkyl group substituted with one, two, or three —NR$^x$R$^y$ groups.

The term (NR$^x$R$^y$)carbonyl," as used herein, refers to an —NR$^x$R$^y$ group attached to the parent molecular moiety through a carbonyl group.

The term "nitro," as used herein, refers to —NO$_2$.

The term "oxo," as used herein, refers to =O.

The term "sulfonyl," as used herein, refers to —SO$_2$—.

The compounds of the present disclosure can exist as prodrugs. The term "prodrug," as used herein, represents compounds which are rapidly transformed in vivo to the parent compounds by hydrolysis in blood. Prodrugs of the present disclosure include esters of hydroxy groups on the parent molecule, esters of carboxy groups on the parent molecule, and amides of amines on the parent molecule.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

As used herein, the term "anti-HCV activity" means the compound is effective to treat the HCV virus.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Where used in naming compounds of the present disclosure, the designations P1', P1, P2, P2*, P3, and P4, as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend toward the C-terminus. For example, P1' refers to the first position away from the right hand end of the C-terminus of the cleavage site (i.e. N-terminus first position); whereas P1 starts the numbering from the left hand side of the C-terminus cleavage site, P2: second position from the C-terminus, etc.). (see Berger A. & Schechter I., Transactions of the Royal Society London series (1970), B257, 249-264].

The following figure shows the designations for the compounds of the present disclosure.

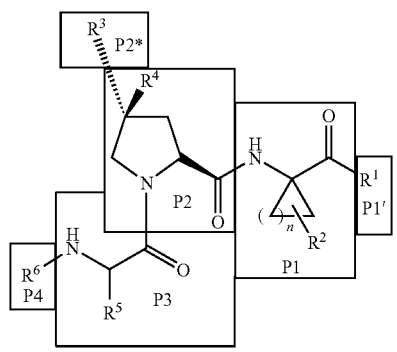

Asymmetric centers exist in the compounds of the present disclosure. For example, the compounds may include P1 cyclopropyl element of formula

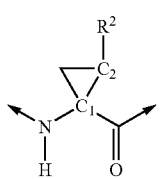

wherein $C_1$ and $C_2$ each represent an asymmetric carbon atom at positions 1 and 2 of the cyclopropyl ring.

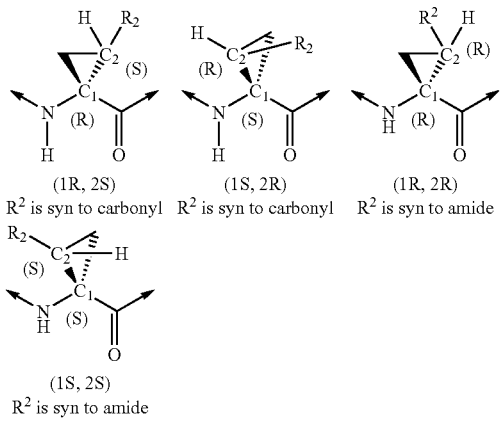

It should be understood that the disclosure encompasses all stereochemical forms, or mixtures thereof, which possess the ability to inhibit HCV protease.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
| --- | --- | --- | --- |
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/ Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |

TABLE 1-continued

| Brand Name | Physiological Class | Type of Inhibitor or Target | Source Company |
|---|---|---|---|
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |

TABLE 1-continued

| Brand Name | Physiological Class | Type of Inhibitor or Target | Source Company |
|---|---|---|---|
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |

TABLE 1-continued

| Brand Name | Physiological Class | Type of Inhibitor or Target | Source Company |
| --- | --- | --- | --- |
| ANA-971 | Antiviral | TLR-7 agonist | Anadys |
| TMC-465350 | Antiviral | serine protease inhibitor | Medivir/ Tibotec |

The compounds of the disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: CDI for 1,1'-carbonyldiimidazole; THF for tetrahydrofuran; DBU for 1,8-diazabicyclo[5.4.0]undec-7-ene; TFA for trifluoroacetic acid; HATU for O-(7-azabenzotriazol-1-yl)-N,N,N',N'-tetramethyluronium phosphate; PyBOP for benzotriazol-1-yl-oxy-tris-pyrrolidino-phosphoniumhexafluorophosphate; MeI for methyl iodide; Boc or BOC for tert-butoxycarbonyl; OtBu for tert-butoxy; TBME for tert-butyl methyl ether; Et$_3$N for triethylamine; DMSO for dimethylsulfoxide; OAc for acetate; DPPA for diphenylphosphoryl azide; Me for methyl; TBAF for tetrabutylammonium fluoride; DMAP for 4-N,N-dimethylaminopyridine; tBuLi for tert-butyllithium; LiHMDS for lithium hexamethyldisilazide; Tle for tert-butylleucine, also referred to as tert-butyl glycine; 4-BiphMgBr for 4-biphenylmagnesium bromide; DCM for dichloromethane; MeO for methoxy; EDAC or EDC for 1-(3-dimethylaminopropyl)-3-ethylcarbodiimide hydrochloride; and HOBt for 1-hydroxybenzotriazole.

The starting materials useful to synthesize the compounds of the present disclosure are known to those skilled in the art and can be readily manufactured or are commercially available.

The following methods set forth below are provided for illustrative purposes and are not intended to limit the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Scheme II shows the general process wherein compounds of formula (I) are constructed by the coupling of tripeptide carboxylic acid with a P1' sulfonamide. Said coupling reaction requires treatment of carboxylic acid (1) with a coupling reagent such as carbonyl diimidazole in a solvent such as THF, which can be heated to reflux, followed by the addition of the formed derivative of (1), to the P1' sulfonamide, in a solvent such as THF or dichloromethane in the presence of a base such as DBU.

Scheme II

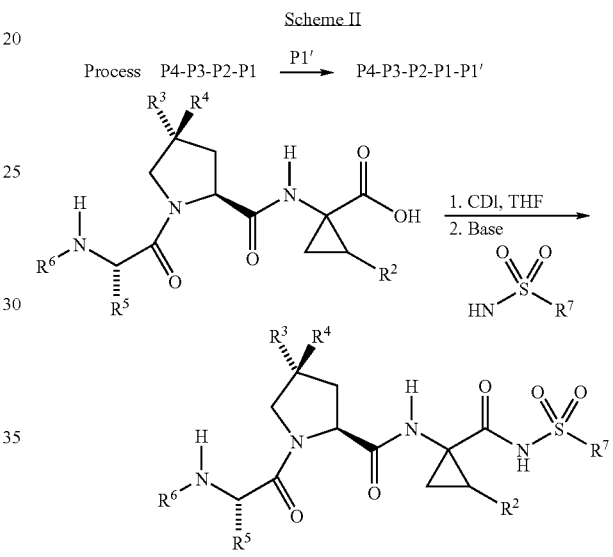

An alternative process for the construction of compounds of formula (I) is shown in Scheme III. The P1' sulfonamide element is coupled to the P1 element using the process employed in Scheme I. The resulting P1-P1' moiety can then be deprotected at its amino terminus. In this general example a Boc protecting group is employed but one skilled in the art would recognize that a number of suitable amino protecting groups could be employed in this process. The Boc protecting group can be removed using acid such as trifluoroacetic acid in a solvent such as dichloroethane to provide the deprotected amine as the TFA salt. The TFA amine salt can be directly employed in the subsequent coupling reaction or as an alternative the TFA amine salt can be first converted to the HCl amine salt, and this HCl amine salt is used in said coupling reaction as shown in Scheme III. The coupling of the HCl amine salt (3) with the carboxyl terminus a P4-P3-P2 intermediate can be achieved using coupling reagents, such as HATU, in solvents such as dichloromethane to provide compounds of formula (I) (4).

Scheme III

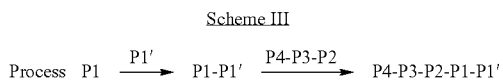

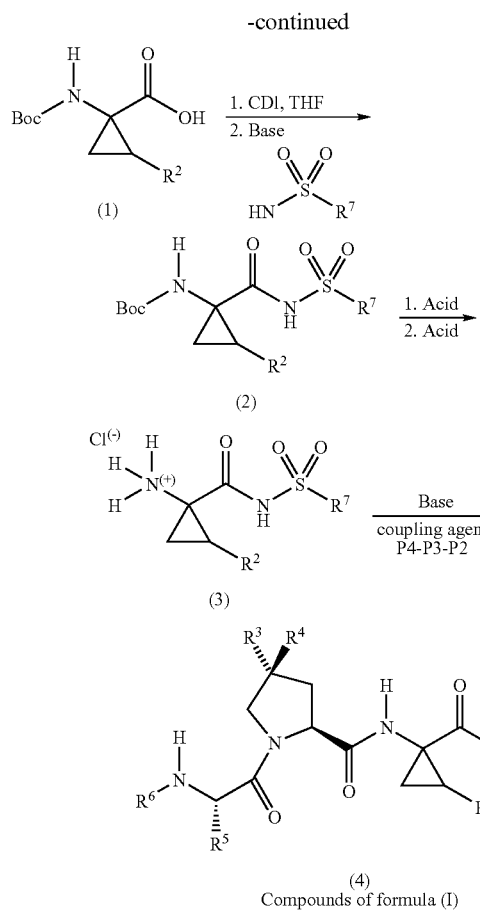

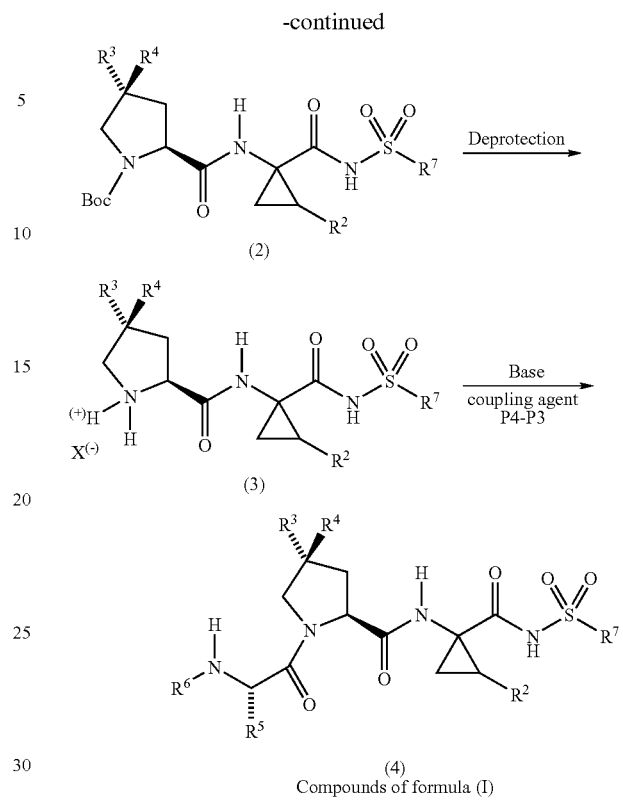

An alternative process for the construction of compounds of formula (I) is shown in Scheme IV. Herein the hydrochloride salt of the P1-P1' terminal amine (1) is coupled to the free carboxyl group of the P2 element using coupling agents such as PyBOP, in the presence of a base such as diisopropyl amine, and in a solvent such as dichloromethane. The resulting P2-P1-P1' intermediate can be converted to compounds of formula (I) in a two step process wherein the first step is deprotection of the P2 amine terminus using an acid such as TFA in a solvent such as dichloromethane. The resulting trifluoroacetic acid salt can be coupled with the carboxyl terminus of the P4-P3 element using standard coupling agents such as PyBOP in the presence of base such as diisopropyl amine, and using solvents such as dichloromethane to provide compounds of formula (I) (4).

The P4-P3-P2 intermediate utilized in the above schemes can be constructed as previously described with a further description of this process shown in general Scheme V. Therein the free carboxyl terminus of the P4-P3 intermediate (1), can be coupled to the amino terminus of the P2 element to provide the P4-P3-P2 dipeptide (2). The carboxyl terminus of the P4-P3-P2 intermediate can be deprotected by saponification of the ester group to provide P4-P3-P2 as the free carboxylic acid (3). Intermediates like (3) can be converted to compounds of formula (I) using the methods described herein.

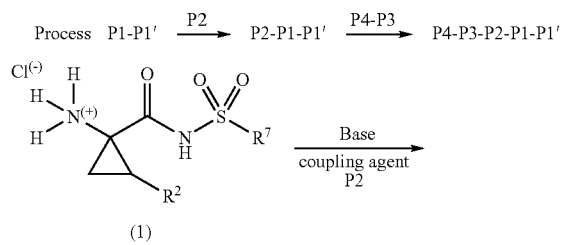

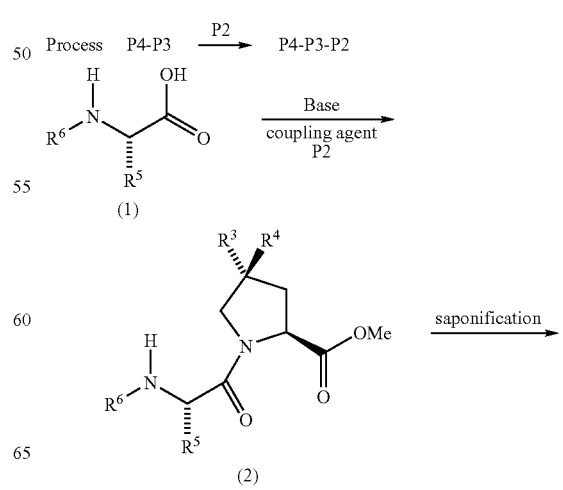

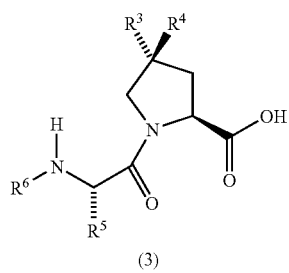

(3)

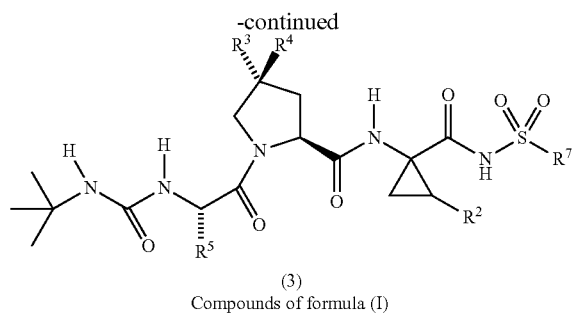

(3)
Compounds of formula (I)

Compounds of formula (I) can also be converted into other compounds of formula (I) as described herein. An example of such a process is shown in Scheme VI where a compound of formula (I) (1) which bears a Boc group at the P4 position is converted to a compound of formula (I) (3) wherein said compound bears a urea group at the P4 position. The conversion of (1) to (3) can be carried out in a two step process the first of which is the conversion of (1) to amine (2) by treatment of (1) with an acid such as TFA in a solvent such as dichloromethane. The resulting amine TFA salt can be treated with an isocyanate such as tert-butylisocyanate in the presence of one equivalent of base to provide a compound of formula (I) (3) wherein the P3 moiety is capped with a urea. As previously noted one skilled in the art will recognize that intermediate (2) can be used as starting materials for the preparation of compounds of formula (I) wherein the P3 group is capped with an amide or a sulfonamide, or thiourea, or a sulfamide. The construction of said compounds of formula (I) can be achieved using standard conditions for the formation of said P4 functionalities from amines.

In the construction of compounds of formula (I), the P1' terminus is incorporated into the molecules using one of the general processes outlined above and described in more detail below. In some examples the P1' elements are cycloalkyl- or alkyl-sulfonamides which are commercially available or can be prepared from the corresponding alkyl- or cycloalkyl-sulfonyl chloride by treating said sulfonyl chloride with ammonia. Alternatively, these sulfonamides can be synthesized using the general process outline in Scheme VII. Therein commercially available 3-chloro-propylsulfonyl chloride (1) is converted to a suitable protected sulfonamide as for example by treatment with tert-butyl amine. The sulfonamide obtained (2) is then converted to the corresponding cycloalkylsulfonamide by treatment with two equivalents of a base such as butyllithium in a solvent such as THF. The resulting cycloalkylsulfonamide can be deprotected by treatment with an acid to provide the desired unprotected cycloalkylsulfoamide.

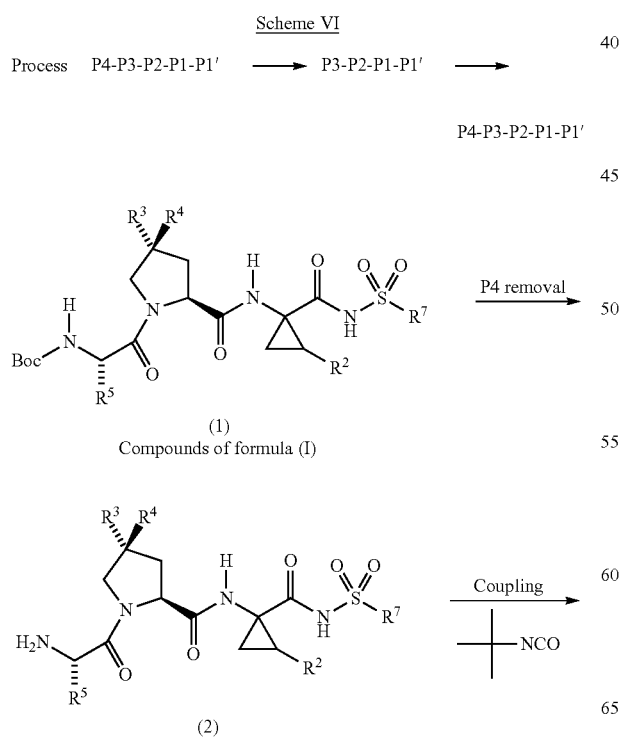

Scheme VI

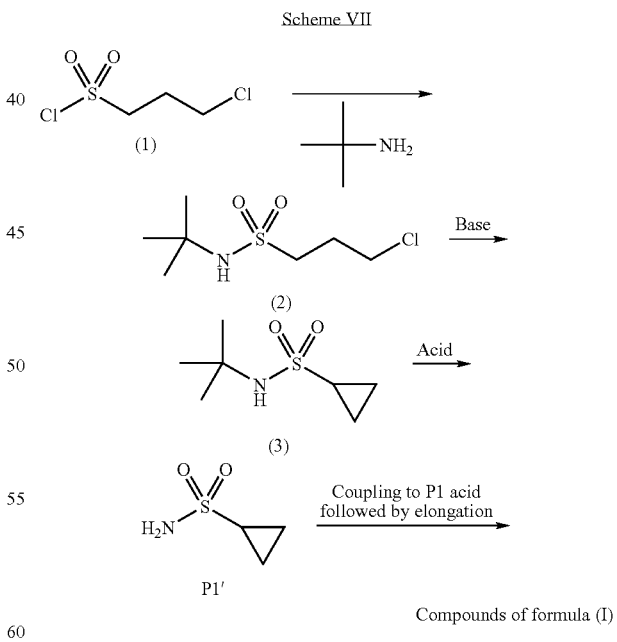

Scheme VII

Substituted cycloalkylsulfonamides can also be incorporated into compounds of formula (I) using a modification of the above said procedure. For example, intermediate 2 of Scheme VIII can be treated with two equivalents of base such as butyllithium and the resulting reaction mixture can be treated with an electrophile such as methyliodide to provide a substituted cycloalkylsulfonamide (3). This intermediate (3) can be deprotected at the N-terminus and the resulting compound (4) utilized as an intermediate in the preparation of compounds of formula (I).

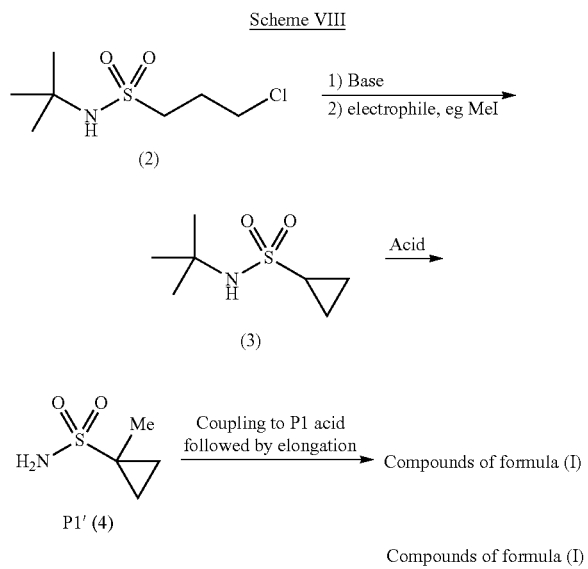

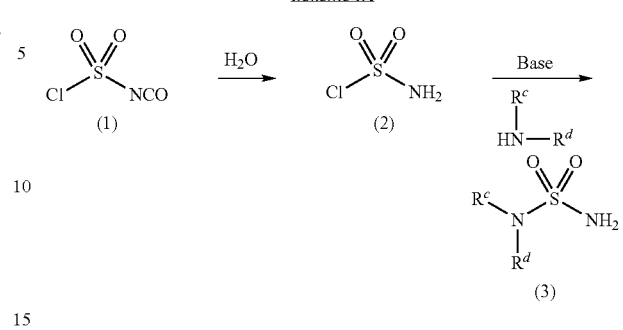

The P1' intermediates employed in generating compounds of formula (I) are in some cases derived from sulfamide derivatives. In such cases the sulfamide intermediates are available by several synthetic routes as for example by the pathway outlined in Scheme IX.

Sulfamoyl chloride (2) can be prepared in situ by the addition of water (e.g. 1 equiv) to chlorosulfonyl isocyanate 1 (e.g. 1 equiv) in a solvent such as THF, maintained at a low temperature such as −20° C., and the resulting solution is allowed to warm to 0° C. To this solution a base, such as anhydrous triethylamine (eg., 1 equiv), is added followed by an amine (eg., 1 equiv). The reaction mixture is then warmed to room temperature, filtered and the filtrate concentrated to afford the desired sulfamides (3).

The sulfamides can be incorporated into compounds of formula (I) following the synthetic pathway defined in Scheme X. Therein, a carboxylic acid P1 element (1) is treated with an activating agent such as CDI. In a separate flask, a strong base is added to a solution of the above described sulfamide and the resulting reaction mixture is stirred for several hours after which this reaction mixture is added to the flask containing the activated carboxylic acid, to provide acylsulfamide derivatives (2). Intermediates like 2 can be converted to compounds of formula (I) as described herein.

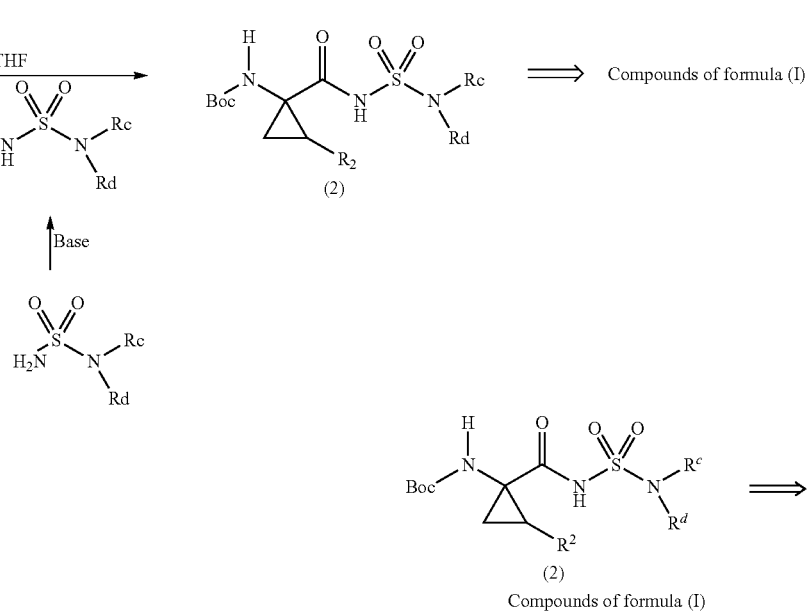

It should be noted that acylsulfamide derivatives can also be prepared from tripeptide carboxylic acids in a one step process as defined in Scheme XI.

undergo ester cleavage and thereby this enantiomer (5a) is recovered from the reaction mixture. However, the other enantiomer, (5b) which houses the (1S,2R) stereochemistry

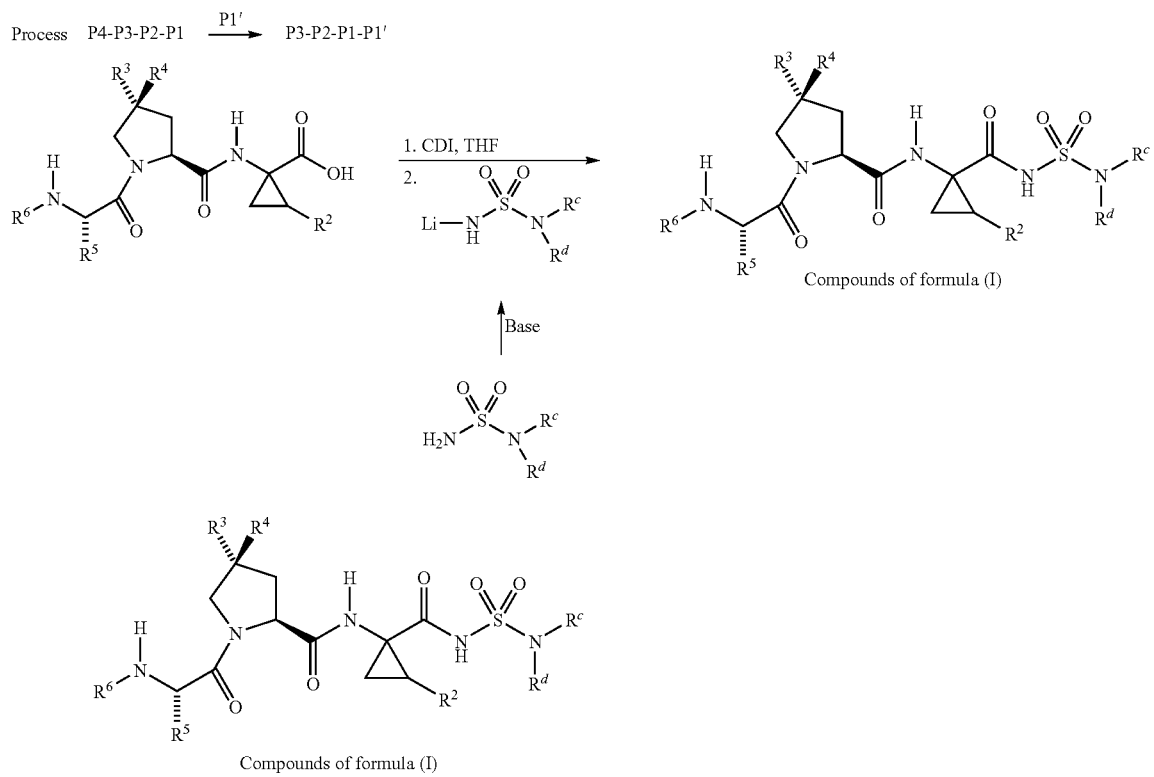

The P1 elements utilized in generating compounds of formula (I) are in some cases commercially available, but are otherwise synthesized using the methods known to one skilled in the art and in a non-limiting sense described herein and subsequently incorporated into compounds of formula (I) using the methods described herein. The substituted P1 cyclopropylamino acids can be synthesized following the general process outline in Scheme XII.

Treatment of commercially available or easily synthesized imine (1) with 1,4-dihalobutene (2) in presence of a base produces, provides the resulting imine (3). Acid hydrolysis of (3) then provides (4), which has an allyl substituent syn to the carboxyl group as a major product. The amine moiety of (4) can protected using a Boc group to provide the fully protected amino acid (5). This intermediate is a racemate which can be resolved by an enzymatic process wherein the ester moiety of (5) is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In an embodiment of the examples cited herein, the stereoisomer for integration into compounds of formula (I) is (5a) which houses the (1R,2S) stereochemistry. In the presence of the enzyme, this enantiomer does not undergoes ester cleavage, i.e., hydrolysis, to provide the free acid (6). Upon completion of this reaction, ester (5a) can be separated from the acid product (6) by routine methods such as, for example, aqueous extraction methods or chromatography.

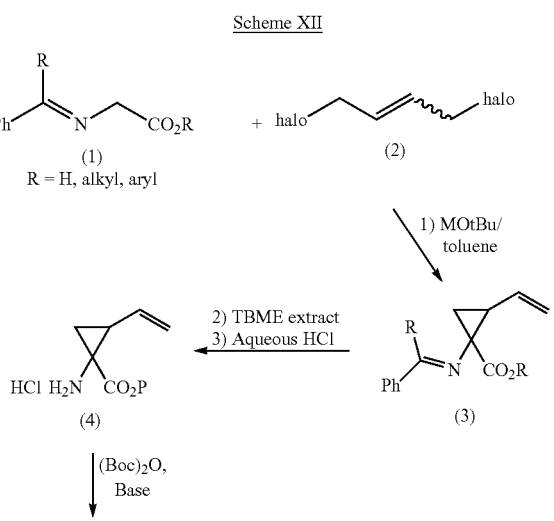

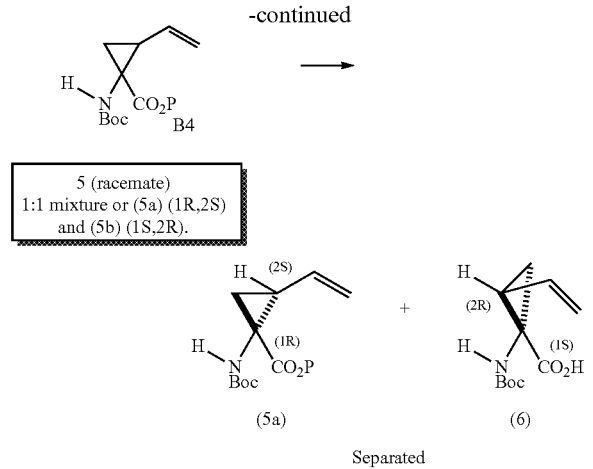

Non-limiting procedures for making P2 intermediates and compounds of formula (I) are shown in the Schemes below. Said intermediates, reaction conditions and methods given in the specific examples are broadly applicable to compounds with other substitution patterns. For example, the synthesis of P2 elements found in compounds of formula (I) of Scheme XIII can be prepared following the defined synthetic path. Therein readily, or commercially available N-Boc-4-oxo-L-proline, or N-Cbz-4-oxo-L-proline is treated with an organometallic agent such as a Grignard reagent (or alternatively an alkyl or aryl lithium species, or alternatively an alkyl, or aryl zinc species) to provide intermediate (2) in which the C4 position of the proline bears an $R^3$ substituent and a free tertiary hydroxy group. The alcohol functionality of intermediate (2) can then functionalized to provide the desired $R^8$ functionality. In this process the alcohol of intermediate (2) can be engaged in a series of well established reactions in the art. For example the alcohol of (2) can be acylated to provide esters, carbamates or carbonates; alkylated to provide ethers and phosphonated to provide phosphates. For the conversion of intermediate (2) to intermediate (3) of Scheme XIII it may be necessary to first protect the carboxylic acid group of (2) as shown.

The chemistry for the functionalization of alcohols is described in standard texts on the subject such as: Comprehensive Organic Transformations: A Guide to Functional Group Preparations. Second Addition, by Richard Larock. This text is published by Wiley and Sons. Therein specific references and reviews are highlighted which one skilled in the art can readily employ for the conversion of intermediate (2) of Scheme XIII to intermediate (3). For example conditions and pertinent references for the formation of ethers from alcohols can be found on pages 883 through 929 of Larock's text. More specifically, the conditions and references cited on pages 890-894 are most pertinent for the construction to practice of the current disclosure. Likewise conditions for the conversion of alcohols to the corresponding ester derivatives can be found on pages 1952 and 1955 of Laroch's text. In addition, the chemistry described in *Journal of Organic Chemistry* 2001, volume 66, page 8926 and pertinent references cited within are useful for the construction to practice of the current disclosure.

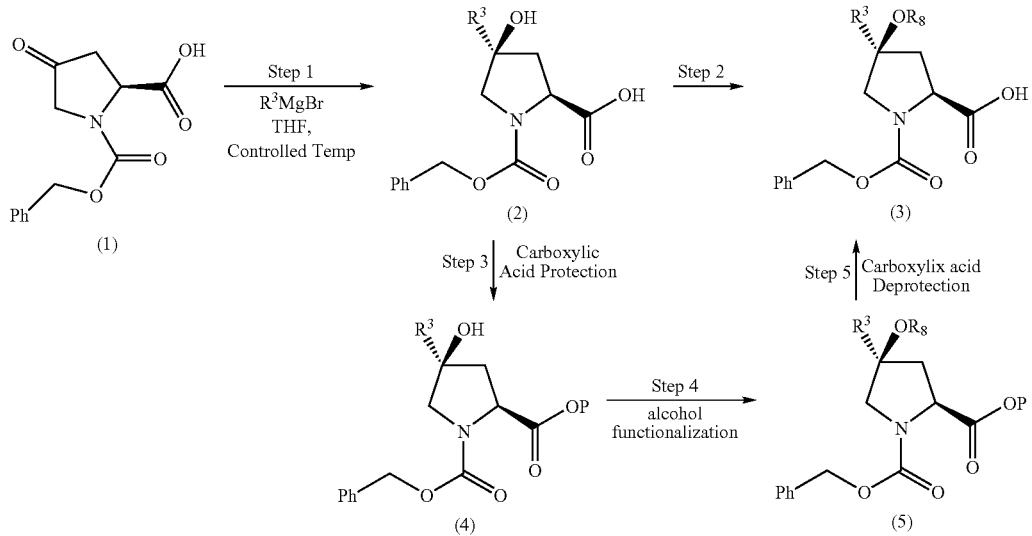

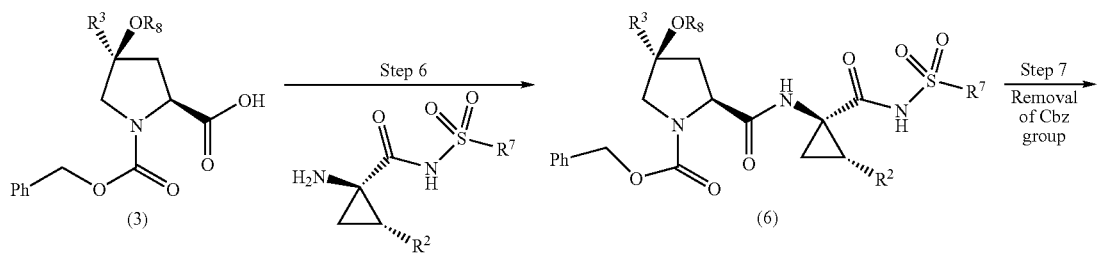

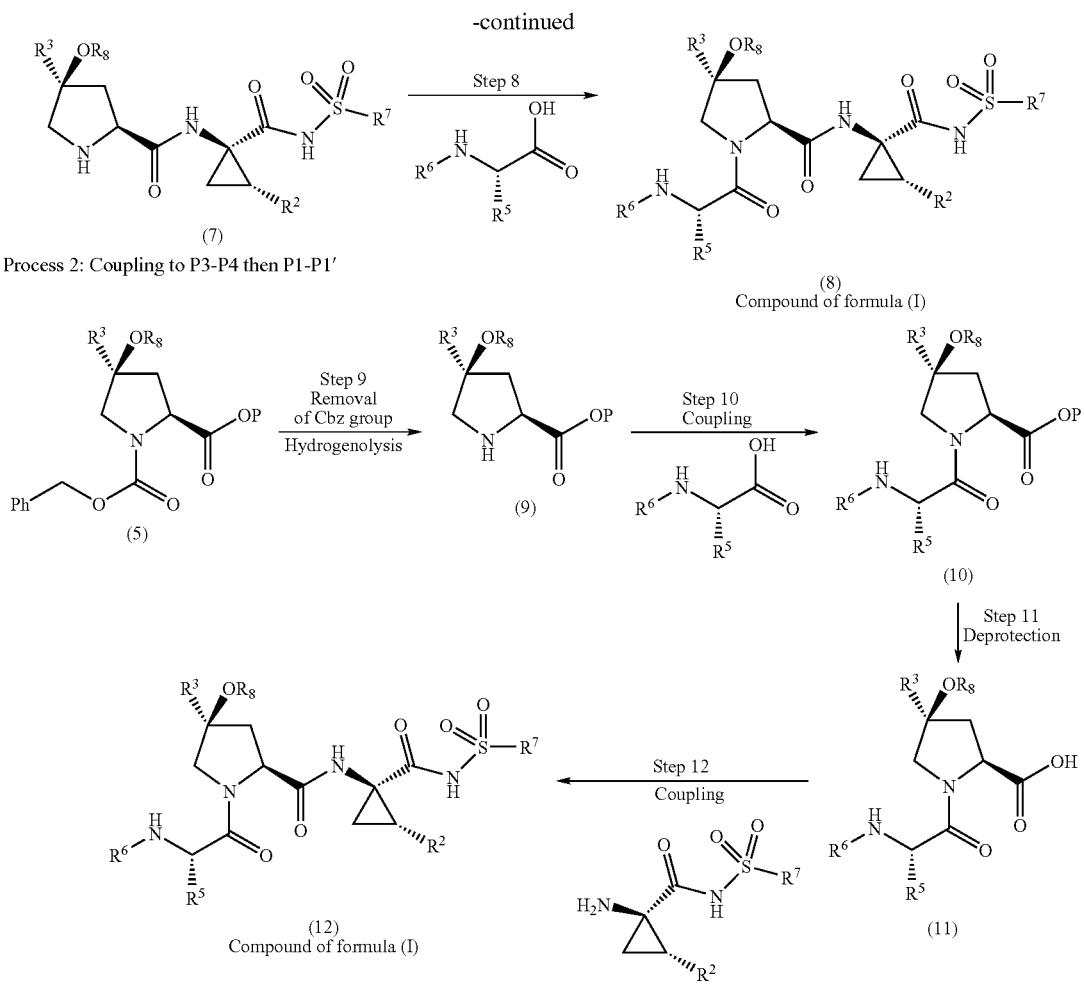

(7)
Process 2: Coupling to P3-P4 then P1-P1'

(8)
Compound of formula (I)

(12)
Compound of formula (I)

An alternative approach to the synthesis of compounds of formula (I) as depicted in Scheme XIII is shown in Scheme XIV. Functionalization of the C4 position of the proline group occurs via Grignard addition to a late stage intermediate (5) to provide intermediate 6 which can then be converted to compounds of formula (I). Intermediate (5) is available via a 4-step sequence beginning with commercially available intermediate (1), the first step of which involves coupling of (1) to a P1-P1' intermediate coupling reagents established in the art. Acid-catalyzed deprotection of the N-Boc group of intermediate (2) provides free amine intermediate (3) which is subsequently coupled with the P3-P4 fragment to provide intermediate (4). The selective oxidation of the C4 hydroxy group in intermediate (4) to provide intermediate (5) can be achieved using oxidizing reagents such as the Dess-Martin reagent.

Scheme XIV

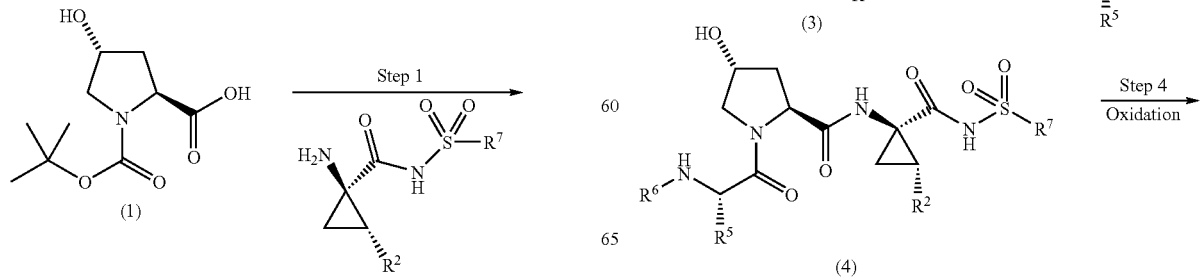

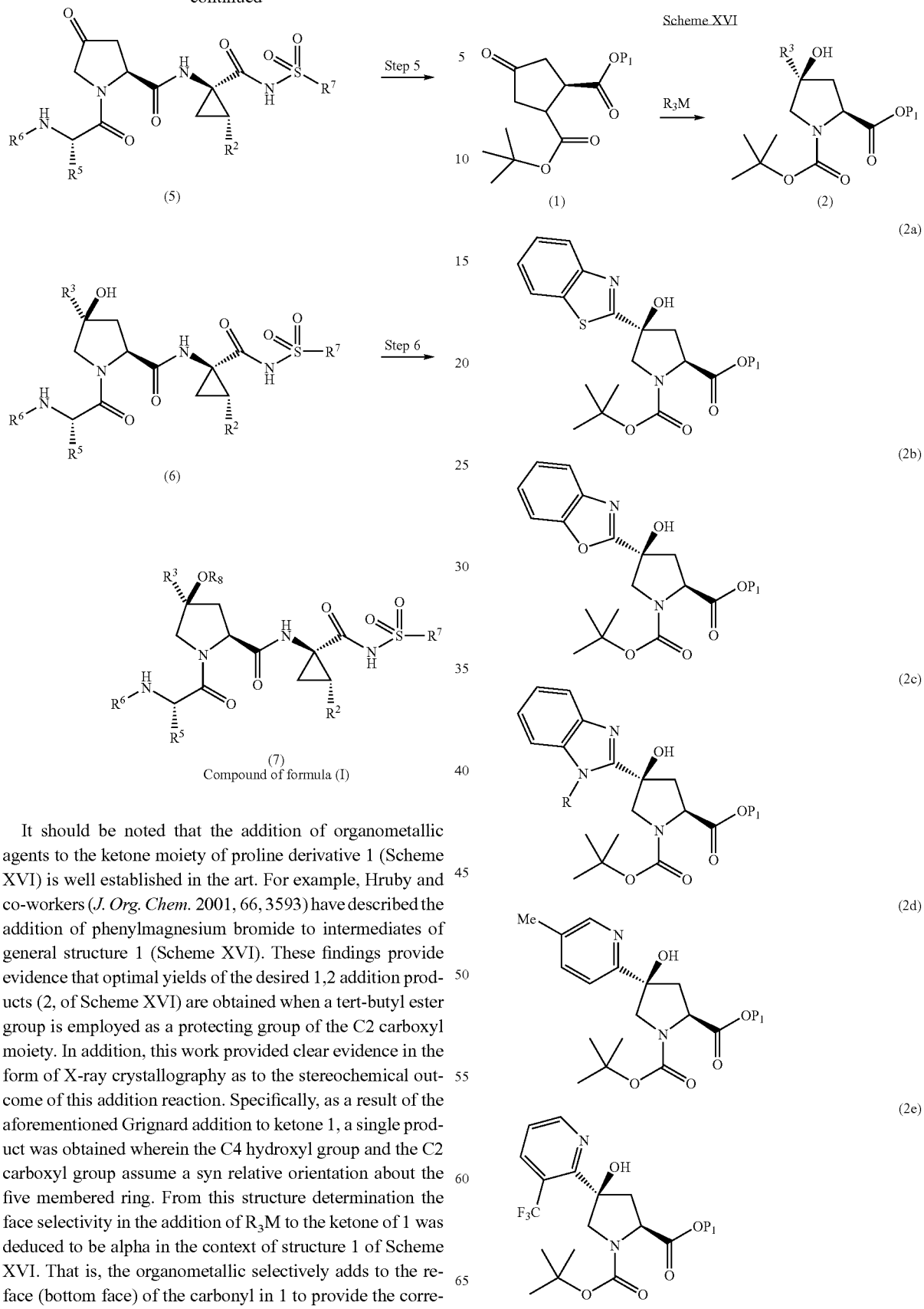

It should be noted that the addition of organometallic agents to the ketone moiety of proline derivative 1 (Scheme XVI) is well established in the art. For example, Hruby and co-workers (J. Org. Chem. 2001, 66, 3593) have described the addition of phenylmagnesium bromide to intermediates of general structure 1 (Scheme XVI). These findings provide evidence that optimal yields of the desired 1,2 addition products (2, of Scheme XVI) are obtained when a tert-butyl ester group is employed as a protecting group of the C2 carboxyl moiety. In addition, this work provided clear evidence in the form of X-ray crystallography as to the stereochemical outcome of this addition reaction. Specifically, as a result of the aforementioned Grignard addition to ketone 1, a single product was obtained wherein the C4 hydroxyl group and the C2 carboxyl group assume a syn relative orientation about the five membered ring. From this structure determination the face selectivity in the addition of $R_3M$ to the ketone of 1 was deduced to be alpha in the context of structure 1 of Scheme XVI. That is, the organometallic selectively adds to the re-face (bottom face) of the carbonyl in 1 to provide the corresponding tertiary alcohol (2) with the stereochemistry shown.

-continued (2f) 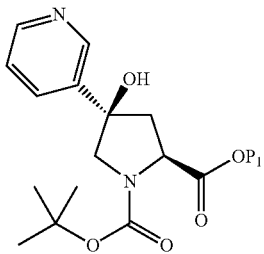

(2g) 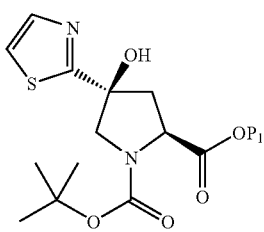

(2h) 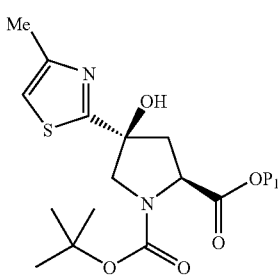

(2i) 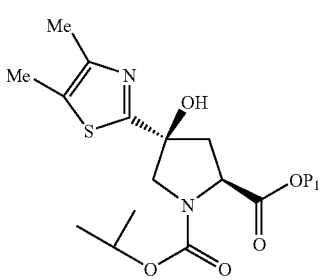

(2j) 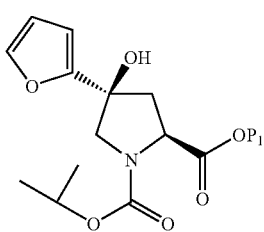

(2k) 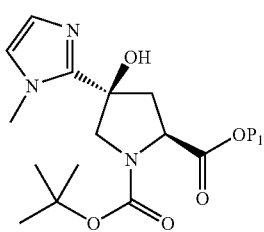

-continued

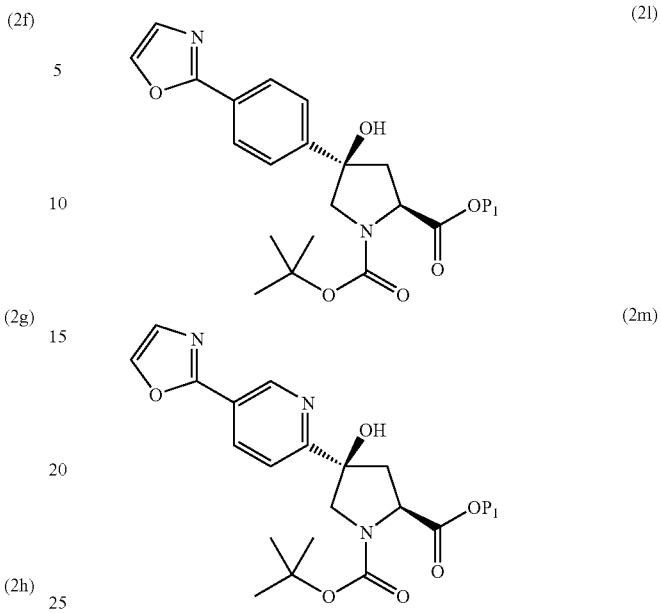

The aforementioned work of Hruby describes the addition of a specific Grignard reagent to derivatives of 1 (Scheme XVI). However, the addition of a variety of Grignard reagents to proline 1 is exemplified in the present disclosure. The body of literature that describes the addition of organometallic agents, including Grignard reagents, to ketones is considerable and is summarized in general overviews in the art such as: *Comprehensive Organic Functional Group Transformations.* Volume 2: *Synthesis: Carbon with one heteroatom attached by a single bond.* Editor in Chief Alan. R. Katritzky, et al. 1995. Chapter 2.02, page 37. This class of reactions is also described in *Comprehensive Organic Synthesis.* Editor in Chief Barry M Trost, Volume 1: Additions to C—X pi-bonds (part 1). 1991.

Recent research in the art provides conditions for further optimization of Grignard reagents in addition reactions to ketones and these works may be useful in the present disclosure. For example Ishihara and co-workers (Org. Lett. 2005, Vol. 7, No. 4, 573) recently described the formation and utility of magnesium ate complexes. Magnesium ate comples, $R_3MgLi$, are derived from Grignard reagents and alkyllithiums. As described by Ishihara these complexes provide excellent yields of 1,2 addition products in reactions to ketones. In a separate study, Knochel and co-workers (Angew. Chem. Int. Ed. 2006, 45, 497) have described the use of soluble Lanthanide salts such as $LnCl_3$ in conjunction with organomagnesium reagents. The presence of these Lanthanide salts results in an improvement in the efficiency of the 1,2 addition reaction to carbonyl compounds. These works, and references cited therein, establish the state of the art with respect to the optimization of the Grignard reaction in simple additions to carbonyl compounds and serve as an important source of information in the present disclosure.

It should also be noted that a range of organometallic reagents participate in addition reactions to ketones. Included in this body of work are reagents such as aryllithium, alkyllithium and heteroaryllithium reagents, which are well known to add in a 1,2 fashion to carbonyl moieties. For example, in a recent study by Dondoni and co-workers (*J. Org. Chem.* 2005, 70, 9257) benzothiazole is lithiated using BuLi and the resulting C2-lithium species adds in a 1,2 fashion to a lactone. By way of analogy lithiated benzothiazole would be expected to add in a 1,2 fashion to ketone 1 of Scheme XVI to provide an intermediate like 2a.

One skilled in the art would recognize that organometallic reagents derived from heterocycles such as oxazoles and thiazoles and imidazoles can also participate in 1,2 addition reactions to ketone 1. There is a considerable body of literature that defines the unique conditions employed for each of these heterocycle systems and this information is readily available to one skilled in the art. For example, the use of organometallic reagents derived from benzoxazole or oxazole, in addition reactions to ketones requires the use of lithium magnesates. The specifics of this recent study by Bayh and co-workers is described in *J. Org. Chem.*, 2005, 70, 5190. The addition of benzoxazole to ketone 1 of Scheme XVI would provide access to intermediates like 2b.

There is significant literature precedent for the addition to ketones using a wide range of organometallic reagents derived from heterocycles. For example the work of Behinda and co-workers (Tet. Lett. 42, 2001, 647) describes the formation of a lithiated benzimidazole and its addition to a simple lactone. By analogy, the use of this lithiated benzimidazole in addition reactions to ketone 1 of Scheme XVI would provide access to intermediates like 2c. In addition, a recent study by Kawasaki and co-workers (Bioorganic and Medicinal Chem. Lett. 13, 2003, 87) describes the formation of a series of lithiated heteroaromatic compounds and their addition reactions to activated amides. By analogy the use of these lithiated heteroaromatic intermediates in addition reactions to ketone 1 of Scheme XVI would provide access to intermediates 2d-2k.

The employment of organometallics derived from biaryl, or heteroaryl-aryl systems in addition 1,2 reactions to ketone 1 is also pertinent to the present disclosure. The addition of this class of organometallic reagents to ketone 1 would provide access to intermediates like 2l and 2m. It should be noted that in the exemplification of the present disclosure, it may be necessary to synthesize biaryl, or hetero-aryl organometallics for subsequent use in addition reactions to ketone 1 of Scheme XVI. One skilled in the art would recognize the significant body of literature which describes the preparation of organometallics of this type and precursors thereof. For example a recent review by Chinchilla and co-workers (Chem. Rev. 2004, 104, 2667) describes the preparation of metalated heterocycles and their utility. The basic chemistry for the preparation of biaryl or heteroaryl-aryl systems often employ Suzuki like coupling reactions. A body of literature put forth by Gregory Fu describes the state of the art in such coupling reactions and a subset of these references follow: *JACS* 2004, 126, 1340; *JACS*, 2002, 124, 13662; *Angew. Chem. Int. Ed.* 2002, 41, No. 11, 1945; *Angew. Chem. Int. Ed.* 2002, 41, No. 20, 3910; *JACS* 2002, 122, 4020; *JACS* 2001, 123, 10099; *Org. Lett.* 2001, Vol. 3, No. 26, 4295; *Angew. Chem. Int. Ed.* 1998, 37, No. 24, 3387. In addition to this body of work critical reviews in the area are readily available such as by Rossi in *Synthesis* 2004, No. 15, 2419.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts ($\delta$) are reported in parts per million. Flash chromatography was carried out on silica gel ($SiO_2$) according to Still's flash chromatography technique (*J. Org. Chem.* 1978, 43, 2923).

The intermediates described in the Examples found herein can be employed to synthesize compounds of Formula 1.

Example 1

Preparation of P1' Intermediates

1. Preparation of Cyclopropylsulfonamide

Method 1:

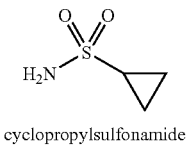

cyclopropylsulfonamide

Scheme 1

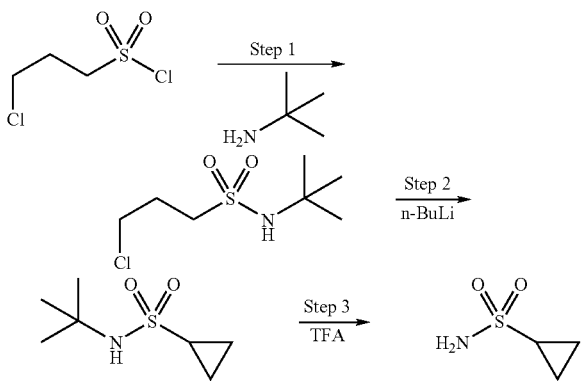

Step 1 tert-Butylamine (3.0 mol, 315 mL) was dissolved in THF (2.5 L). The solution was cooled to −20° C. 3-Chloropropanesulfonyl chloride (1.5 mol, 182 mL) was added slowly. The reaction mixture was allowed to warm to room temperature and stirred for 24 hours. The mixture was filtered and the filtrate was concentrated in vacuo. The residue was dissolved in $CH_2Cl_2$ (2.0 L). The resulting solution was washed with 1.0M HCl (1.0 L), water (1.0 L), and brine (1.0 L), dried over $Na_2SO_4$, filtered, and concentrated in vacuo to give a slightly yellow solid, which was crystallized from hexane to provide the product as a white solid (316.0 g, 99%). $^1H$ NMR ($CDCl_3$) $\delta$ 1.38 (s, 9H), 2.30-2.27 (m, 2H), 3.22 (t, J=7.35 Hz, 2H), 3.68 (t, J=6.2 Hz, 2H), 4.35 (b, 1H).

Step 2

To a solution of the product of Step 1 (2.14 g, 10.0 mmol) in THF (100 mL) was added n-BuLi (2.5 M in hexane, 8.0 mL, 20.0 mmol) at −78° C. The reaction mixture was allowed to warm up to room temperature over period of 1 hour and concentrated in vacuo. The residue was partitioned between ethyl acetate and water (200 mL each). The separated organic phase was washed with brine, dried over $Na_2SO_4$, filtered, and concentrated in vacuo. The residue was recrystallized from hexane to provide the desired product as a white solid (1.0 g, 56%). $^1$H NMR (CDCl$_3$) δ 0.98-1.00 (m, 2H), 1.18-1.19 (m, 2H), 1.39 (s, 9H), 2.48-2.51 (m, 1H), 4.19 (b, 1H).

Step 3

A solution of the product of Step 2 (110 g, 0.62 mmol) in TFA (500 mL) was stirred at room temperature for 16 hours. The volatiles were removed in vacuo. The residue was recrystallized from ethyl acetate/hexane (60 mL/240 mL) to provide the desired product as a white solid (68.5 g, 91%). $^1$H NMR (DMSO-d$_6$) δ 0.84-0.88 (m, 2H), 0.95-0.98 (m, 2H), 2.41-2.58 (m, 1H), 6.56 (b, 2H).

Method 2:

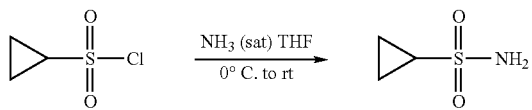

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF. The solution was warmed to room temperature overnight and stirred one additional day. The mixture was concentrated until 1-2 mL of solvent remained and poured onto a 30 g plug of $SiO_2$ (eluted with 30% to 60% ethyl acetate/hexanes) to provide 3.45 g (100%) of cyclopropylsulfonamide as a white solid. $^1$H NMR (methanol-d$_4$) δ 0.94-1.07 (m, 4H), 2.52-2.60 (m, 1H); $^{13}$C NMR (methanol-d$_4$) δ 5.92, 33.01.

2. Preparation of C1-Substituted Cyclopropylsulfonamides

2a. Preparation of N-tert-butyl-(1-methyl)cyclopropyl-sulfonamide

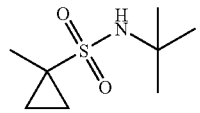

Step 1: Preparation of N-tert-butyl-(3-chloro)propylsulfonamide

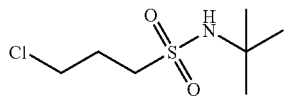

Prepared as described above.

Step 2: Preparation of N-tert-butyl-(1-methyl)cyclopropyl-sulfonamide

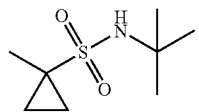

A solution of the product of Step 1 (4.3 g, 20 mmol) was dissolved in dry THF (100 mL) and cooled to −78° C. To this solution was added n-butyllithium (17.6 mL, 44 mmol, 2.5M in hexane) slowly. The dry ice bath was removed and the reaction mixture was warmed to room temperature over a period of 1.5 hours. This mixture was cooled to −78° C. and a solution of n-butyllithium (20 mmol, 8 mL, 2.5M in hexane) was added. The reaction mixture was warmed to room temperature, cooled to −78° C. over a period of 2 hours, and treated with a neat solution of methyl iodide (5.68 g, 40 mmol). The reaction mixture was warmed to room temperature overnight, then quenched with saturated $NH_4Cl$ (100 mL) at room temperature and extracted with ethyl acetate (100 mL). The organic phase was washed with brine (100 mL), dried (MgSO$_4$), filtered, and concentrated in vacuo to provide a yellow oil which was crystallized from hexane to provide the desired product as a slightly yellow solid (3.1 g, 81%): $^1$H NMR (CDCl$_3$) δ 0.79 (m, 2H), 1.36 (s, 9H), 1.52 (m, 2H), 1.62 (s, 3H), 4.10 (br s, 1H).

Step 3: Preparation of 1-methylcyclopropylsulfonamide

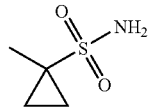

A solution of the product of Step 2 (1.91 g, 10 mmol) was dissolved in TFA (30 mL), and the reaction mixture stirred at room temperature for 16 hours. The solvent was removed in vacuo to provide a yellow oil which was crystallized from ethyl acetate/hexane (1:4, 40 mL) to provide the desired product as a white solid (1.25 g, 96%): $^1$H NMR (CDCl$_3$) δ 0.84 (m, 2H), 1.41 (m, 2H), 1.58 (s, 3H), 4.65 (br s, 2H). Anal. Calcd. For $C_4H_9NO_2S$: C, 35.54; H, 6.71; N, 10.36. Found: C, 35.67; H, 6.80; N, 10.40.

2b. Preparation of 1-propylcyclopropylsulfonamide

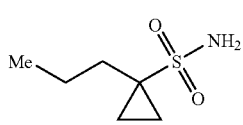

This compound was prepared using the procedure described for the preparation of 1-methylcyclopropylsulfonamide substituting propyl halide for methyl iodide in the second step of this process.

2c. Preparation of 1-allylcyclopropylsulfonamide

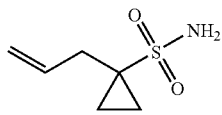

Step 1: Preparation of N-tert-butyl-(1-allyl)cyclopropylsulfonamide

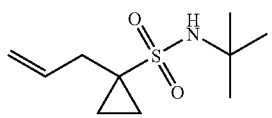

This compound was obtained in 97% yield according to the procedure described in the synthesis of N-tert-butyl-(1-methyl)cyclopropylsulfonamide using 1.25 equivalents of allyl bromide as the electrophile. The compound was used in the next reaction without further purification: $^1$H NMR (CDCl$_3$) δ 0.83 (m, 2H), 1.34 (s, 9H), 1.37 (m, 2H), 2.64 (d, J=7.3 Hz, 2H), 4.25 (br s, 1H), 5.07-5.10 (m, 2H), 6.70-6.85 (m, 1H).

Step 2: Preparation of 1-allylcyclopropylsulfonamide

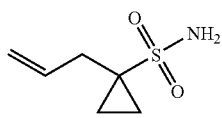

This compound was obtained in 40% yield from the product of Step 1 according to the procedure described in the synthesis of 1-methylcyclopropylsulfonamide. The compound was purified by column chromatography over SiO$_2$ using 2% methanol in dichloromethane as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 2H), 5.82 (m, 1H); $^{13}$C NMR (CDCl$_3$) δ 11.2, 35.6, 40.7, 119.0, 133.6.

2d. Preparation of 1-Benzylcyclopropylsulfonamide

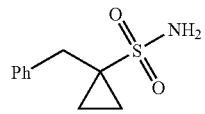

Step 1: Preparation of N-tert-butyl-(1-benzyl)cyclopropyl-sulfonamide

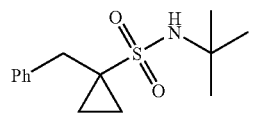

This compound was obtained in 60% yield using the procedure described for the synthesis of N-tert-butyl-(1-methyl)cyclopropylsulfonamide except 1.05 equivalents of benzyl bromide were used, followed by trituration with 10% ethyl acetate in hexane: $^1$H NMR (CDCl$_3$) δ 0.92 (m, 2H), 1.36 (m, 2H), 1.43 (s, 9H), 3.25 (s, 2H), 4.62 (br s, 1H), 7.29-7.36 (m, 5H).

Step 2: Preparation of 1-Benzylcyclopropylsulfonamide

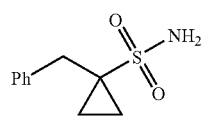

This compound was obtained in 66% yield from N-tert-butyl(1-benzyl)cyclopropylsulfonamide using the procedure described for the synthesis of 1-methylcyclopropylsulfonamide, followed by recrystallization from the minimum amount of 10% ethyl acetate in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

2e. Preparation of 1-(1-cyclohexenyl)cyclopropyl-sulfonamide

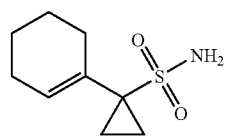

Step 1: Preparation of N-tert-butyl-[1-(1-hydroxy)cyclohexyl]-cyclopropylsulfonamide

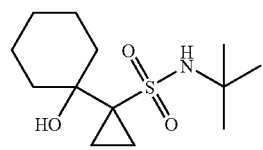

This compound was obtained in 84% yield using to the procedure described for the synthesis of N-tert-butyl-(1-methyl)cyclopropylsul-fonamide except 1.30 equivalents of cyclohexanone were used, followed by recrystallization from the minimum amount of 20% ethyl acetate in hexane: $^1$H NMR (CDCl$_3$) δ 1.05 (m, 4H), 1.26 (m, 2H), 1.37 (s, 9H), 1.57-1.59 (m, 6H), 1.97 (m, 2H), 2.87 (br s, 1H), 4.55 (br s, 1H).

Step 2: Preparation of 1-(1-cyclohexenyl)cyclopropyl-sulfonamide

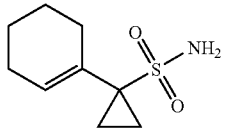

This compound, 1-(1-cyclohexenyl)-cyclopropylsulfonamide was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of ethyl acetate and hexane: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$−1).

2f. Preparation of 1-benzoylcyclo-propylsulfonamide

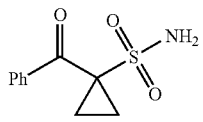

Step 1: Preparation of N-tert-butyl-(1-benzoyl)cyclopropyl-sulfonamide

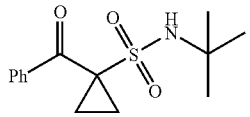

This compound was obtained in 66% yield using the procedure described for the synthesis of N-tert-butyl-(1-methyl) cyclopropylsulfonamide except 1.2 equivalents of methyl benzoate was used as the electrophile. The compound was purified by column chromatography over SiO$_2$ using 30% to 100% dichloromethane in hexane: $^1$H NMR (CDCl$_3$) δ 1.31 (s, 9H), 1.52 (m, 2H), 1.81 (m, 2H), 4.16 (br s, 1H), 7.46 (m, 2H), 7.57 (m, 1H), 8.05 (d, J=8.5 Hz, 2H).

Step 2: Preparation of 1-benzoylcyclo-propylsulfonamide

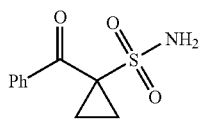

This compound was obtained in 87% yield from N-tert-butyl(1-benzoyl)cyclopropylsul-fonamide using the process described for the synthesis of 1-methylcyclopropylsulfonamide, followed by recrystallization from the minimum amount of ethyl acetate in hexane: $^1$H NMR (DMSO-d$_6$) δ 1.39 (m, 2H), 1.61 (m, 2H), 7.22 (s, 2H), 7.53 (t, J=7.6 Hz, 2H), 7.65 (t, J=7.6 Hz, 1H), 8.06 (d, J=8.2 Hz, 2H); $^{13}$C NMR (DMSO-d$_6$) δ 12.3, 48.4, 128.1, 130.0, 133.4, 135.3, 192.0.

2g. Preparation of N-tert-butyl-(1-phenylaminocarboxy)-cyclopropylsulfonamide

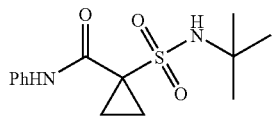

This compound was obtained in 42% yield using the procedure described for the synthesis of N-tert-butyl-(1-methyl) cyclopropylsulfonamide using 1 equivalent of phenylisocyanate, followed by recrystallization from the minimum amount of ethyl acetate in hexane $^1$H NMR (CDCl$_3$) δ 1.38 (s, 9H), 1.67-1.71 (m, 4H), 4.30 (br s, 1H), 7.10 (t, J=7.5 Hz, 1H), 7.34 (t, J=7.5 Hz, 2H), 7.53 (t, J=7.5 Hz, 2H).

3. Preparation of C1-Substituted Cyclopropanesulfonamides: the Use of an N-Boc Protecting Group 3a. Preparation of Cyclopropylsulfonylamine tert-butyl Carbamate, a Key Intermediate in the Preparation of C1-Substituted Cyclopropylsulfonamides

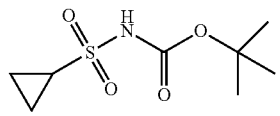

Step 1: Preparation of 3-chloropropylsulfonamide

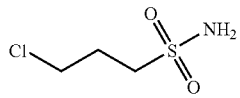

A solution of 3-chloropropanesulfonyl chloride (55 g, 310.7 mmol) was dissolved in THF (200 mL) and added dropwise over 30 minutes to a solution of NH$_4$OH (200 mL) at 0° C. The reaction mixture was warmed to room temperature, stirred 1 hour, and the aqueous layer extracted with dichloromethane (4×500 mL). The combined extracts were washed with 1N HCl (150 mL), water (150 mL), dried over MgSO$_4$, filtered, and concentrated in vacuo. The crude solid was recrystallized from the minimum amount of dichloromethane in hexanes to provide the desired product as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step 2: Preparation of 3-chloropropylsulfonylamine tert-butylcarbamate

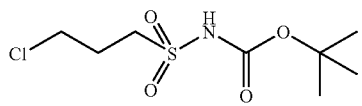

A solution of the product of Step 1 (30.2 g, 191.5 mmol), triethylamine (30.2 mL, 217.0 mmol), and 4-DMAP (2.40 g, 19.6 mmol) in dichloromethane (350 mL) at 0° C. was treated dropwise with a solution of di-tert-butyldicarbonate (47.2 g, 216.9 mmol) in dichloromethane (250 mL) over 30 minutes. The reaction mixture was warmed to room temperature, stirred an additional 3 hours, and was washed with 1N HCl (300 mL), water (300 mL), and brine (300 mL), dried over MgSO$_4$, filtered, and concentrated in vacuo to provide the crude product. This material was triturated with 70 mL of 5% dichloromethane in hexanes to provide the desired product as an off-white solid (47.2 g, 96%): $^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

Step 3: Preparation of cyclopropylsulfonylamine tert-butyl carbamate

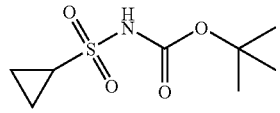

A solution of n-butyllithium (74.7 mL, 119.5 mmol, 1.6M in hexane) was dissolved in dry THF (105 mL) and cooled to −78° C. under an argon atmosphere. To this solution was added a solution of the product of Step 2 (14 g, 54.3 mmol) in dry THF (105 mL) dropwise over 20-30 minutes. The dry ice bath was removed and the reaction mixture was allowed to warm to room temperature over a period of 2 hours. The reaction mixture was quenched with glacial acetic acid (3.4 mL), concentrated in vacuo, and partitioned between dichloromethane (100 mL) and water (100 mL). The organic phase was washed with brine (100 mL), dried (MgSO$_4$), filtered, and concentrated in vacuo to provide the desired product as a waxy off-white solid (12.08 g, 100%): $^1$H NMR (CDCl$_3$) δ 1.10 (m, 2H), 1.34 (m, 2H), 1.50 (s, 9H), 2.88 (m, 1H), 7.43 (s, 1H). $^{13}$C NMR (CDCl$_3$) δ 6.21, 28.00, 31.13, 84.07, 149.82.

3b. Preparation of 1-methoxy-methylcyclopropy-sulfonamide

Step 1: Preparation of 1-methoxymethylcyclopropylsulfonylamine tert-butylcarbamate

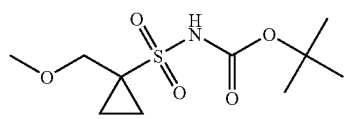

To a solution of cyclopropylsulfonylamine tert-butyl carbamate (1.0 g, 4.5 mmol) dissolved in THF (30 mL) cooled to −78° C., was added n-butyllithium (6.4 mL, 10.2 mmol, 1.6M in hexane) and the reaction mixture was stirred for 1 hour. To this solution was added a neat solution of chloromethyl methyl ether (0.40 mL, 5.24 mmol), and the mixture was slowly allowed to warm to room temperature overnight. The solution pH was adjusted to 3 using 1N aqueous HCl and was then extracted with ethyl acetate (4×50 mL portions). The combined extracts were dried (MgSO$_4$), filtered, and concentrated to afford 1-methoxymethylcyclopropylsulfonylamine tert-butylcarbamate, as a waxy solid (1.20 g, 100%) which was taken directly into the next reaction without further purification: $^1$H NMR (CDCl$_3$) δ 1.03 (m, 2H), 1.52 (s, 9H), 1.66 (m, 2H), 3.38 (s, 3H), 3.68 (s, 2H), 7.54 (s, 1H); $^{13}$C NMR (CDCl$_3$) δ 11.37, 28.29, 40.38, 58.94, 73.43, 83.61, 149.57.

Step 2: Preparation of 1-methoxymethylcyclopropysulfonamide

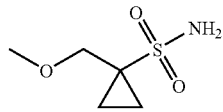

A solution of 1-methoxymethylcyclopropylsulfonylamine tert-butylcarbamate (1.14 g, 4.30 mmol) was dissolved in a solution of 50% TFA/dichloromethane (30 mL) and was stirred at room temperature for 16 hours. The solvent was removed in vacuo and the residue chromatographed over 80 g of SiO$_2$ (eluting with 0% to 60% ethyl acetate/hexanes to 1-methoxymethylcyclopropylsulfonamide as a white solid (0.55 g, 77% overall over two steps): $^1$H NMR (CDCl$_3$) δ 0.95 (m, 2H), 1.44 (m, 2H), 3.36 (s, 3H), 3.65 (s, 2H), 4.85 (s, 2H); $^{13}$C NMR (CDCl$_3$) δ 11.17, 40.87, 59.23, 74.80; LRMS m/z 183 (M$^+$+NH$_4$).

3c. Preparation of 1-cyclopropylmethylcyclopropylsulfonamide

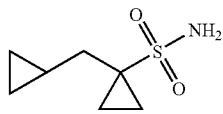

Step 1: Preparation of 1-cyclopropylmethylcyclopropylsulfonylamine tert-butylcarbamate

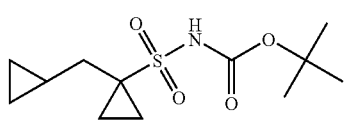

1-Cyclopropylmethylcyclopropylsulfonylamine tert-butylcarbamate was obtained in 92% yield according to the procedure described in the synthesis of 1-methoxymethylcyclopropylsulfonylamine tert-butylcarbamate, except 1.10 equivalents of cyclopropylmethyl bromide were used as electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-cyclopropylmethyl-cyclopropylsulfonamide

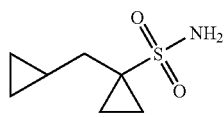

This compound was obtained in 65% yield from 1-cyclopropylmethylcyclopropylsulfonylamine tert-butylcarbamate according to the procedure described for the synthesis of 1-methoxymethylcyclopropylsulfonamide. The compound was purified by column chromotography over SiO$_2$ using 0% to 60% ethyl acetate in hexanes as the eluent: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3d. Preparation of 1-propylcarbamoylcyclopropane-sulfonamide

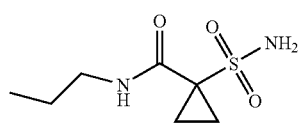

Step 1: Preparation of 1-propylcarbamoylcyclopropanesulfonamide tert-butylcarbamate

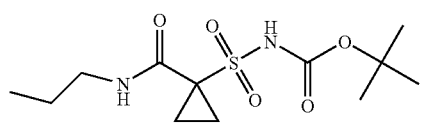

This compound was obtained in a crude 100% yield according to the procedure described for the synthesis of 1-methoxymethylcyclopropylsulfonylamine tert-butyl-carbamate except that 1.10 equivalents of n-propyl isocyanate was used as the electrophile. The compound was taken directly into the next reaction without purification: $^1$H NMR (CDCl$_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

Step 2: Preparation of 1-propylcarbamoylcyclopropane-sulfonamide

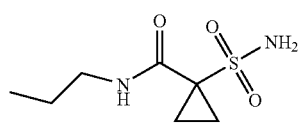

This compound was obtained in 50% yield from 1-propylcarbamoylcyclopropanesulfonamide tert-butylcarbamate according to the procedure described for the synthesis of 1-methoxymethylcyclopropylsulfonamide, except that no chromatography was used as the material was recrystallized from the minimum amount of dichloromethane/hexanes: $^1$H NMR (CDCl$_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR (CDCl$_3$) δ 4.65, 7.74, 11.26, 35.62, 41.21; LRMS m/z 193 (M$^+$+NH$_4$).

3e. Preparation of 1-(3,5-dimethylisoxazol-4-yl)carbamoylcyclopropanesulfonamide

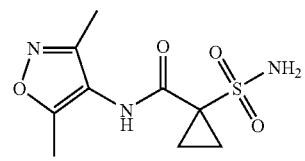

Step 1: Preparation of 1-(3,5-dimethylisoxazol-4-yl)carbamoylcyclopropanesulfonamide tert-butylcarbamate

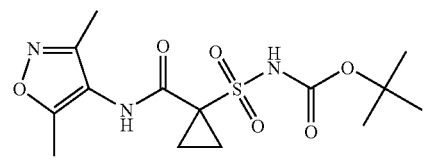

This compound was obtained in a crude 100% yield according to the procedure described for the synthesis of 1-methoxymethylcyclopropylsulfonylamine tert-butylcarbamate except that 1.20 equivalents of 3,5-dimethylisoxazole-4-isocyanate was used as the electrophile. The compound was taken directly into the next reaction without purification.

Step 2: Preparation of 1-(3,5-dimethylisoxazol-4-yl)carbamoylcyclopropanesulfonamide

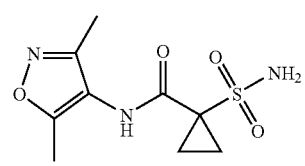

This compound was obtained in 50% yield (580 mg) from 1.62 g (4.52 mmol) of 1-(3,5-dimethylisoxazol-4-yl)carbamoylcyclo-propanesulfonamide tert-butylcarbamate using 30 mL (120 mmol) of 4N HCl/dioxanes, stirring overnight, concentration and chromatography over a Biotage 40M column (eluting with 0% to 5% methanol/dichloromethane: $^1$H NMR (methanol-d$_4$) δ 1.57 (m, 2H), 1.61 (m 2H), 2.15 (s, 3H), 2.30 (s, 3H), 4.84 (s, 3H); $^{13}$C NMR (methanol-d$_4$) δ 9.65, 10.94, 15.01, 46.11, 114.82, 159.45, 165.55, 168.15; LRMS m/z 260 (M$^+$+H).

4. Preparation of Cycloalkylsulfonamides from Cyloalkylbromides

4a. Preparation of Cyclobutylsulfonamide from Cylobutyl Bromide

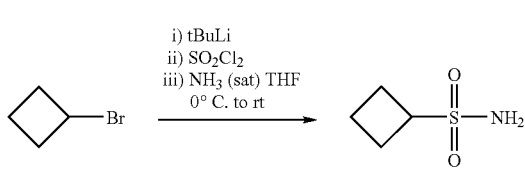

To a solution of 5.0 g (37.0 mmol) of cyclobutyl bromide in 30 mL of anhydrous diethyl ether (diethyl ether) cooled to −78° C. was added 44 mL (74.8 mmol) of 1.7M tert-butyllithium in pentanes. The solution was slowly warmed to −35° C. over 1.5 hours. This mixture was cannulated slowly into a solution of 5.0 g (37.0 mmol) of freshly distilled sulfuryl chloride in 100 mL of hexanes cooled to −40° C., warmed to 0° C. over 1 hour and carefully concentrated in vacuo. This mixture was redissolved in diethyl ether, washed once with some ice-cold water, dried (MgSO$_4$), filtered, and concentrated carefully. This mixture was redissolved in 20 mL of THF, added dropwise to 500 mL of saturated NH$_3$ in THF, and was allowed to stir overnight. The mixture was concentrated in vacuo to a crude yellow solid and was recrystallized from the minimum amount of dichloromethane in hexanes with 1-2 drops of methanol to provide 1.90 g (38%) of the desired product as a white solid. $^1$H NMR (CDCl$_3$) δ 1.95-2.06 (m, 2H), 2.30-2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M−H)$^-$ calcd for C$_4$H$_8$NSO$_2$: 134.0276. Found 134.0282.

4b. Preparation of Cyclopentyl Sulfonamide

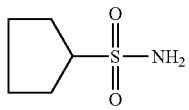

A solution of 18.5 mL (37.0 mmol) of 2M cyclopentylmagnesium chloride in ether was added dropwise to a solution of 3.0 mL (37.0 mmol) freshly distilled sulfuryl chloride (obtained from Aldrich) in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and the solution was then concentrated. The residue was recrystallized from the minimum amount of dichloromethane in hexanes with 1-2 drops of methanol to provide 2.49 g (41%) of the desired product as a white solid. $^1$H NMR (CDCl$_3$) δ 1.58-1.72 (m, 2H), 1.74-1.88 (m, 2H), 1.94-2.14 (m, 4H), 3.48-3.59 (m, 1H), 4.80 (br s, 2H); $^{13}$C NMR (CDCl$_3$) δ 25.90, 28.33, 63.54; MS m/e 148 (M−H)$^-$.

4c. Preparation of Cyclohexyl Sulfonamide

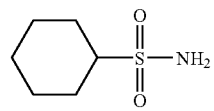

A solution of 18.5 mL (37.0 mmol) of 2M cyclohexylmagnesium chloride (TCI Americas) in diethyl ether was added dropwise to a solution of 3.0 mL (37.0 mmol) freshly distilled sulfuryl chloride in 100 mL of hexanes cooled to −78° C. The mixture was warmed to 0° C. over 1 hour and was then carefully concentrated in vacuo. This mixture was redissolved in diethyl ether (200 mL), washed once with some ice-cold water (200 mL), dried (MgSO$_4$), filtered, and concentrated carefully. This mixture was redissolved in 35 mL of THF, added dropwise to 500 mL of saturated NH$_3$ in THF and was allowed to stir overnight. The mixture was concentrated in vacuo to a crude yellow solid, the residue filtered through 50 g of silica gel using 70% ethyl acetate-hexanes as the eluent and was concentrated. The concentrate was recrystallized from the minimum amount of dichloromethane in hexanes with 1-2 drops of methanol to provide 1.66 g (30%) of the desired product as a white solid: $^1$H NMR (CDCl$_3$) δ 1.11-1.37 (m, 3H), 1.43-1.56 (m, 2H), 1.67-1.76 (m, 1H), 1.86-1.96 (m, 2H), 2.18-2.28 (m, 2H), 2.91 (tt, J=12, 3.5 Hz, 1H), 4.70 (br s, 2H); $^{13}$C NMR (CDCl$_3$) δ 25.04, 25.04, 26.56, 62.74; MS m/e 162 (M−1)$^-$.

4d. Preparation of Neopentylsulfonamide

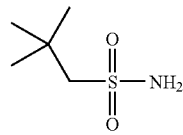

Following the procedure for the preparation of cyclohexylsulfonamide, 49 mL (37 mmol) of 0.75M neopentylmagnesium chloride (Alfa) in diethyl ether was converted to 1.52 g (27%) of the desired product as a white solid. $^1$H NMR (CDCl$_3$) δ 1.17 (s, 9H), 3.12 (s, 2H), 4.74 (brs, 2H); $^{13}$C NMR (CDCl$_3$) δ 29.46, 31.51, 67.38; MS m/e 150 (M−1)$^-$.

4e. Preparation of Cyclobutylcarbinylsulfonamide

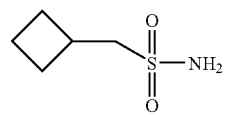

A solution of 12.3 g (83 mmol) of cyclobutylcarbinyl bromide (Aldrich) and 13.7 g (91 mmol) of sodium iodide in 150 mL of acetone was heated to reflux overnight and then cooled to room temperature. The inorganic solids were removed by filtration and the acetone and cyclopropylcarbinyl iodide (8.41 g, 46%) were removed by distillation (ambient temperature and 150 torr at 80° C., respectively).

A solution of 4.0 g (21.98 mmol) of cyclobutyl carbinyl iodide in 30 mL of anhydrous diethyl ether cooled to −78° C. was cannulated into a solution of 17 mL (21.98 mmol) of 1.3M sec-butyllithium in cyclohexanes and the solution was stirred for 5 minutes. To this mixture was cannulated a solution of 3.0 g (21.98 mmol) of freshly distilled sulfuryl chloride in 110 mL of hexanes cooled to −78° C., the mixture warmed to room temperature over 1 hour and was then carefully concentrated in vacuo. This mixture was redissolved in diethyl ether, washed once with some ice-cold water, dried (MgSO$_4$), filtered, and concentrated carefully. This mixture was redissolved in 30 mL of THF, added dropwise to 500 mL of saturated NH$_3$ in THF and was allowed to stir overnight. The mixture was concentrated in vacuo to a crude yellow solid and was recrystallized from the minimum amount of dichloromethane in hexanes with 1-2 drops of methanol to provide 1.39 g (42%) of the desired product as a white solid. $^1$H NMR (CDCl$_3$) δ 1.81-2.03 (m, 4H), 2.14-2.28 (m, 2H), 2.81-2.92 (m, 1H), 3.22 (d, J=7 Hz, 2H), 4.74 (brs, 2H); $^{13}$C NMR (CDCl$_3$) δ 19.10, 28.21, 30.64, 60.93. MS m/e 148 (M−H)$^−$.

4f. Preparation of Cyclopropylcarbinylsulfonamide

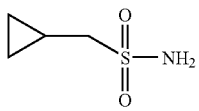

Using the procedure employed for the preparation of cyclobutylcarbinylsulfonamide, cyclopropylcarbinylsulfonamide was prepared from cyclopropylcarbinyl bromide (Aldrich) (see also *JACS* 1981, p. 442-445). $^1$H NMR (CDCl$_3$) δ 0.39-0.44 (m, 2H), 0.67-0.76 (m, 2H), 1.13-1.27 (m, 1H), 3.03 (d, J=7.3 Hz, 2H), 4.74 (brs, 2H); $^{13}$C NMR (CDCl$_3$) δ 4.33, 5.61, 59.93; MS m/e 134 (M−1).

4g. Preparation of 2-thiophenesulfonamide

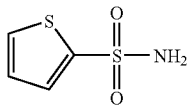

The desired product was prepared from 2-thiophenesulfonyl chloride (purchased from Aldrich) using the method described in *Justus Liebigs Ann. Chem.* 1933, 501, p. 174-182.

4h. Preparation of 4-bromobenzenesulfonamide

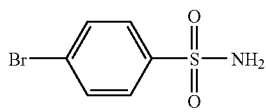

4-Bromophenylsulfonamide was Prepared by Treatment of Commercially available 4-bromosulfonyl chloride with saturated ammonia in THF.

5. General Procedure for the Preparation of Sulfamides

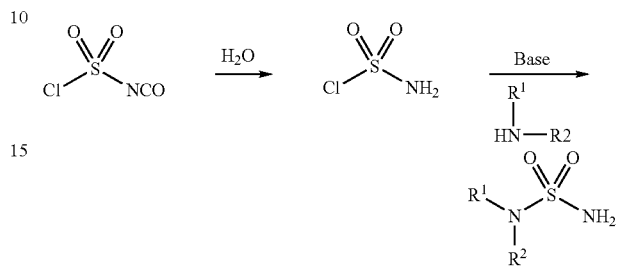

The intermediate sulfamoyl chloride was prepared by addition of water (1 equiv) in THF to a cold (−20° C.) stirred solution of chlorosulfonyl isocyanate (1 equiv) in THF and the resulting solution allowed to warm to 0° C. To this solution was added anhydrous triethylamine (1 equiv) followed by requisite secondary amine (1 equiv). The reaction mixture was warmed to room temperature, then filtered and the filtrate was concentrated to afford the desired sulfamides.

Example 2

Preparation of P1 Intermediates 5. 1-tert-Butoxycarbonylaminocyclopropane Carboxylic Acid is Commercially Available

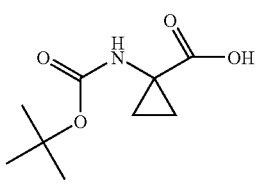

6. Preparation of 1-Aminocyclobutanecarboxylic Acid Methyl Ester-Hydrochloride

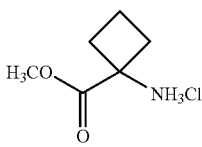

1-Aminocyclobutanecarboxylic acid (100 mg, 0.869 mmol)(Tocris) was dissolved in 10 mL of methanol. HCl gas was bubbled in for 2 hours. The reaction mixture was stirred for 18 hours, and then concentrated in vacuo to give 144 mg of a yellow oil. Trituration with 10 mL of diethyl ether provided 100 mg of the desired product as a white solid. $^1$H NMR (CDCl₃) δ 2.10-2.25 (m, 1H), 2.28-2.42 (m, 1H), 2.64-2.82 (m, 4H), 3.87 (s, 3H), 9.21 (br s, 3H).

7a. Preparation of (1R,2R)/(1S,2S) 1-amino-2-ethylcyclopropanecarboxylic acid tert-butyl ester (racemic mixture)

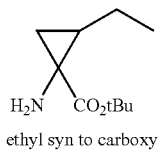
ethyl syn to carboxy

Step 1: Preparation of 2-ethylcyclopropane-1,1-dicarboxylic acid di-tert-butyl ester, shown below

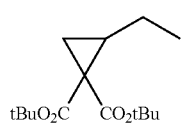

To a suspension of benzyltriethylammonium chloride (21.0 g, 92.2 mmol) in a 50% aqueous NaOH solution (92.4 g in 185 mL H₂O) was added 1,2-dibromobutane (30.0 g, 138.9 mmol) and di-tert-butylmalonate (20.0 g, 92.5 mmol). The reaction mixture was vigorously stirred for 18 hours at room temperature and treated with a mixture of ice and water. The crude product was extracted with dichloromethane (3×) and sequentially washed with water (3×), and brine. The organic extracts were combined, dried (MgSO₄), filtered, and concentrated in vacuo. The resulting residue was purified by flash column chromatography (100 g SiO₂, 3% diethyl ether in hexane) to provide the desired product (18.3 g, 67.8 mmol, 73% yield) which was used directly in the next reaction.

Step 2: Preparation of racemic 2-Ethylcyclopropane-1,1-dicarboxylic acid tert-butyl ester, shown below

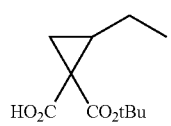

The product of Step 1 (18.3 g, 67.8 mmol) was added to a suspension of potassium tert-butoxide (33.55 g, 299.0 mmol) in dry diethyl ether (500 mL) at 0° C., treated with H₂O (1.35 mL, 75.0 mmol), and was vigorously stirred overnight at room temperature. The reaction mixture was poured in a mixture of ice and water and washed with diethyl ether (3×).

The aqueous layer was adjusted to acidic pH with a 10% aqueous citric acid solution at 0° C. and extracted with ethyl acetate (3×). The combined organic layers were washed with water (2×), brine, dried (MgSO₄), filtered, and concentrated in vacuo to provide the desired product as a pale yellow oil (10 g, 46.8 mmol, 69% yield).

Step 3: Preparation of (1R,2R)/(1S,2S) 2-ethyl-1-(2-trimethylsilanylethoxycarbonylamino)cyclopropanecarboxylic acid tert-butyl ester, shown below

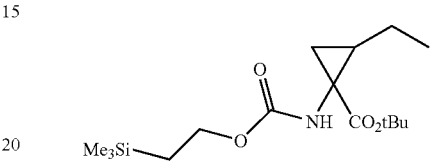

To a suspension of the product of Step 2 (10 g, 46.8 mmol) and 3 g of freshly activated 4 Å molecular sieves in dry benzene (160 mL) was added triethylamine (7.50 mL, 53.8 mmol) and DPPA (11 mL, 10.21 mmol). The reaction mixture was heated to reflux for 3.5 hours, treated with 2-trimethylsilylethanol (13.5 mL, 94.2 mmol), and heated to reflux overnight. The reaction mixture was filtered, diluted with diethyl ether, washed sequentially with 10% aqueous citric acid solution, water, saturated aqueous NaHCO₃, water (2×), and brine (2×), dried (MgSO₄), filtered, and concentrated in vacuo. The residue was suspended with 10 g of Aldrich polyisocyanate scavenger resin in 120 mL of dichloromethane, stirred at room temperature overnight, and filtered to provide the desired product (8 g, 24.3 mmol; 52%) as a pale yellow oil: ¹H NMR (CDCl₃) δ 0.03 (s, 9H), 0.97 (m, 5H), 1.20 (br m, 1H), 1.45 (s, 9H), 1.40-1.70 (m, 4H), 4.16 (m, 2H), 5.30 (br s, 1H).

Step 4: Preparation of (1R,2R)/(1S,2S) 1-amino-2-ethylcyclopropanecarboxylic acid tert-butyl ester (racemic mixture), shown below

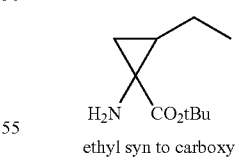
ethyl syn to carboxy

To the product of Step 3 (3 g, 9 mmol) was added a 1.0M TBAF solution in THF (9.3 mL, 9.3 mmol). The mixture was heated to reflux for 1.5 hours, cooled to room temperature, and diluted with 500 mL of ethyl acetate. The solution was successively washed with water (2×100 mL) and brine (2×100 mL), dried (MgSO₄), filtered, and concentrated in vacuo to provide the desired product.

7b. A General Method for the Conversion of Compounds of Formula I Bearing a P1 Vinyl P1 Substituent to the Corresponding Saturated P1 Analogue as Shown

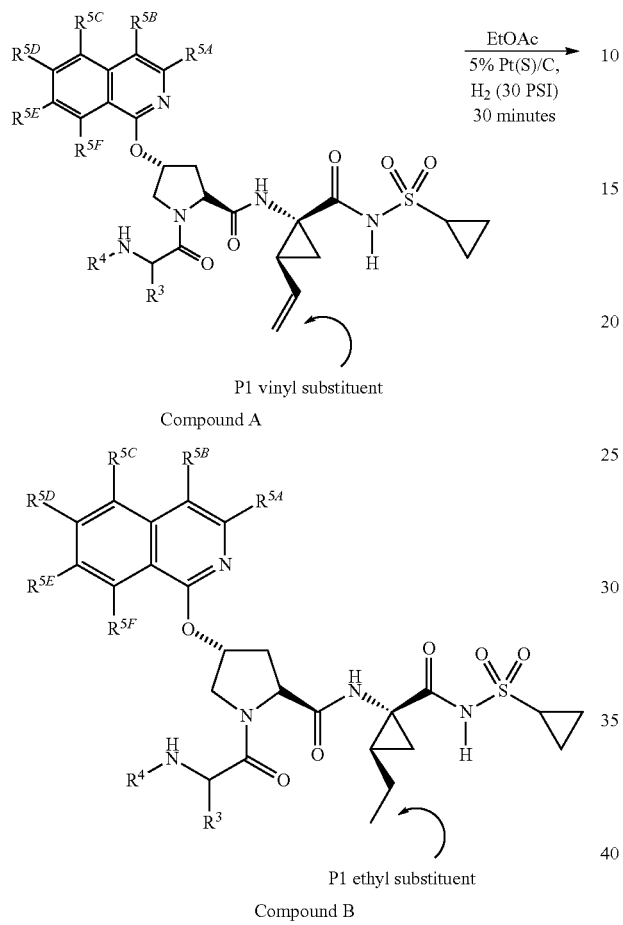

P1 vinyl substituent
Compound A

P1 ethyl substituent
Compound B

A suspension of Compound A (approximately 100 mg) and Pt(S)/C (5%, 10 mg) in approximately 15 mL of EtOAc was hydrogenated, $H_2$ (30 PSI) for 0.5 h. After filtration through a Ceilite plug, the filtrate was concentrated and purified to give the desired product, Compound B.

8. Preparation of racemic (1R,2S)/(1S,2R)-1-amino-2-vinylcyclopropane carboxylic acid ethyl ester Scheme 1

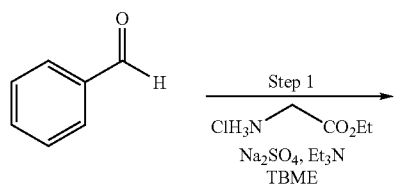

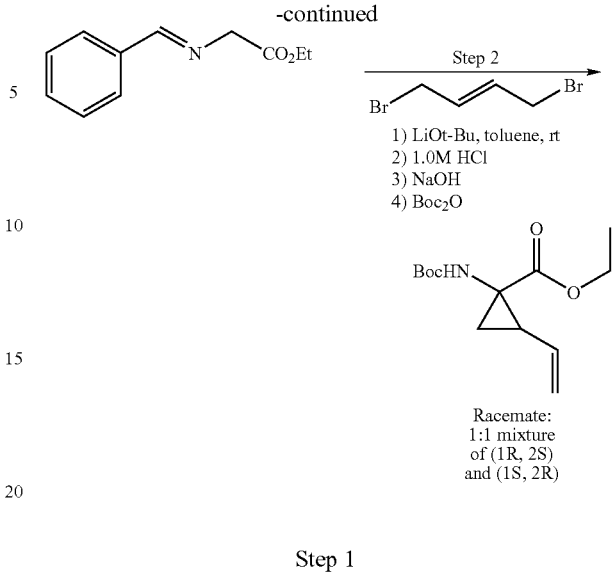

Racemate:
1:1 mixture
of (1R, 2S)
and (1S, 2R)

Step 1

Glycine ethyl ester hydrochloride (304 g, 2.16 mole) was suspended in tert-butylmethyl ether (1.6 L). Benzaldehyde (231 g, 2.16 mole) and anhydrous sodium sulfate (155 g, 1.09 mole) were added, and the mixture was cooled to 0° C. using an ice-water bath. Triethylamine (455 mL, 3.26 mole) was added dropwise over 30 minutes and the mixture was stirred for 48 hours at room temperature. The reaction was then quenched by addition of ice-cold water (1 L) and the organic layer was separated. The aqueous phase was extracted with tert-butylmethyl ether (0.5 L) and the organic phases were combined and washed with a mixture of saturated aqueous $NaHCO_3$ (1 L) and brine (1 L). The organic layer was dried over $MgSO_4$, filtered, and concentrated in vacuo to provide 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1 Hz, 2H), 7.39-7.47 (m, 3H), 7.78-7.81 (m, 2H), 8.31 (s, 1H).

Step 2

To a suspension of lithium tert-butoxide (84.1 g, 1.05 mol) in dry toluene (1.2 L), was added dropwise a mixture of the N-benzyl imine of glycine ethyl ester (100 g, 0.526 mol) and trans-1,4-dibromo-2-butene (107 g, 0.500 mol) in dry toluene (0.6 L) over 60 minutes. Upon completion of the addition, the deep red mixture was quenched by addition of water (1 L) and tert-butylmethyl ether (TBME, 1 L). The aqueous phase was separated and extracted a second time with TBME (1 L). The organic phases were combined, 1.0M HCl (1 L) was added and the mixture stirred at room temperature for 2 hours. The organic phase was separated and extracted with water (0.8 L). The aqueous phases were then combined, saturated with salt (700 g), and TBME (1 L) was added and the mixture was cooled to 0° C. The stirred mixture was then made basic to pH=14 by the dropwise addition of 10.0M NaOH, the organic layer was separated, and the aqueous phase was extracted with TBME (2×500 mL). The organic extracts were combined, dried over $MgSO_4$, filtered and concentrated to a volume of 1 L. To this solution of free amine was added $Boc_2O$ or di-tert-butyldicarbonate (131 g, 0.600 mol) and the mixture stirred for 4 days at room temperature. Additional di-tert-butyldicarbonate (50 g, 0.23 mol) was added to the reaction and the mixture was refluxed for 3 hours and was then allowed cool to room temperature overnight. The reaction mixture was dried over MgSO$_4$, filtered, and concentrated in vacuo to provide 80 g of crude material. This residue was purified by flash chromatography (2.5 kg of SiO$_2$, eluted with 1% to 2% CH$_3$OH/CH$_2$Cl$_2$) to provide 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43-1.49 (m, 1H), 1.76-1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M-1).

9. Resolution of N-Boc-(1R,2S)/(1S,2R)-1-amino-2-vinylcyclopropane carboxylic acid ethyl ester Scheme 2

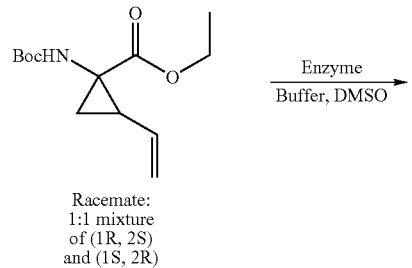

Racemate:
1:1 mixture
of (1R, 2S)
and (1S, 2R)

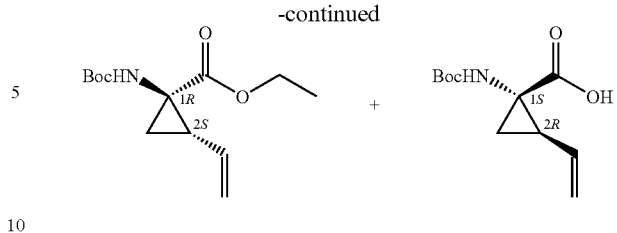

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Alcalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 minutes. The reaction temperature was then maintained at 40° C. for 24.5 hours during which time the pH of the mixture was adjusted to 8.0 at the 1.5 hour and 19.5 hour time points using 50% NaOH in water. After 24.5 hours, the enantio-excess of the ester was determined to be 97.2%, and the reaction was cooled to room temperature (26° C.) and stirred overnight (16 hours) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO$_3$ (3×100 mL), water (3×100 mL), and concentrated in vacuo to give the enantiomerically pure N-Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee")).

The aqueous layer from the extraction process was then acidified to pH 2 with 50% H$_2$SO$_4$ and extracted with MTBE (2×2 L). The MTBE extract was washed with water (3×100 mL) and concentrated to give the acid as light yellow solid (42.74 g; purity: 99% (210 nm, containing no ester).

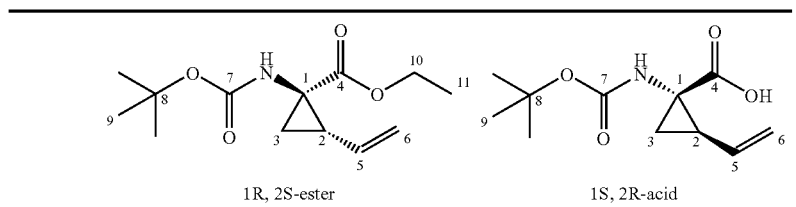

|  | ester | acid |
|---|---|---|
| High Resolution Mass Spec | (+) ESI, C$_{13}$H$_{22}$NO$_4$, [M + H]$^+$, calcd. 256.1549, found 256.1542 | (−) ESI, C$_{11}$H$_{16}$NO$_4$, [M − H]$^-$, calcd. 226.1079, found 226.1089 |

NMR observed chemical shift
    Solvent: CDCl$_3$ (proton δ 7.24 ppm, C-13 δ 77.0 ppm)
    Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |

| | -continued | | | |
|---|---|---|---|---|
| 3b | 1.46 (br) | | 1.51, (br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J =7.5 Hz) | 14.2 | — | — |

Resolution B

To 0.5 mL 100 mM Heps.Na buffer (pH 8.5) in a well of a 24 well plate (capacity: 10 mL/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hours, enantio-excess of the ester was determined to be 44.3% as following: 0.1 mL of the reaction mixture was removed and mixed well with 1 mL ethanol; after centrifugation, 10 microliter ("μL") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μL of the supernatant was analyzed with the chiral HPLC and enantio-excess of the ester was determined to be 100%.

Resolution C

To 0.5 mL 100 mM Heps.Na buffer (pH 8.5) in a well of a 24 well plate (capacity: 10 mL/well), 0.1 mL of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after centrifugation, 10 μL of the supernatant was analyzed with the chiral HPLC. To the remaining reaction mixture, 0.1 mL of DMSO was added, and the plate was incubated for additional 3 days at 250 rpm at 40° C., after which 4 mL of ethanol was added to the well. After centrifugation, 10 μL of the supernatant was analyzed with the chiral HPLC and enantio-excess of the ester was determined to be 100%.

Samples analysis was carried out in the following manner:

1) Sample preparation: About 0.5 mL of the reaction mixture was mixed well with 10 volume of ethanol. After centrifugation, 10 μL of the supernatant was injected onto HPLC column.

2) Conversion determination:

Column: YMC ODS A, 4.6×50 mm, S-5 μm

Solvent: A, 1 mM HCl in water; B, CH$_3$CN

Gradient: 30% B for 1 min; 30% to 45% B over 0.5 min; 45% B for 1.5 min; 45% to 30% B over 0.5 minutes.

Flow rate: 2 mL/min

UV Detection: 210 nm

Retention time: acid, 1.2 min; ester, 2.8 minutes.

3) Enantio-excess determination for the ester:

Column: CHIRACEL OD-RH, 4.6×150 mm, S-5 μm

Mobile phase: CH$_3$CN/50 mM HClO$_4$ in water (67/33)

Flow rate: 0.75 mL/min.

UV Detection: 210 nm.

Retention time:

(1S,2R)-1-amino-2-vinylcyclopropane carboxylic acid 5.2 min;

Racemate (1R,2S)/(1S,2R)-1-amino-2-vinylcyclopropane carboxylic acid ethyl ester 18.5 minutes and 20.0 min;

(1R,2S)-1-amino-2-vinylcyclopropane carboxylic acid ethyl ester 18.5 minutes.

Resolution D

5 L of 0.3 M sodium phosphate buffer (pH 8) was maintained at 38° C. in a 20 Liter jacked reactor, stirred at 130 rpm. Four liters of Alcalase 2.4 L (Novozymes North America Inc.) and 1 liter of DI water were added to the reactor. When temperature of the mixture closed to 38° C., pH was adjusted to 7.8 with 10 N NaOH. A solution of the racemic N-Boc-(1R,2S)/(1S,2R)-1-amino-2-vinylcyclopropane carboxylic acid ethyl ester (500 grams) in 5 liters DMSO was added to the reactor over a period of 1 hour via an addition funnel. The reaction temperature was then adjusted to 48° C. After 21 hours, enantio-excess of the ester reached 99.3%. Heating was stopped at 24 hours and the reaction was slowly cooled down to room temperature (about 25° C.) and stirred overnight. The pH of the reaction mixture was adjusted to 8.5 with 10 N NaOH and the mixture was extracted with MTBE (2×4 L). The combined MTBE extract was washed with 5% NaHCO$_3$ (3×400 mL) and water (3×400 mL), and concentrated to give enantiomerically pure N-Boc-(1R,2S)/-1-amino-2-vinylcyclopropane carboxylic acid ethyl ester as light yellow crystal (259 g; purity: 96.9% @ 210 nm, containing no acid; 100% ee).

Resolution E

10 L of 0.1 M sodium phosphate buffer (pH 8) was maintained at 40° C. in a 20 Liter jacked reactor, stirred at 360 rpm. 1.5 liters of Alcalase 2.4 L (Novozymes North America Inc.) was added to the reactor. When the temperature of the mixture closed to 38° C., the pH was adjusted to 8.0 with 10 N NaOH.

A solution of the racemic N-Boc-(1R,2S)/(1S,2R)-1-amino-2-vinylcyclopropane carboxylic acid ethyl ester (200 grams) in 2 liters DMSO was added to the reactor over a period of 1 hour via an addition funnel. The reaction temperature was then adjusted to 40° C. After 3 hours, the pH was adjusted to 8.0 with 10 N NaOH. After 21 hours, the reaction was cooled down to 25° C., the pH of the reaction mixture was adjusted to 8.5 with 10 N NaOH and the mixture was extracted with MTBE (2×5 L). The combined MTBE extract was washed with 5% NaHCO₃ (3×500 mL) and water (3×200 mL), and concentrated to give 110 gram of yellow oil. The oil was set at room temperature under house vacuum and gave enantiomerically pure N-Boc-(1R,2S)/-1-amino-2-vinylcyclopropane carboxylic acid ethyl ester as colorless long rod crystal (101 g; purity: 97.9% @ 210 nm, containing no acid; 100% ee).

The crystal structure enantiomerically pure N-Boc-(1R,2S)/-1-amino-2-vinylcyclopropane carboxylic acid ethyl ester has been characterized by single crystal analysis (X-ray NB#: 52795-093, refcode: 634592N1). The absolute configuration is not established for lack of a known chiral center or heavier atom(s). A chain structure along the crystallographic a-axis is formed via intermolecular hydrogen bonding between the amide group and the carbonyl oxygen atom (N . . . O 3.159 Å).

Structure of N-Boc-(1R,2S)-1-amino-2-vinylcyclopropane carboxylic acid ethyl ester:

Resolution F

5 L of 0.2 M sodium borate buffer (pH 9) was maintained at 45° C. in a 20 liter jacked reactor, and stirred at 400 rpm. Three liter of DI water and four liters of Savinase 16 L, type EX (Novozymes North America Inc.) were added to the reactor. When temperature of the mixture closed to 45° C., pH was adjusted to 8.5 with 10 N NaOH. A solution of the racemic N-Boc-(1R,2S)/(1S,2R)-1-amino-2-vinylcyclopropane carboxylic acid ethyl ester (200 grams) in 2 liters DMSO was added to the reactor over a period of 40 minutes, via an addition funnel. The reaction temperature was then adjusted to 48° C. After 2 hours, pH was adjusted to pH 9.0 with 10 N NaOH. At 18 hour, enantio-excess of the ester reached 72%, pH was adjusted to 9.0 with 10 N NaOH. At 24 hours, temperature was lowered to 35° C. At 42 hours, the temperature was raised to 48° C. and the pH was adjusted to 9.0 with 10 N NaOH. Heating was stopped at 48 hours and the reaction was slowly cooled down to room temperature (about 25° C.) and stirred overnight. At 66 hour, pH of the reaction mixture was 8.6. The mixture was extracted with MTBE (2×4 L). The combined MTBE extract was washed with 5% NaHCO₃ (6×300 mL) and water (3×300 mL), and concentrated to give enantiomerically pure N-Boc-(1R,2S)/-1-amino-2-vinylcyclopropane carboxylic acid ethyl ester as light yellow crystal (101A g; purity: 95.9% @ 210 nm, containing no acid; 98.6% ee).

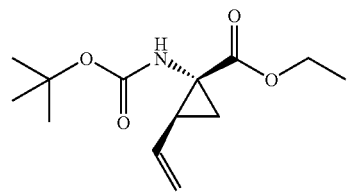

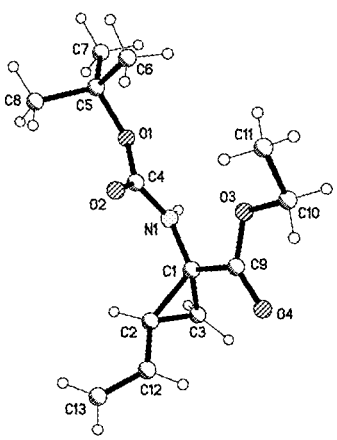

Crystal Data:

Chemical formula: C13H21N1O4
Crystal system: Orthorhombic
Space Group: $P2_12_12_1$
a = 5.2902(1) Å    α = 90°
b = 13.8946(2) Å   β = 90°
c = 19.9768(3) Å   γ = 90°
V = 1468.40(4) Å³
Z = 4         $d_x$ = 1.155 g cm⁻³
No. of reflections for lattice parameters: 6817
θ range for lattice parameters (°): 2.2-65.2
Absorption coefficient (mn⁻¹): 0.700

Experimental:

Crystallization
Crystal source: MTBE
Crystal description: Colorless rod
Crystal size (mm): 0.12 × 0.26 × 0.30
Data Collection
Temperature (K): 293
$θ_{max}$ (°): 65.2 (Cu Kα)
No. of reflections measured: 7518
No. of independent reflections: 2390 ($R_{int}$ = 0.0776)
No. of observed reflections (I ≥ 2σ: 2284
Absorption correction ($T_{min}$-$T_{max}$): 0.688-1.000

10. Preparation of chiral (1R,2S)-1-amino-2-vinylcyclopropane carboxylic acid ethyl ester hydrochloride

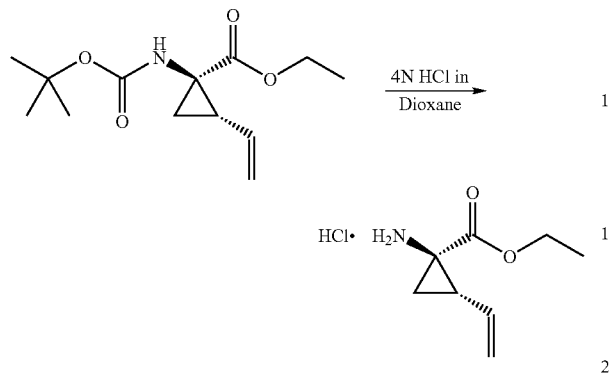

(1R,2 S) N-Boc-1-amino-2-vinylcyclopropanecarboxylic acid ethyl ester (8.5 g, 33.3 mmol) was stirred under a nitrogen atmosphere with 200 mL of 4N HCl/dioxane (Aldrich) at room temperature for 3 hours. The solvent was removed under reduced pressure keeping the temperature below 40° C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69-1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69-5.81 (m, 1H). MS m/z 156 (M$^+$+1).

11. Preparation of N-Boc-(1R,2S)-1-amino-2-cyclopropylcyclopropane carboxylic acid ethyl ester

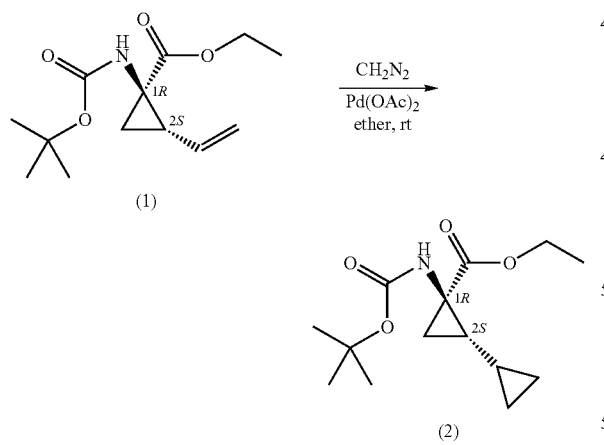

A solution of N-Boc-(1R,2S)-1-amino-2-vinylcyclopropane carboxylic acid (255 mg, 1.0 mmol) in diethyl ether (10 mL) was treated with palladium acetate (5 mg, 0.022 mmol). The orange/red solution was placed under a nitrogen atmosphere. An excess of diazomethane in diethyl ether was added dropwise over the course of 1 hour. The resulting solution was stirred at room temperature for 18 hours. The excess diazomethane was removed using a stream of nitrogen and the resulting solution was concentrated by rotary evaporation to give the crude product. Flash chromatography (10% ethyl acetate/hexane) provided 210 mg (78%) of (1R,2S)—N-Boc-1-amino-2-cyclopropylcyclopropane carboxylic acid ethyl ester as a colorless oil. MS m/z 270 (M$^+$+H).

Preparation of P1'-P1 Intermediates

12. Preparation of P1P1'

Scheme 1

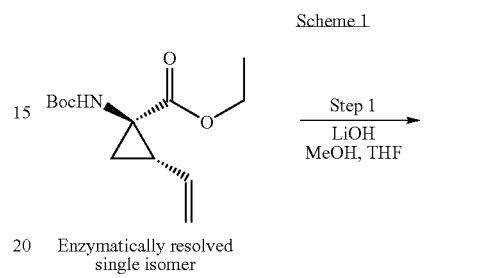

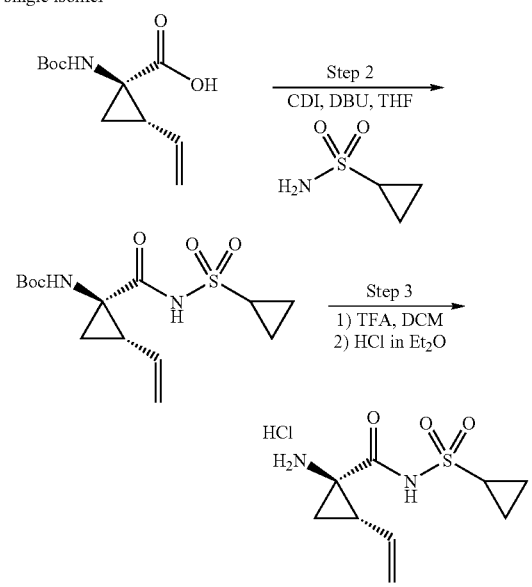

Step 1

To a solution of 1(R)-tert-butoxycarbonylamino-2(S)-vinyl-cyclopropanecarboxylic acid ethyl ester (3.28 g, 13.2 mmol) in THF (7 mL) and methanol (7 mL) was added a suspension of LiOH (1.27 g, 53.0 mmol) in water (14 mL). The mixture was stirred overnight at room temperature. To the mixture was added 1.0M NaOH (15 mL), water (20 mL) and ethyl acetate (20 mL). The mixture was shaken, the phases were separated, and the organic phase was again extracted with 20 mL 0.5M NaOH. The combined aqueous phases were acidified with 1.0M HCl until pH=4 and extracted with ethyl acetate (3×40 mL). The combined organic extracts were washed with brine, dried (MgSO$_4$), and filtered to provide the desired product as a white solid (2.62 g, 87%). $^1$H NMR: (DMSO-d$_6$) δ1.22-1.26 (m, 1H), 1.37 (s, 9H), 1.50-1.52 (m, 1H), 2.05 (q, J=9 Hz, 1H), 5.04 (d, J=10 Hz, 1H), 5.22 (d, J=17 Hz, 1H), 5.64-5.71 (m, 1H), 7.18, 7.53 (s, NH (rotamers), 12.4 (br s, 1H)); LC-MS MS m/z 228 (M$^+$+H).

Step 2

A solution of the product of Step 1 (2.62 g, 11.5 mmol) and CDI (2.43 g, 15.0 mmol) in THF (40 mL) was heated at reflux for 50 minutes under nitrogen. The solution was cooled to room temperature and transferred by cannula to a solution of cyclopropylsulfonamide (1.82 g, 15.0 mmol) in THF (10 mL). To the resulting solution was added DBU (2.40 mL, 16.1 mmol) and stirring was continued for 20 hours. The mixture was quenched with 1.0M HCl to pH=1, and THF was evaporated in vacuo. The suspension was extracted with ethyl acetate (2×50 mL) and the organic extracts were combined and dried ($Na_2SO_4$). Filtration, concentration, and purification by recrystallization from hexanes-ethyl acetate (1:1) provided the desired product (2.4 g) as a white solid. The mother liquor was purified by a Biotage 40S column (eluted 9% acetone in dichloromethane) to give a second batch of the desired product (1.1 g). Both batches were combined (total yield 92%). $^1$H NMR: (DMSO-$d_6$) δ 0.96-1.10 (m, 4H), 1.22 (dd, J=5.5, 9.5 Hz, 1H), 1.39 (s, 9H), 1.70 (t, J=5.5 Hz, 1H), 2.19-2.24 (m, 1H), 2.90 (m, 1H), 5.08 (d, J=10 Hz, 1H), 5.23 (d, J=17 Hz, 1H), 5.45 (m, 1H), 6.85, 7.22 (s, NH (rotamers)); LC-MS, MS m/z 331 ($M^+$+H).

Step 3

A solution of the product of Step 2 (3.5 g, 10.6 mmol) in dichloromethane (35 mL) and TFA (32 mL) was stirred at room temperature for 1.5 hours. The volatiles were removed in vacuo and the residue suspended in 1.0M HCl in diethyl ether (20 mL) and concentrated in vacuo. This procedure was repeated once. The resulting mixture was triturated with pentane and filtered to give the title compound as a hygroscopic, off-white solid (2.60 g, 92%). $^1$H NMR (DMSO-$d_6$) δ 1.01-1.15 (m, 4H), 1.69-1.73 (m, 1H), 1.99-2.02 (m, 1H), 2.38 (q, J=9 Hz, 1H), 2.92-2.97 (m, 1H), 5.20 (d, J=11 Hz, 1H), 5.33 (d, J=17 Hz, 1H), 5.52-5.59 (m, 1H), 9.17 (br s, 3H); LC-MS, MS m/z 231 ($M^+$+H).

13. Preparation of P1-P1' Sulfamide Derivative

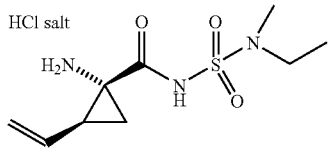

To a solution of (1R,2S) 1-tert-butoxycarbonylamino-2-vinyl-cyclopropanecarboxylic acid (217 mg, 1.194 mmol) in THF (5 mL), was added CDI (290 mg, 1.791 mmol) and the reaction mixture was heated to reflux for 45 minutes. In another round-bottomed flask, LiHMDS (1.0M solution in hexanes, 2.4 mL, 2.4 mmol) was added to a solution of N-ethylmethylsulfamide (330 mg, 2.388 mmol) in THF (5 mL) and the reaction mixture was stirred at room temperature for 1 hour. The two reaction mixtures were combined and stirred at room temperature for 2 hours. Water was added to quench the reaction and the reaction solution was extracted with ethyl acetate. The organic layer was separated and dried over $MgSO_4$. Filtration and concentration gave crude product which was purified by preparative HPLC to provide the desired N-Boc protected N-acylsulfamide. The Boc protecting group was then removed as the compound was dissolved in 4N HCl solution in dioxane (2 mL) and stirred at room temperature for 4 hours. Concentration provided a brownish oil as the HCl salt. (112 mg, 33% yield). $^1$H NMR (400 Mz, $CD_3OD$) δ1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 minutes.), MS m/z 270 ($M+Na^+$).

Example 3

Preparation of Example 3

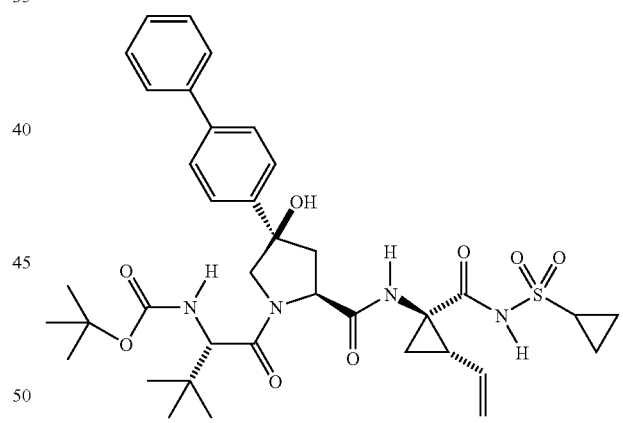

Example 3

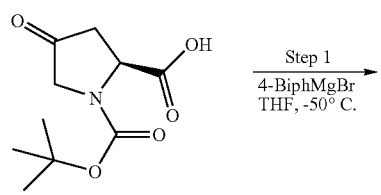

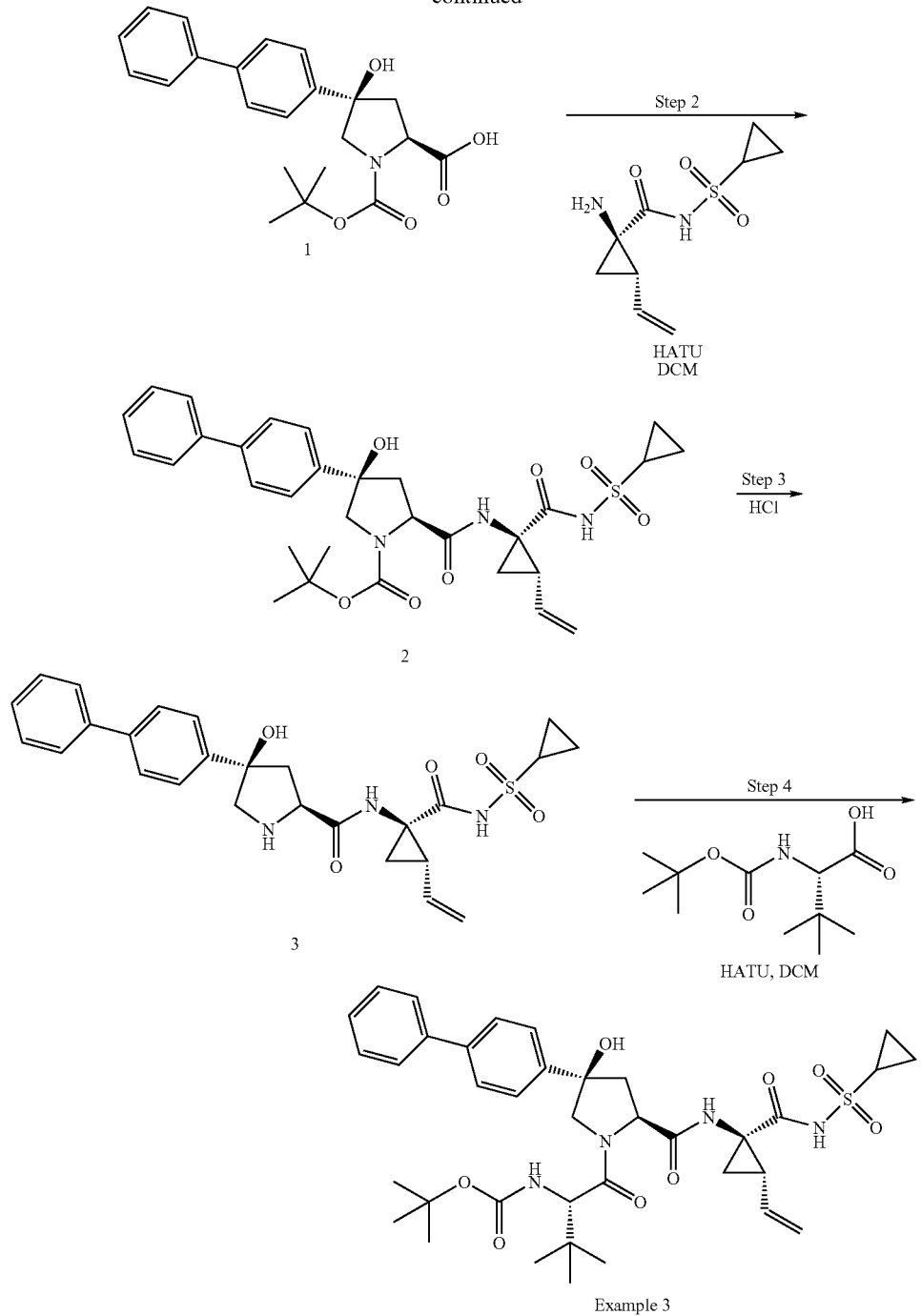

Example 3

Step 1

To a solution of (S)-1-(tert-butoxycarbonyl)-4-oxopyrrolidine-2-carboxylic acid (460 mg, 2.0 mmol) in THF (10 mL) was added 4-biphenylmagnesium bromide (0.5 M THF, 16.0 mL, 8.0 mmol) dropwise at −50° C. After stirring at this temperature for 4 hours, the mixture was quenched with 5% citric acid, extracted with ethyl acetate (50 mL). The organic layer was washed with brine, dried over MgSO₄, filtered, and concentrated. The residual solid was recrystallized from ethyl acetate:hexanes (15 mL : 15 mL) to yield intermediate 1 as a white solid (415 mg, 54%). ¹H NMR (CD₃OD) δ 1.49, 1.51 (d, 9H), 2.48-2.51 (m, 1H), 2.79-2.82 (m, 1H), 3.75-3.81 (m, 2H), 4.48-4.53 (m, 1H), 7.33-7.36 (m, 1H), 7.43-7.46 (m, 2H), 7.58-7.65 (m, 6H); MS m/z 384 (M⁺+H).

Step 2

To an iced mixture of intermediate 1 (383 mg, 1.0 mmol), cyclopropanesulfonic acid (1-(R)-amino-2-(S)-vinylcyclopropanecarbonyl)amide hydrochloride (293 mg, 1.1 mmol)

and HATU (570 mg, 1.5 mmol) in dichloromethane (10 mL) was added diisopropylethylamine (560 mg, 5.0 mmol). The formed solution was allowed to warm up to the ambient temperature for 4 hours and the volatiles were removed in vacuo. The residue was triturated with ethyl acetate (100 mL) and filtered. The filtrate was washed with 5% citric acid (50 mL, ×2) and brine, dried over MgSO$_4$, filtered, and concentrated. The residue was triturated with methanol (4 mL) to yield 314 mg (53%) of the desired product, intermediate 2. MS m/z 596 (M$^+$+H).

Step 3

To an iced suspension of intermediate 2 (150 mg, 0.25 mmol) in 1,4-dioxane (1 mL) was added HCl (4M dioxane, 5 mL). The formed solution was stirred at the ambient temperature for 2 hours and the volatiles were removed in vacuo and dried under high vacuum overnight. The product was used directly in the next step. MS m/z 496 (M$^+$+H).

Step 4

To an iced suspension of intermediate 3 (134 mg, 0.25 mmol) in dichloromethane (2.5 mL) was added diisopropylethylamine (560 mg, 5.0 mmol) dropwise. To this formed solution was added HATU (144 mg, 0.38 mmol) and (S)-2-(tert-butoxycarbonyl)-3,3-dimethylbutanoic acid (64 mg, 0.28 mmol). The final mixture was allowed to warm up to the ambient temperature overnight and the volatiles were removed in vacuo. The residue was triturated with ethyl acetate (10 mL) and filtered. The filtrate was washed with 5% citric acid (10 mL, ×2) and brine, dried over MgSO$_4$, filtered, and concentrated. The residue was purified by preparative HPLC to yield 16 mg (9%) of the desired product, Example 4 as a white solid. $^1$H NMR (CD$_3$OD) δ 1.08-1.13 (m, 11H), 1.27-1.29 (m, 2H), 1.47-1.53 (m, 10H), 1.89-1.93 (m, 1H), 2.26-2.32 (m, 2H), 2.68-2.71 (m, 1H), 2.97-2.99 (m, 1H), 4.05-4.12 (m, 1H), 4.34-4.37 (m, 2H), 4.45-4.47 (m, 1H), 5.15 (d, J=12 Hz, 1H), 5.33 (d, J=18.5 Hz, 1H), 5.77-5.82 (m, 1H), 7.36-7.37 (m, 1H), 7.44-7.47 (m, 2H), 7.62-7.67 (m, 6H); MS m/z 709 (M$^+$+H).

Example 4

Preparation of Example 4

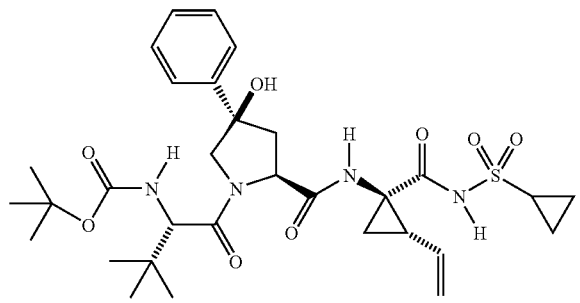

Example 4

Step 1

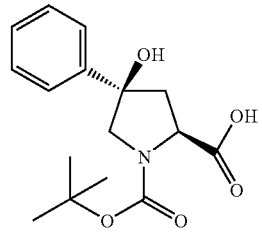

This product was prepared by the same procedure as described in Example 3, Step 1, except using phenylmagnesium bromide instead. $^1$H NMR (DMSO-d$_6$) δ 1.36-1.41 (m, 9H), 2.25-2.28 (m, 1H), 2.60-2.64 (m, 1H), 3.56-3.66 (m, 2H), 4.27-4.29 (m, 1H), 5.50 (s, 1H), 7.25-7.36 (m, 3H), 7.46-7.48 (m, 2H), 12.40 (br, 1H); MS m/z 308 (M$^+$+H).

Step 2

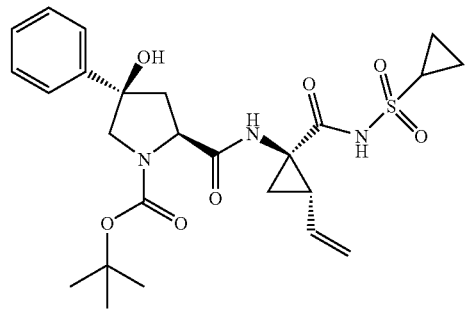

This product was prepared by the same procedure as described in Example 3, Step 2, except using the product of Example 4, Step 1 instead. MS m/z 520 (M$^+$+H).

Step 3

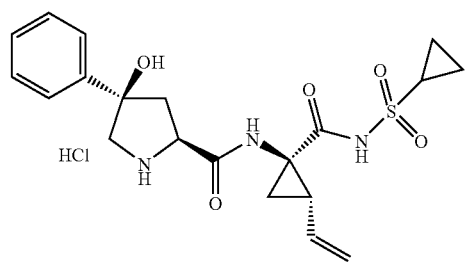

This product was prepared by the same procedure as described in Example 3, Step 3, except using the product of Example 4, Step 2 instead. MS m/z 420 (M$^+$+H).

Step 4

Example 4 was prepared by the same procedure as described in Example 3, Step 4, except using the product of Example 4, Step 3 instead. $^1$H NMR (CD$_3$OD) δ 1.08-1.12 (m, 11H), 1.27-1.28 (m, 2H), 1.48-1.52 (m, 10H), 1.89-1.90 (m, 1H), 2.26-2.32 (m, 2H), 2.68-2.71 (m, 1H), 2.97-2.99 (m, 1H), 4.05-4.09 (m, 1H), 4.34-4.35 (m, 2H), 4.45-4.47 (m, 1H), 5.14 (d, J=12 Hz, 1H), 5.34 (d, J=18.5 Hz, 1H), 5.77-5.82 (m, 1H), 7.31-7.33 (m, 1H), 7.37-7.40 (m, 2H), 7.57-7.59 (m, 2H); MS m/z 633 (M$^+$+H).

Example 5

Preparation of Example 5

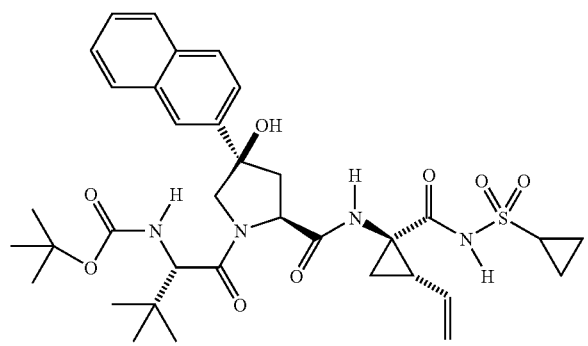

Example 5

Step 1

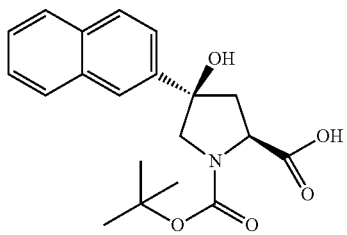

This product was prepared by the same procedure as described in Example 3, Step 1, except using 2-naphthylmagnesium bromide instead. $^1$H NMR (CD$_3$OD) δ 1.50, 1.52 (d, 9H), 2.54-2.56 (m, 1H), 2.89-2.91 (m, 1H), 3.84-3.87 (m, 2H), 4.51-4.53 (m, 1H), 7.45-7.52 (m, 2H), 7.62-7.64 (m, 1H), 7.85-7.94 (m, 3H), 7.99 (s, 1H); MS m/z 358 (M$^+$+H).

Step 2

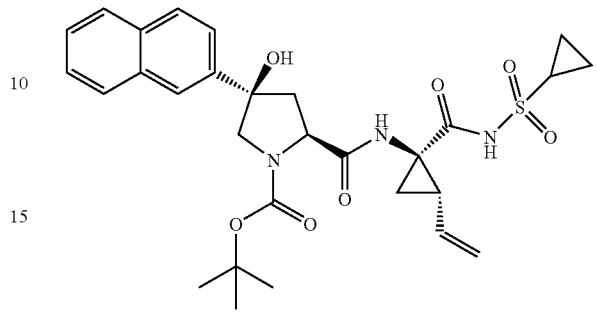

This product was prepared by the same procedure as described in Example 3, Step 2, except using the product of Example 5, Step 1 instead. MS m/z 570 (M$^+$+H).

Step 3

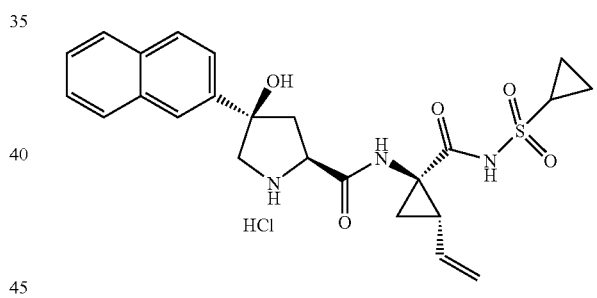

This product was prepared by the same procedure as described in Example 3, Step 3, except using the product of Example 5, Step 2 instead. MS m/z 470 (M$^+$+H).

Step 4

Example 5 was prepared by the same procedure as described in Example 3, Step 4, except using the product of Example 5, Step 3 instead. $^1$H NMR (CD$_3$OD) δ 1.05-1.12 (m, 1H), 1.28-1.29 (m, 2H), 1.48-1.53 (m, 10H), 1.91-1.92 (m, 1H), 2.25-2.40 (m, 2H), 2.75-2.79 (m, 1H), 2.97-3.00 (m, 1H), 4.13-4.16 (m, 1H), 4.38-4.47 (m, 2H), 5.14 (d, J=12 Hz, 1H), 5.33 (d, J=18.5 Hz, 1H), 5.77-5.82 (m, 1H), 7.49-7.51 (m, 2H), 7.70-7.73 (m, 1H), 7.86-7.92 (m, 3H), 8.04 (s, 1H); MS m/z 683 (M$^+$+H).

Example 6

Preparation of Example 6

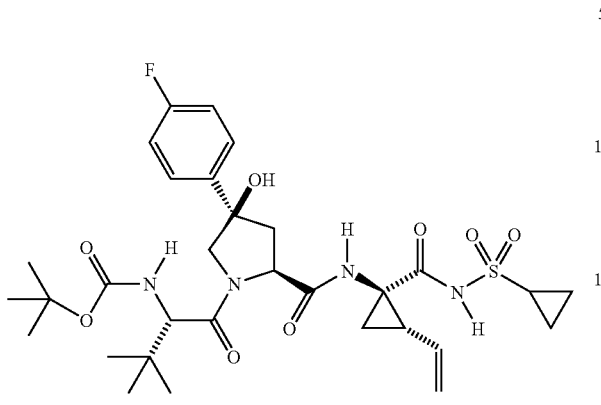

Example 6

Step 1

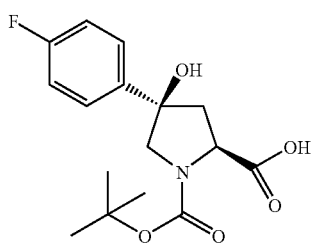

This product was prepared by the same procedure as described in Example 3, Step 1, except using 4-fluorophenyl-magnesium bromide instead. $^1$H NMR (CD$_3$OD) δ 1.48, 1.50 (d, 9H), 2.44-2.47 (m, 1H), 2.74-2.95 (m, 2H), 3.69-3.76 (m, 2H), 4.45-4.53 (m, 1H), 7.08-7.12 (m, 2H), 7.52-7.54 (m, 2H); MS m/z 326 (M$^+$+H).

Step 2

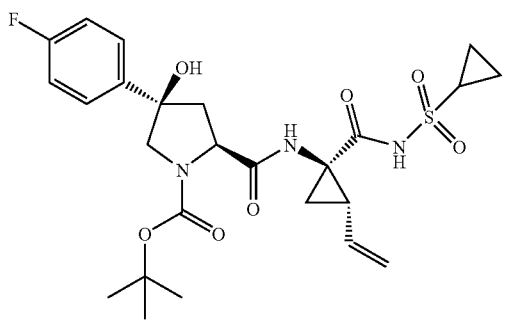

This product was prepared by the same procedure as described in Example 3, Step 2, except using the product of Example 6, Step 1 instead. MS m/z 538 (M$^+$+H).

Step 3

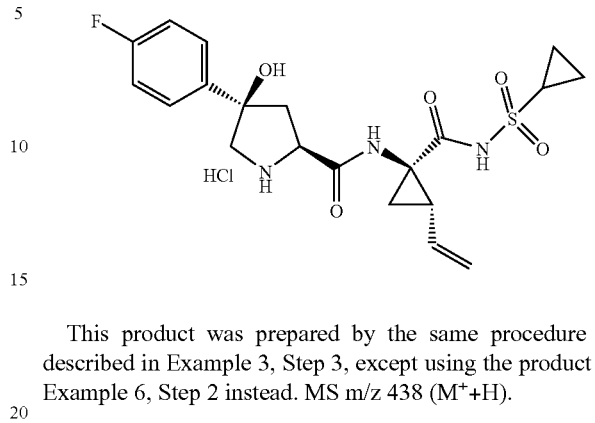

This product was prepared by the same procedure as described in Example 3, Step 3, except using the product of Example 6, Step 2 instead. MS m/z 438 (M$^+$+H).

Step 4

Example 6 was prepared by the same procedure as described in Example 3, Step 4, except using the product of Example 6, Step 3 instead. $^1$H NMR (CD$_3$OD) δ 1.02-1.12 (m, 1H), 1.26-1.28 (m, 2H), 1.47-1.52 (m, 10H), 1.89-1.90 (m, 1H), 2.25-2.28 (m, 2H), 2.55-2.65 (m, 1H), 2.92-2.99 (m, 1H), 4.06-4.08 (m, 1H), 4.25-4.33 (m, 2H), 4.41-4.49 (m, 1H), 5.15 (d, J=12 Hz, 1H), 5.32 (d, J=18.5 Hz, 1H), 5.77-5.82 (m, 1H), 7.09-7.12 (m, 2H), 7.60-7.63 (m, 2H); MS m/z 651 (M$^+$+H).

Example 7

Preparation of Example 7

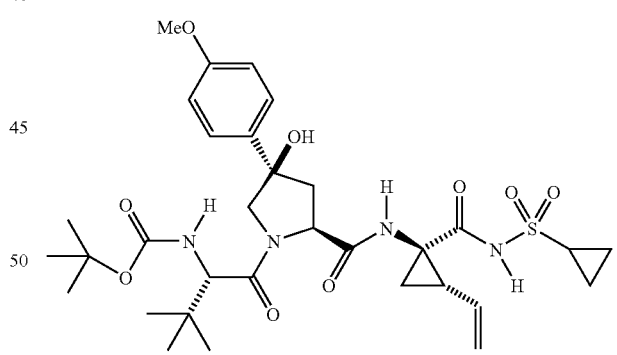

Example 7

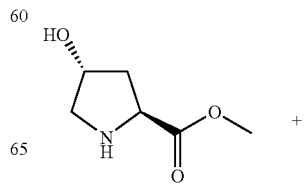 +

79

-continued

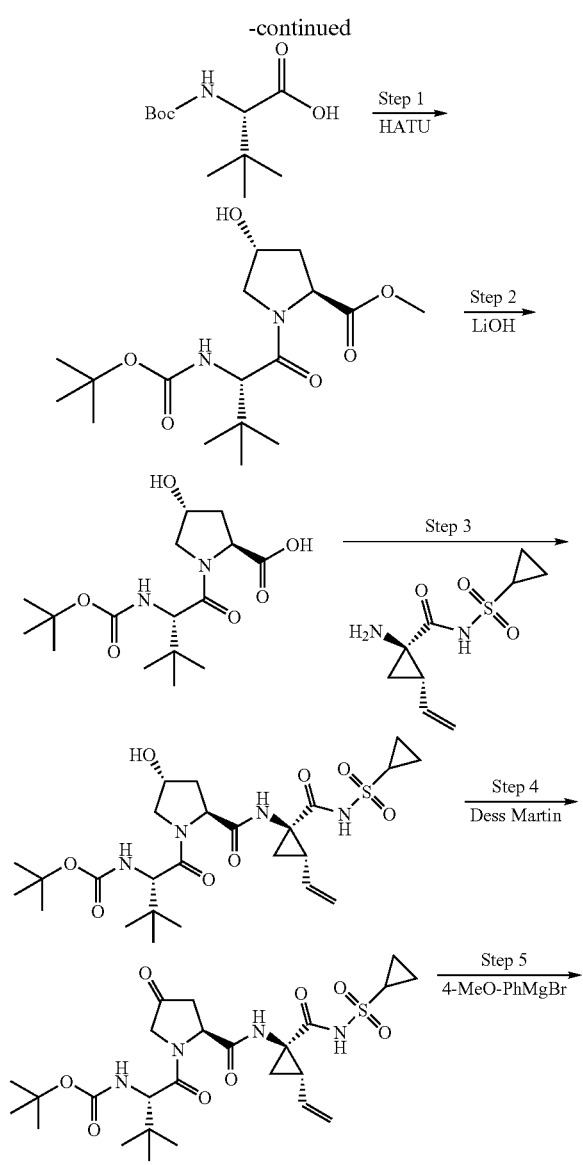

Example 7

Step 1

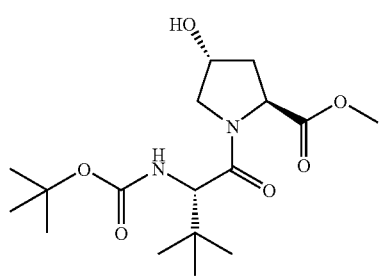

To a slurry of (2S,4R)-methyl 4-hydroxypyrrolidine-2-carboxylate HCl salt (5.45 g, 30.0 mmol), (S)-2-(tert-butoxycarbonyl)-3,3-dimethylbutanoic acid (6.93 g, 30.0 mmol), and HATU (17.1 g, 45.0 mmol) in dichloromethane (100 mL) at 0° C. was added diisopropylethylamine (16.8 g, 150 mmol) dropwise. The formed solution was stirred at room temperature overnight, washed with iced 5% citric acid and 1M NaOH (aq) twice, and then with brine, dried over MgSO$_4$, and filtered. The filtrate was concentrated in vacuo to provide 10.75 g (100%) as light brownish foam. $^1$H NMR (CD$_3$OD) δ 1.04 (s, 9H), 1.46 (s, 9H), 2.01-2.06 (m, 1H), 2.27-2.29 (m, 1H), 3.73 (s, 3H), 3.77-3.87 (m, 2H), 4.31 (s, 1H), 4.49 (br, 1H), 4.56 (t, J=8.5 Hz, 1H).

Step 2

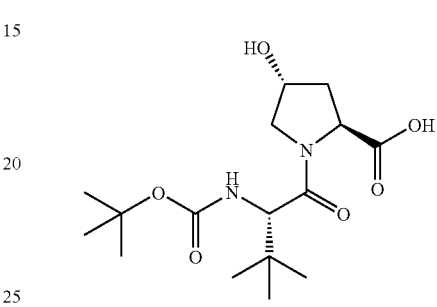

To a solution of the product of Example 7, Step 1 (10.75 g, 30.0 mmol) in THF (100 mL) and methanol (100 mL) was added LiOH monohydrate (6.30 g, 150 mmol) solution in water (100 mL). The final solution was stirred at room temperature overnight. Removed the volatiles in vacuo. The residue was acidified with 1M HCl (aq) to pH 2. Extracted with ethyl acetate (100 mL). The organic layer was washed with 5% citric acid, and brine, dried over MgSO$_4$, and filtered. The filtrate was concentrated in vacuo to provide 8.95 g (87%) of the desired product as off-white foam. $^1$H NMR (CD$_3$OD) δ 1.05 (s, 9H), 1.45 (s, 9H), 2.03-2.06 (m, 1H), 2.32-2.36 (m, 1H), 3.79-3.86 (m, 2H), 4.32 (br, 1H), 4.49 (br, 1H), 4.54 (t, J=8.5 Hz, 1H).

Step 3

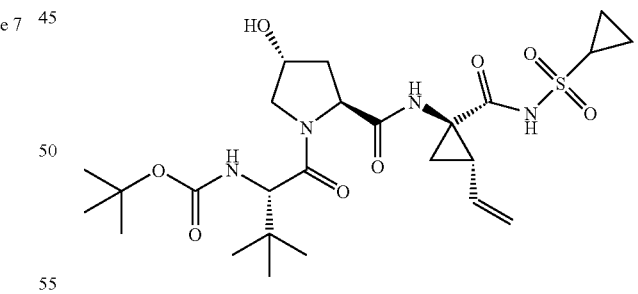

To a solution of the product from Example 7, Step 2 (1.95 g, 5.68 mmol) in ethyl acetate (150 mL) at 0° C. was added (1R,2S)-1-amino-N-(cyclopropylsulfonyl)-2-vinylcyclopropanecarboxamide HCl salt (1.51 g, 5.68 mmol). The mixture was stirred at this temperature for 5 minutes before addition of diisopropylethylamine (1.91 g, 17.0 mmol) dropwise. The formed clear solution was stirred at 0° C. for another 5 minutes before addition of EDC (1.41 g, 7.38 mmol) and HOBt (0.77 g, 5.68 mmol). The final slurry was stirred at room temperature overnight. The formed clear solution was washed with iced 5% citric acid twice, saturated sodium citrate (aq)

and brine respectively, dried over MgSO$_4$, and filtered. The filtrate was concentrated in vacuo, purified by flash column, eluting with 1:1 hexane-acetone to yield 2.50 g (79%) of the desired product as white foam. $^1$H NMR (CD$_3$OD) δ 1.00-1.10 (m, 1H), 1.24-1.28 (m, 2H), 1.41-1.46 (m, 10H), 1.86-1.91 (m, 1H), 2.00-2.04 (m, 1H), 2.12-2.28 (m, 1H), 2.92-2.99 (m, 1H), 3.80-3.95 (m, 2H), 4.30-4.40 (m, 2H), 4.51 (br, 1H), 5.14 (d, J=12 Hz, 1H), 5.35 (d, J=18.5 Hz, 1H), 5.77-5.82 (m, 1H); MS m/z 557 (M$^+$+H).

Step 4

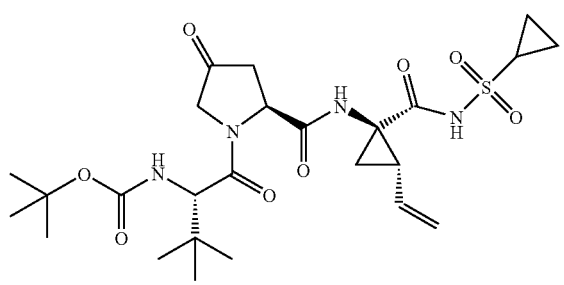

To a solution of Dess Martin reagent (940 mg, 2.2 mmol) in dichloromethane (20 mL) was added the product of Example 7, Step 3 (556 mg, 1.0 mmol). The solution was stirred at room temperature for 4 hours and concentrated in vacuo. The residue was triturated with hot ethyl acetate (10 mL) and filtered through diatomaeous earth (Celite®). The filtrate was concentrated in vacuo. The residue was purified by flash column, eluting with 1:1 hexane-acetone to yield 550 mg (99%) of the desired product as white foam. $^1$H NMR (CD$_3$OD) δ 1.09-1.14 (m, 11H), 1.25-1.28 (m, 2H), 1.43-1.46 (m, 10H), 1.88-1.91 (m, 1H), 2.22-2.28 (m, 1H), 2.51-2.60 (m, 1H), 2.92-2.96 (m, 1H), 4.17-4.34 (m, 2H), 4.77-4.80 (m, 1H), 5.16 (d, J=12 Hz, 1H), 5.33 (d, J=18.5 Hz, 1H), 5.72-5.82 (m, 1H); MS m/z 555 (M$^+$+H).

Step 5

To a solution of the product of Example 7, Step 4 (23 mg, 0.05 mmol) in THF (0.5 mL) at −50° C. was added 4-methoxyphenylmagnesium bromide (0.5 mL, 0.5M in THF, 0.25 mmol) dropwise. The formed solution was stirred at this temperature for 2 hours and quenched with ammonium chloride (aq), then extracted with ethyl acetate. The organic layer was washed with brine, dried over MgSO$_4$, filtered, and concentrated. The residue was purified by preparative HPLC to yield 4.5 mg (14%) of Example 7 as a white solid. $^1$H NMR (CD$_3$OD) δ 1.09-1.12 (m, 11H), 1.26-1.28 (m, 2H), 1.46-1.52 (m, 10H), 1.89-1.91 (m, 1H), 2.25-2.28 (m, 2H), 2.58-2.65 (m, 1H), 2.92-2.99 (m, 1H), 3.81 (s, 3H), 4.04-4.08 (m, 1H), 4.25-4.35 (m, 2H), 4.41-4.49 (m, 1H), 5.15 (d, J=12 Hz, 1H), 5.32 (d, J=18.5 Hz, 1H), 5.74-5.82 (m, 1H), 6.92-6.94 (m, 2H), 7.48-7.50 (m, 2H); MS m/z 663 (M$^+$+H).

Example 8

Preparation of Example 8

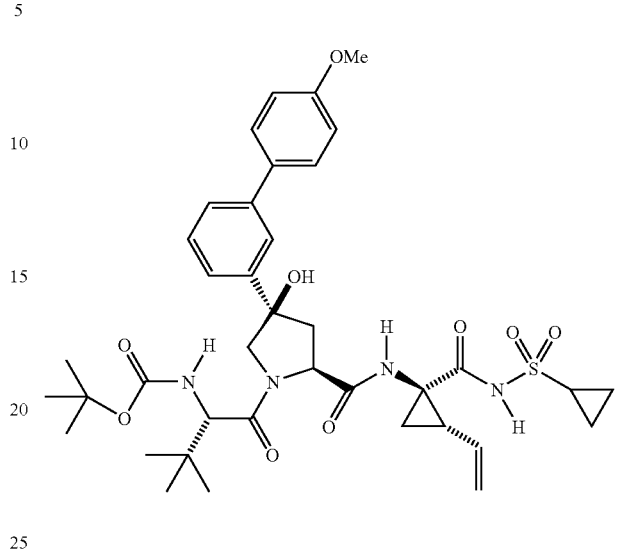

Example 8

Example 8 was prepared by the same procedure as described in Example 7, Step 5, except using 4'-methoxy-3-biphenylmagnesium bromide instead. $^1$H NMR (CD$_3$OD) δ 1.02-1.10 (m, 11H), 1.29-1.31 (m, 2H), 1.40-1.50 (m, 10H), 1.90-1.92 (m, 1H), 2.25-2.27 (m, 2H), 2.68-2.69 (m, 1H), 2.92-2.98 (m, 1H), 3.84 (s, 3H), 4.10-4.15 (m, 1H), 4.35-4.52 (m, 2H), 5.15 (d, J=12 Hz, 1H), 5.32 (d, J=18.5 Hz, 1H), 5.75-5.82 (m, 1H), 7.00-7.03 (m, 3H), 7.40-7.60 (m, 5H); MS m/z 739 (M$^+$+H).

Example 9

Preparation of Example 9

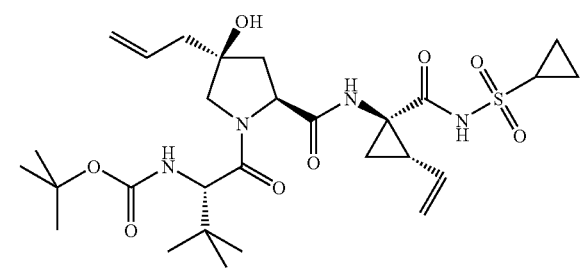

Example 9

To a solution of tert-butyl (S)-1-{(S)-2-{[(1R,2S)-1-(cyclopropylsulfonylcarbamoyl)-2-vinylcyclopropyl]carbamoyl}-4-oxopyrrolidin-1-yl}-3,3-dimethyl-1-oxobutan-2-ylcarbamate (77 mg, 0.14 mmol), prepared as described in Example 7, in THF (5 mL) at −78° C. was added allylmagnesium bromide (1.0M in diethyl ether, 0.7 mL, 0.7 mmol). The reaction mixture was warmed to room temperature and stirred overnight. The reaction was quenched with saturated aqueous NH$_4$Cl. The mixture was extracted with ethyl acetate, dried over MgSO₄, filtered, and concentrated in vacuo. The crude product was purified by flash column chromatography on silica gel eluting with 2:1 hexanes/acetone to give the title product (50 mg, 60%). $^1$H NMR (400 MHz, CD$_3$OD) δ 0.92-0.96 (m, 2H), 0.93-1.09 (m, 10H), 1.19-1.25 (m, 2H), 1.38-1.48 (m, 10H), 1.83-1.94 (m, 2H), 2.18-2.31 (m, 2H), 2.31-2.46 (m, 2H), 2.88-2.96 (m, 1H), 3.70 (d, J=9.82 Hz, 1H), 3.81 (d, J=10.32 Hz, 1H), 4.22 (d, J=9.32 Hz, 1H), 4.32 (dd, J=9.06, 4.78 Hz, 1H), 5.09-5.20 (m, 3H), 5.30 (dd, J=17.25, 1.38 Hz, 1H), 5.69-5.80 (m, 1H), 5.87-5.99 (m, 1H), 6.69 (d, J=9.06 Hz, 1H); MS m/z 619 (M+Na)$^+$.

General Procedure for Preparation of Examples 10-25

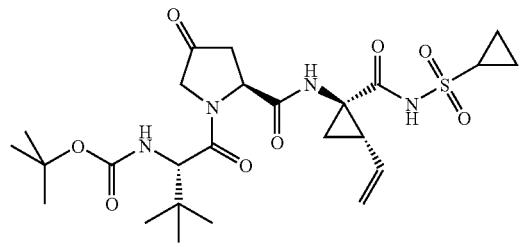

+

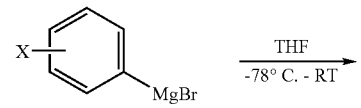

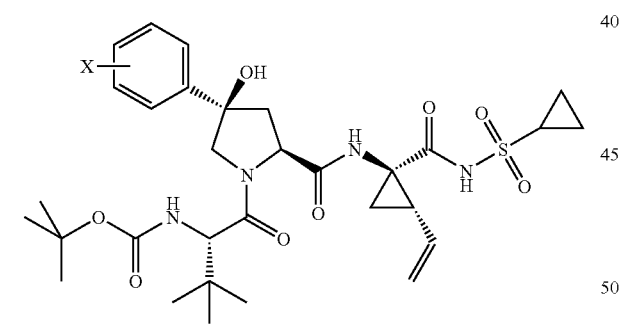

To a solution of tert-butyl (S)-1-{(S)-2-{[(1R,2S)-1-(cyclopropylsulfonylcarbamoyl)-2-vinylcyclopropyl]carbamoyl}-4-oxopyrrolidin-1-yl}-3,3-dimethyl-1-oxobutan-2-ylcarbamate (83 mg, 0.15 mmol) in THF (1-5 mL) at −78° C. was added the Grignard reagent (0.75-0.90 mmol). The reaction mixture was warmed to room temperature and stirred for 1-3 hours. The reaction was quenched with saturated aqueous NH₄Cl (1 mL). The mixture was neutralized with 1N HCl, extracted with ethyl acetate (2×20 mL), dried over MgSO₄, filtered, and concentrated in vacuo. The crude product was purified by preparative HPLC to give the desired product.

Example 10

Preparation of Example 10

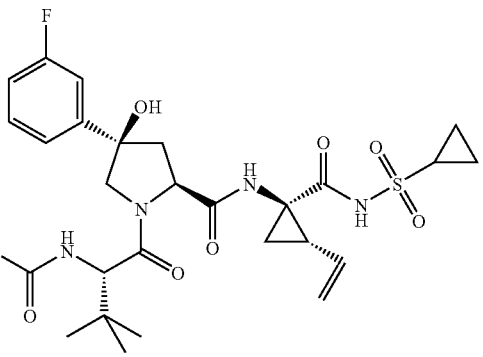

Example 10

Example 10 was prepared as described in the general procedure using (3-fluorophenyl) magnesium bromide (1.0M in THF, 0.75 mL, 0.75 mmol) and 5 mg (6%) of product was obtained. $^1$H NMR (400 MHz, CD$_3$OD) δ 0.98-1.01 (m, 2H), 1.03-1.11 (m, 10H), 1.21-1.27 (m, 2H), 1.37-1.51 (m, 10H), 1.87 (dd, J=8.18, 5.41 Hz, 1H), 2.18-2.28 (m, 2H), 2.56-2.64 (m, 1H), 2.90-2.99 (m, 1H), 4.03 (d, J=10.83 Hz, 1H), 4.24 (d, J=10.58 Hz, 1H), 4.28 (s, 1H), 4.43 (dd, J=9.06, 4.03 Hz, 1H), 5.12 (dd, J=10.45, 1.64 Hz, 1H), 5.30 (dd, J=17.12, 1.51 Hz, 1H), 5.70-5.82 (m, 1H), 6.99-7.07 (m, 1H), 7.30-7.41 (m, 3H); MS m/z 651 (M+H)$^+$.

Example 11

Preparation of Example 11

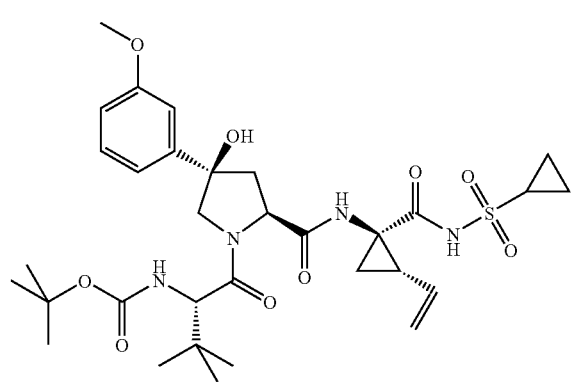

Example 11

Example 11 was prepared as described in the general procedure using (3-methoxyphenyl) magnesium bromide (1.0M in THF, 0.75 mL, 0.75 mmol) and 7 mg (7%) of product was obtained. $^1$H NMR (400 MHz, CD$_3$OD) δ 0.98-1.01 (m, 2H), 1.03-1.12 (m, 10H), 1.20-1.27 (m, 2H), 1.42-1.47 (m, 10H), 1.87 (dd, J=8.18, 5.41 Hz, 1H), 2.17-2.29 (m, 2H), 2.55-2.64 (m, 1H), 2.90-3.00 (m, 1H), 3.79 (s, 3H), 3.98-4.06 (m, 1H), 4.21-4.33 (m, 2H), 4.43 (dd, J=9.19, 3.90 Hz, 1H), 5.12 (dd, J=10.45, 1.64 Hz, 1H), 5.29 (dd, J=17.12, 1.51 Hz, 1H), 5.69-5.82 (m, 1H), 6.85 (dd, J=8.06, 2.01 Hz, 1H), 7.08 (d, J=7.81 Hz, 1H), 7.14 (s, 1H), 7.23-7.30 (m, 1H); MS m/z 663 (M+H)⁺.

Example 12

Preparation of Example 12

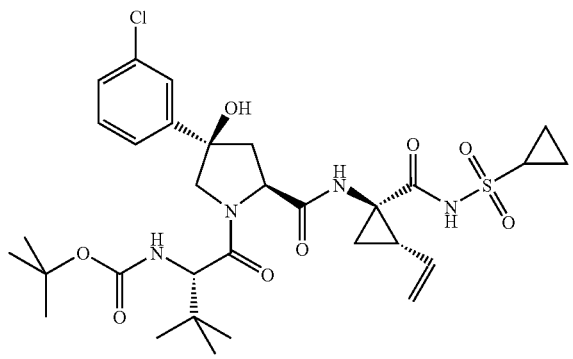

Example 12

Example 12 was prepared as described in the general procedure using (3-chlorophenyl) magnesium bromide (0.5M in THF, 1.8 mL, 0.90 mmol) and 5 mg (5%) of product was obtained. ¹H NMR (400 MHz, CD₃OD) δ 0.98-1.01 (m, 2H), 1.03-1.11 (m, 10H), 1.22-1.27 (m, 2H), 1.41-1.50 (m, 10H), 1.87 (dd, J=8.18, 5.41 Hz, 1H), 2.19-2.28 (m, 2H), 2.56-2.64 (m, 1H), 2.90-2.98 (m, 1H), 4.04 (d, J=10.58 Hz, 1H), 4.22 (d, J=10.83 Hz, 1H), 4.27 (s, 1H), 4.44 (dd, J=9.19, 3.90 Hz, 1H), 5.12 (dd, J=10.32, 1.51 Hz, 1H), 5.30 (dd, J=17.12, 1.51 Hz, 1H), 5.70-5.81 (m, 1H), 7.28-7.37 (m, 2H), 7.47 (t, J=7.68 Hz, 1H), 7.61 (s, 1H)); MS m/z 689 (M+Na)⁺.

Example 13

Preparation of Example 13

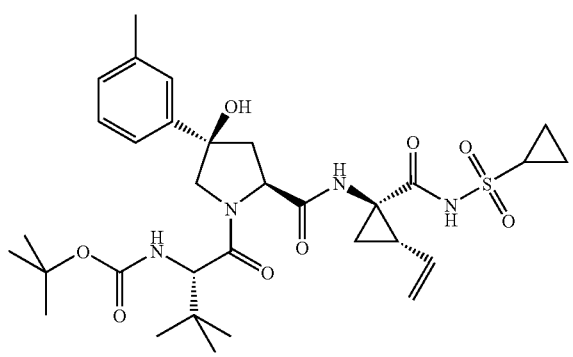

Example 13

Example 13 was prepared as described in the general procedure using m-tolylmagnesium bromide (1.0M in THF, 0.90 mL, 0.90 mmol) and 11 mg (11%) of product was obtained. ¹H NMR (400 MHz, CD₃OD) δ 0.99 (s, 2H), 1.04-1.09 (m, 10H), 1.21-1.27 (m, 2H), 1.42-1.47 (m, 10H), 1.87 (dd, J=8.31, 5.54 Hz, 1H), 2.18-2.29 (m, 2H), 2.35 (s, 3H), 2.56- 2.63 (m, 1H), 2.90-2.98 (m, 1H), 4.03 (d, J=11.08 Hz, 1H), 4.24 (d, J=10.83 Hz, 1H), 4.28-4.32 (m, 1H), 4.41 (dd, J=9.06, 4.03 Hz, 1H), 5.12 (dd, J=10.32, 1.51 Hz, 1H), 5.29 (dd, J=17.25, 1.38 Hz, 1H), 5.70-5.81 (m, 1H), 7.11 (d, J=7.55 Hz, 1H), 7.23 (t, J=7.55 Hz, 1H), 7.32 (d, J=7.81 Hz, 1H), 7.37 (s, 1H)); MS m/z 669 (M+Na)⁺.

Example 14

Preparation of Example 14

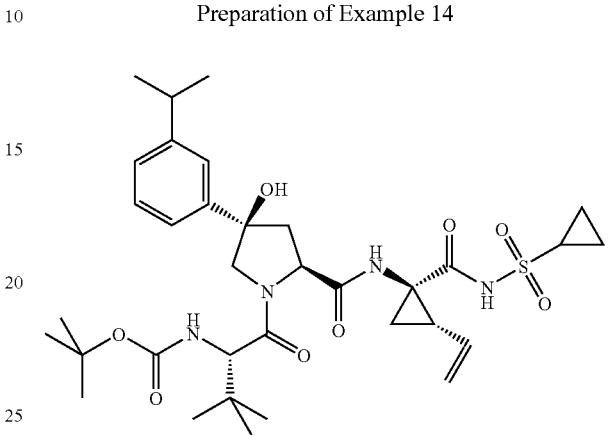

Example 14

Example 14 was prepared as described in the general procedure using (3-isopropylphenyl) magnesium bromide (0.5M in THF, 1.5 mL, 0.75 mmol) and 12 mg (12%) of product was obtained. ¹H NMR (400 MHz, CD₃OD) δ 0.98-1.01 (m, 2H), 1.04-1.11 (m, 10H), 1.22-1.28 (m, 8H), 1.41-1.47 (m, 10H), 1.87 (dd, J=8.18, 5.41 Hz, 1H), 2.18-2.34 (m, 2H), 2.55-2.63 (m, 1H), 2.87-2.98 (m, 2H), 4.00-4.07 (m, 1H), 4.26 (d, J=10.83 Hz, 1H), 4.29-4.33 (m, 1H), 4.42 (dd, J=9.06, 4.03 Hz, 1H), 5.12 (dd, J=10.45, 1.64 Hz, 1H), 5.29 (dd, J=17.12, 1.51 Hz, 1H), 5.70-5.81 (m, 1H), 7.17 (d, J=7.30 Hz, 1H), 7.24-7.36 (m, 2H), 7.44 (s, 1H). MS m/z 675 (M+H)⁺.

Example 15

Preparation of Example 15

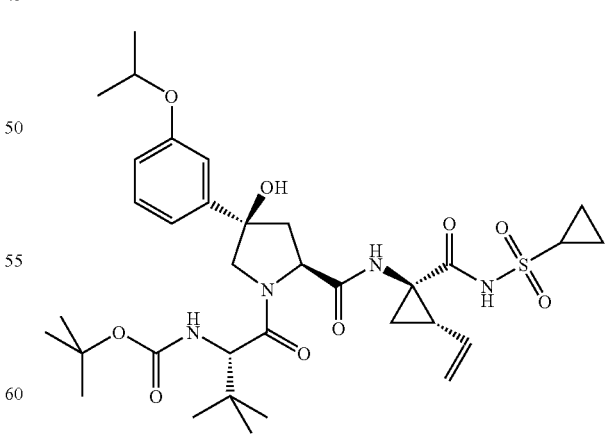

Example 15

Example 15 was prepared as described in the general procedure using (3-isopropoxyphenyl) magnesium bromide (0.5M in THF, 1.5 mL, 0.75 mmol) and 12 mg (12%) of product was obtained. $^1$H NMR (400 MHz, CD$_3$OD) δ 0.98-1.01 (m, 2H), 1.04-1.11 (m, 10H), 1.21-1.27 (m, 2H), 1.29 (d, J=6.04 Hz, 6H), 1.42-1.47 (m, 10H), 1.87 (dd, J=8.18, 5.41 Hz, 1H), 2.18-2.29 (m, 2H), 2.55-2.63 (m, 1H), 2.90-2.99 (m, 1H), 3.98-4.06 (m, 1H), 4.23 (d, J=10.83 Hz, 1H), 4.29 (s, 1H), 4.45 (dd, J=9.32, 3.78 Hz, 1H), 4.57-4.66 (m, 1H), 5.12 (dd, J=10.32, 1.76 Hz, 1H), 5.30 (dd, J=17.12, 1.51 Hz, 1H), 5.70-5.81 (m, 1H), 6.83 (dd, J=8.06, 1.76 Hz, 1H), 7.05 (d, J=7.81 Hz, 1H), 7.12 (s, 1H), 7.20-7.28 (m, 1H); MS m/z 691 (M+H)$^+$.

Example 16

Preparation of Example 16

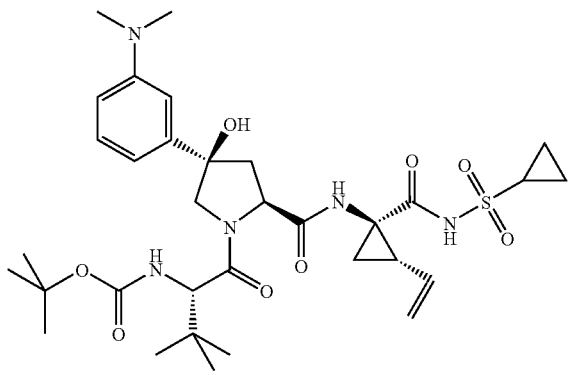

Example 16

Example 16 was prepared as described in the general procedure using [3-(N,N-dimethyl)aniline]magnesium bromide (0.5M in THF, 1.5 mL, 0.75 mmol) and 7 mg (7%) of product was obtained. $^1$H NMR (400 MHz, CD$_3$OD) δ 1.00 (s, 2H), 1.02-1.13 (m, 9H), 1.20-1.27 (m, 2H), 1.40-1.47 (m, 10H), 1.88 (dd, J=8.18, 5.41 Hz, 1H), 2.19-2.29 (m, 2H), 2.59-2.70 (m, 1H), 2.90-3.00 (m, 1H), 3.08-3.19 (m, 6H), 4.01-4.14 (m, 2H), 4.24 (d, J=10.83 Hz, 1H), 4.28 (s, 1H), 4.50 (dd, J=9.44, 3.15 Hz, 1H), 5.13 (dd, J=10.32, 1.76 Hz, 1H), 5.30 (dd, J=17.25, 1.39 Hz, 1H), 5.70-5.82 (m, 1H), 7.16-7.23 (m, 1H), 7.28-7.36 (m, 1H), 7.42 (t, J=7.43 Hz, 1H), 7.52 (s, 1H); MS m/z 676 (M+H)$^+$.

Example 17

Preparation of Example 17

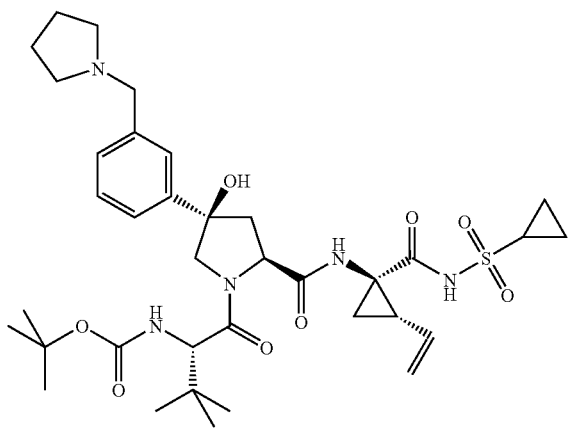

Example 17

Example 17 was prepared as described in the general procedure using [3-(1-pyrrolidinylmethyl)phenyl]magnesium bromide (0.25M in THF, 3.0 mL, 0.75 mmol) and 9 mg (9%) of product was obtained. $^1$H NMR (400 MHz, CD$_3$OD) δ 0.98-1.02 (m, 3H), 1.04-1.09 (m, 9H), 1.24 (d, J=1.51 Hz, 3H), 1.39-1.51 (m, 11H), 1.87 (dd, J=8.31, 5.54 Hz, 1H), 2.18-2.29 (m, 2H), 2.35 (s, 3H), 2.56-2.63 (m, 1H), 2.90-2.98 (m, 1H), 4.03 (d, J=11.08 Hz, 1H), 4.24 (d, J=10.83 Hz, 1H), 4.30 (s, 1H), 4.41 (dd, J=9.06, 4.03 Hz, 1H), 5.12 (dd, J=10.32, 1.51 Hz, 1H), 5.29 (dd, J=17.25, 1.38 Hz, 1H), 5.70-5.81 (m, 1H), 7.11 (d, J=7.55 Hz, 1H), 7.23 (t, J=7.55 Hz, 1H), 7.32 (d, J=7.81 Hz, 1H), 7.37 (s, 1H); MS m/z 716 (M+H)$^+$.

Example 18

Preparation of Example 18

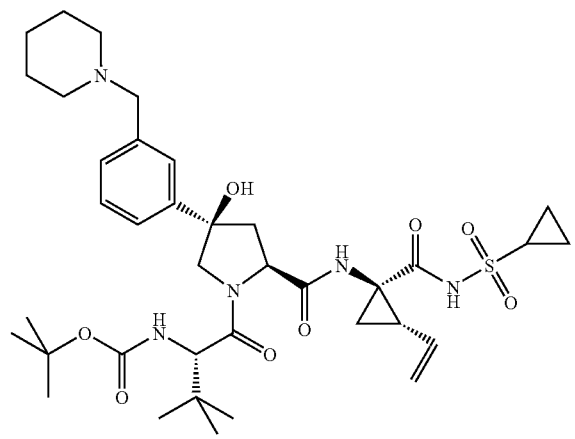

Example 18

Example 18 was prepared as described in the general procedure using [3-(1-piperidinylmethyl)phenyl]magnesium bromide (0.25M in THF, 3.0 mL, 0.75 mmol) and 15 mg (14%) of product was obtained. $^1$H NMR (400 MHz, CD$_3$OD) δ 0.99-1.04 (m, 5H), 1.07 (s, 9H), 1.15-1.26 (m, 3H), 1.41-1.47 (m, 13H), 1.77-1.92 (m, 5H), 2.11-2.40 (m, 2H), 2.65-2.76 (m, 1H), 2.86-2.97 (m, 1H), 4.08-4.19 (m, 2H), 4.28 (s, 3H), 4.52 (dd, J=9.82, 2.77 Hz, 1H), 5.05-5.15 (m, 1H), 5.22-5.34 (m, 1H), 5.72-5.85 (m, 1H), 7.44 (d, J=7.20 Hz, 1H), 7.49 (t, J=7.43 Hz, 1H), 7.66 (d, J=7.55 Hz, 1H), 7.81 (s, 1H); MS m/z 732 (M+H)$^+$.

Example 19

Preparation of Example 19

Compound 19

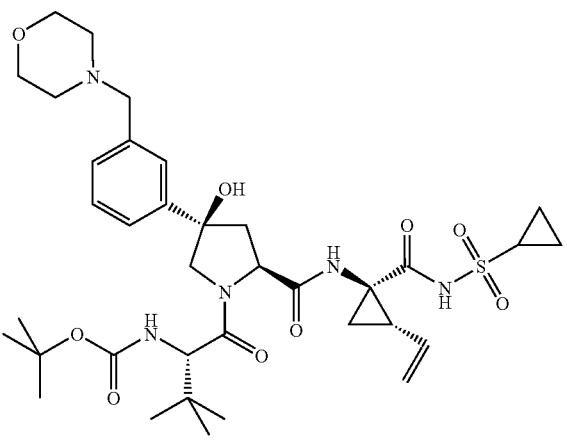

Example 19 was prepared as described in the general procedure using [3-(4-morpholinylmethyl)phenyl]magnesium bromide (0.25M in THF, 3.0 mL, 0.75 mmol) and 16 mg (15%) of product was obtained. $^1$H NMR (400 MHz, CD$_3$OD) δ 0.98-1.02 (m, 2H), 1.07 (s, 9H), 1.19-1.27 (m, 3H), 1.40-1.50 (m, 10H), 1.88 (dd, J=7.93, 5.67 Hz, 1H), 2.16-2.38 (m, 2H), 2.60-3.01 (m, 6H), 3.71-3.83 (m, 4H), 4.00-4.16 (m, 3H), 4.22 (d, J=10.83 Hz, 1H), 4.26-4.32 (m, 1H), 4.48 (dd, J=9.32, 2.77 Hz, 1H), 5.12 (d, J=10.58 Hz, 1H), 5.30 (d, J=16.87 Hz, 1H), 5.70-5.83 (m, 1H), 6.79 (d, J=8.81 Hz, 1H), 7.33-7.45 (m, 2H), 7.56 (d, J=8.06 Hz, 1H), 7.66 (s, 1H); MS 732 m/z (M+H)$^+$.

Example 20

Preparation of Example 20

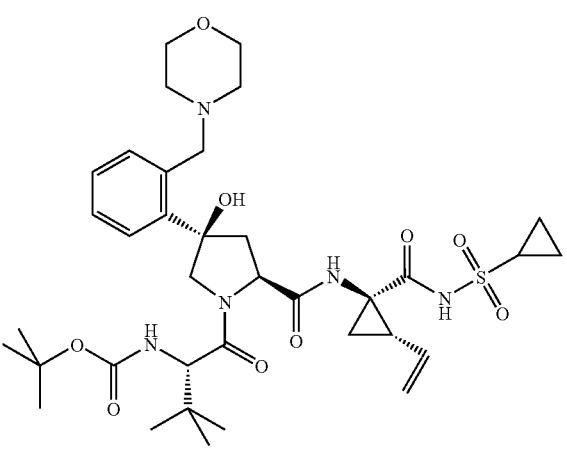

Example 20

Example 20 was prepared as described in the general procedure using [2-(4-morpholinylmethyl)phenyl]magnesium bromide (0.25M in THF, 3.6 mL, 0.90 mmol) and 4 mg (4%) of product was obtained. $^1$H NMR (400 MHz, CD$_3$OD) δ 0.94-0.98 (m, 2H), 1.01-1.11 (m, 10H), 1.16-1.24 (m, 2H), 1.41-1.48 (m, 10H), 1.85 (dd, J=8.06, 5.29 Hz, 1H), 2.12-2.22 (m, 1H), 2.45 (dd, J=12.59, 7.55 Hz, 1H), 2.55-2.68 (m, 4H), 2.72-2.85 (m, 1H), 2.87-2.97 (m, 1H), 3.59-3.84 (m, 6H), 4.00-4.07 (m, 1H), 4.13-4.21 (m, 1H), 4.34-4.38 (m, 1H), 4.47 (d, J=10.83 Hz, 1H), 5.10 (dd, J=10.20, 1.64 Hz, 1H), 5.26 (dd, J=17.12, 1.26 Hz, 1H), 5.68-5.80 (m, 1H), 6.77 (d, J=9.57 Hz, 1H), 7.28-7.40 (m, 3H), 7.44-7.49 (m, 1H); MS m/z (M+H)$^+$.

Example 21

Preparation of Example 21

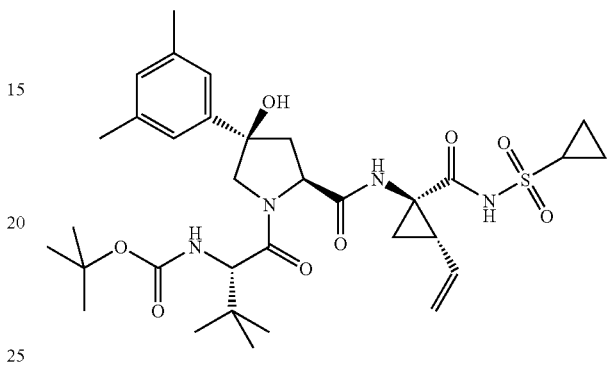

Example 21

Example 21 was prepared as described in the general procedure using (3,5-dimethylphenyl)magnesium bromide (0.5M in THF, 1.8 mL, 0.90 mmol) and 7 mg (7%) of product was obtained. $^1$H NMR (400 MHz, CD$_3$OD) δ 0.97-1.11 (m, 12H), 1.19-1.27 (m, 2H), 1.37-1.51 (m, 10H), 1.87 (dd, J=8.18, 5.41 Hz, 1H), 2.15-2.25 (m, 2H), 2.30 (s, 6H), 2.54-2.62 (m, 1H), 2.90-2.98 (m, 1H), 4.02 (d, J=10.58 Hz, 1H), 4.21 (d, J=10.83 Hz, 1H), 4.27-4.32 (m, 1H), 4.41 (dd, J=9.06, 3.78 Hz, 1H), 5.12 (dd, J=10.32, 1.51 Hz, 1H), 5.29 (dd, J=17.12, 1.51 Hz, 1H), 5.70-5.81 (m, 1H), 6.94 (s, 1H), 7.15 (s, 2H); MS m/z 683 (M+Na)$^+$.

Example 22

Preparation of Example 22

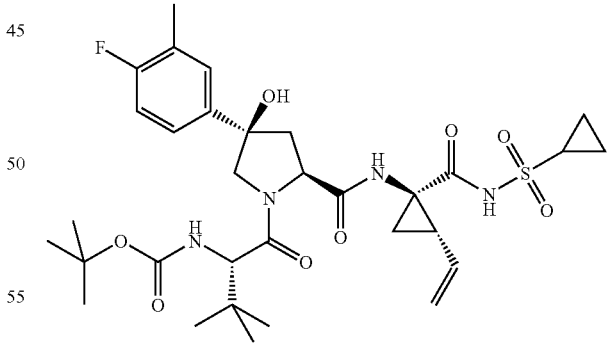

Example 22

Example 22 was prepared as described in the general procedure using (4-fluoro-3-methylphenyl)magnesium bromide (1.0M in THF, 0.9 mL, 0.90 mmol) and 8 mg (8%) of product was obtained. $^1$H NMR (400 MHz, CD$_3$OD) δ 0.97-1.02 (m, 2H), 1.03-1.11 (m, 10H), 1.20-1.27 (m, 2H), 1.41-1.47 (m, 10H), 1.87 (dd, J=8.18, 5.41 Hz, 1H), 2.20-2.25 (m, 1H), 2.27 (d, J=1.51 Hz, 3H), 2.55-2.63 (m, 1H), 2.89-2.98 (m, 1H), 4.03 (d, J=10.83 Hz, 1H), 4.21 (d, J=10.83 Hz, 1H), 4.26-4.31 (m, 1H), 4.41 (dd, J=9.19, 3.90 Hz, 1H), 5.12 (dd, J=10.32, 1.76 Hz, 1H), 5.30 (dd, J=17.12, 1.26 Hz, 1H), 5.70-5.81 (m, 1H), 6.79 (d, J=9.06 Hz, 1H), 6.96-7.03 (m, 1H), 7.33-7.40 (m, 1H), 7.41-7.46 (m, 1H); MS m/z 687 (M+Na)+.

Example 23

Preparation of Example 23

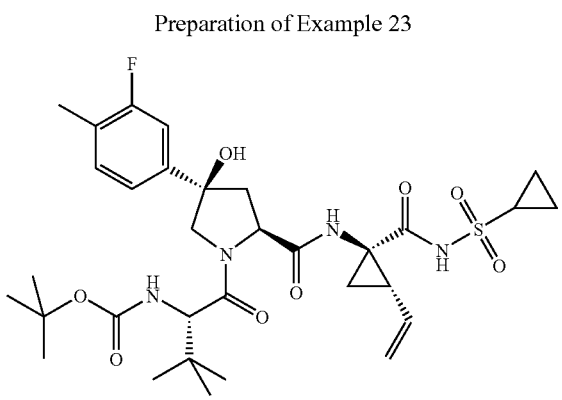

Example 23

Example 23 was prepared as described in the general procedure using (3-fluoro-4-methylphenyl)magnesium bromide (0.5M in THF, 1.8 mL, 0.90 mmol) and 5 mg (5%) of product was obtained. $^1$H NMR (400 MHz, CD$_3$OD) δ 0.99 (s, 2H), 1.03-1.10 (m, 10H), 1.21-1.27 (m, 2H), 1.42-1.47 (m, 10H), 1.87 (dd, J=8.31, 5.54 Hz, 1H), 2.19-2.22 (m, J=8.06 Hz, 1H), 2.24 (d, J=1.51 Hz, 3H), 2.54-2.61 (m, 1H), 2.90-2.98 (m, 1H), 4.01 (d, J=10.83 Hz, 1H), 4.22 (d, J=10.83 Hz, 1H), 4.26-4.30 (m, 1H), 4.41 (dd, J=9.06, 4.03 Hz, 1H), 5.12 (dd, J=10.32, 1.76 Hz, 1H), 5.29 (dd, J=17.25, 1.13 Hz, 1H), 5.70-5.81 (m, 1H), 7.20-7.27 (m, 3H); MS m/z 665 (M+H)+.

Example 24

Preparation of Example 24

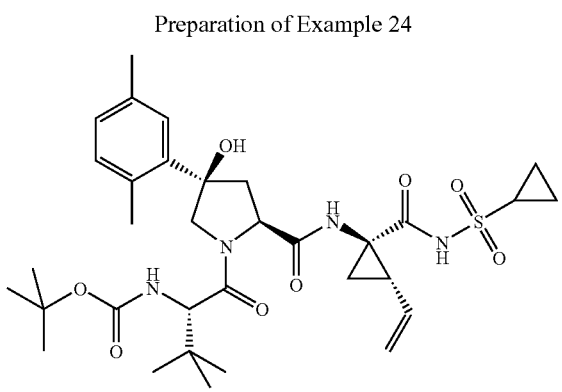

Example 24

Example 24 was prepared as described in the general procedure using (2,5-dimethylphenyl)magnesium bromide (0.5M in THF, 1.8 mL, 0.90 mmol) and 5 mg (5%) of product was obtained. $^1$H NMR (400 MHz, CD$_3$OD) δ 0.94-0.97 (m, 2H), 1.02-1.10 (m, 10H), 1.20-1.26 (m, 2H), 1.40-1.49 (m, 10H), 1.86 (dd, J=8.18, 5.41 Hz, 1H), 2.16 (d, J=4.78 Hz, 1H), 2.17-2.25 (m, 1H), 2.28 (s, 3H), 2.48 (s, 3H), 2.72 (dd, J=12.46, 8.18 Hz, 1H), 2.88-2.97 (m, 1H), 4.09 (d, J=10.83 Hz, 1H), 4.13-4.21 (m, 1H), 4.37 (d, J=9.32 Hz, 1H), 4.44 (d, J=10.83 Hz, 1H), 5.11 (dd, J=10.32, 1.51 Hz, 1H), 5.28 (dd, J=17.12, 1.51 Hz, 1H), 5.70-5.80 (m, 1H), 6.82 (d, J=9.57 Hz, 1H), 6.99 (t, J=7.68 Hz, 1H), 7.11 (d, J=7.30 Hz, 1H), 7.17 (d, J=7.81 Hz, 1H); MS m/z 683 (M+Na)+.

Example 25

Preparation of Example 25

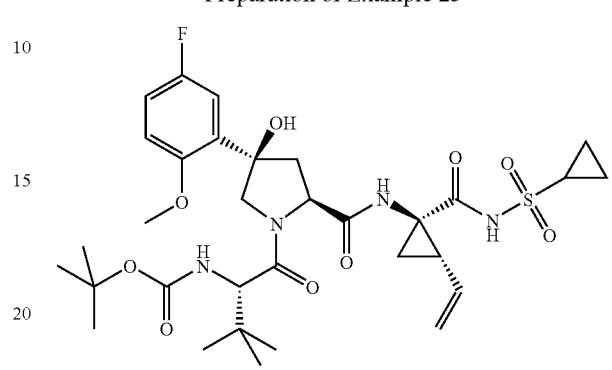

Example 25

Example 25 was prepared as described in the general procedure using (5-fluoro-2-methoxyphenyl)magnesium bromide (0.5M in THF, 1.8 mL, 0.90 mmol) and 5 mg (5%) of product was obtained. $^1$H NMR (400 MHz, CD$_3$OD) δ 1.00-1.10 (m, 11H), 1.20-1.26 (m, 2H), 1.40-1.47 (m, 10H), 1.83-1.89 (m, 1H), 2.20-2.29 (m, 1H), 2.34-2.43 (m, 1H), 2.90-2.98 (m, 1H), 3.80 (s, 1H), 3.85 (s, 3H), 3.93 (d, J=10.83 Hz, 1H), 4.18-4.28 (m, 1H), 4.45 (d, J=10.83 Hz, 1H), 4.56 (dd, J=9.69, 2.64 Hz, 1H), 5.12 (dd, J=10.58, 1.51 Hz, 1H), 5.30 (d, J=17.37 Hz, 1H), 5.68-5.83 (m, 1H), 6.75 (d, J=8.81 Hz, 1H), 6.98-7.04 (m, 2H), 7.36 (d, J=10.32 Hz, 1H); MS m/z 703 (M+Na)+.

Example 26

Preparation of Example 26

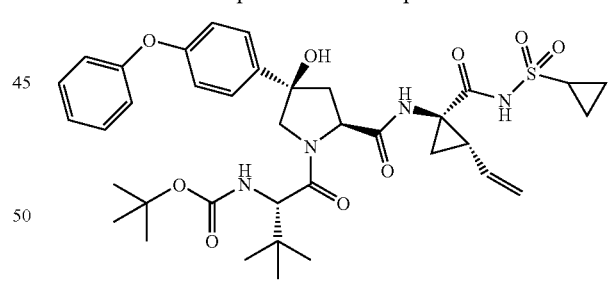

Example 26

To a solution of the product from Example 7, Step 4 (55 mg, 0.10 mmol) in THF (4 mL) was added (4-phenoxyphenyl)magnesium bromide (0.5 M/THF, 1.0 mL, 0.50 mmol) dropwise at −40° C. After stirring at this temperature for 2 h and then at 0° C. for 1 h, the mixture was quenched with 5% citric acid and extracted with EtOAc (10 mL). The organic layer was washed with brine, dried over MgSO$_4$, filtered and evaporated. The residue was triturated with hot hexane and was filtered. The solid thus obtained was purified by preparative HPLC to yield Compound 100 as a white solid (2.1 mg, 3%).

$^1$H NMR (CD$_3$OD) δ 1.02-1.09 (m, 11H), 1.26-1.29 (m, 2H), 1.45-1.50 (m, 10H), 1.90-1.92 (m, 1H), 2.25-2.27 (m, 2H), 2.68-2.69 (m, 1H), 2.95-2.99 (m, 1H), 4.05-4.07 (m, 1H), 4.35-4.52 (m, 2H), 5.15 (d, J=12 Hz, 1H), 5.32 (d, J=18.5 Hz, 1H), 5.75-5.82 (m, 1H), 6.97-7.01 (m, 4H), 7.15-7.16 (m, 1H), 7.36-7.39 (m, 2H), 7.56-7.58 (m, 2H);

LC-MS (retention time: 2.94 min, method B), MS m/z 707 (M$^+$–H2O).

Example 27

Preparation of Example 27

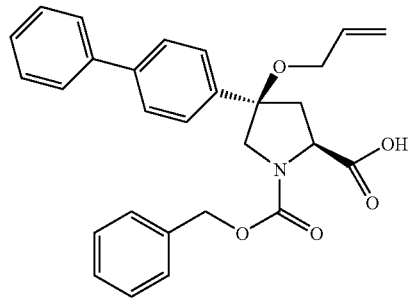

Example 27

Scheme 5

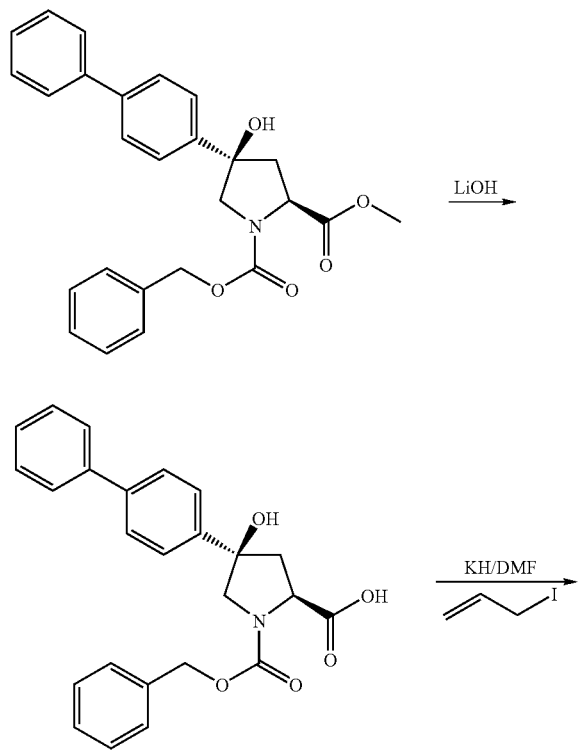

-continued

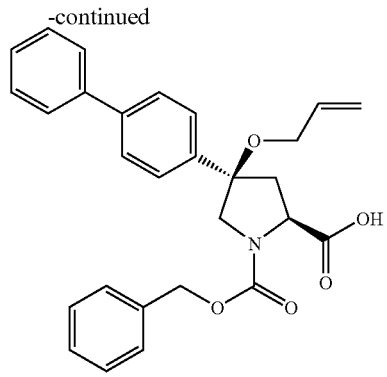

Step 1

To a solution of (2S,4R)-1-benzyl 2-methyl 4-(biphenyl-4-yl)-4-hydroxypyrrolidine-1,2-dicarboxylate (1.294 g, 3 mmol) in THF (10 ml) and MeOH (10.00 ml) was added pre-made solution of Lithium hydroxide monohydrate (0.252 g, 6.00 mmol) in Water (10.00 ml). The formed cloudy solution was stirred at room temperature for 6 h. Diluted with water, acidified by 1M HCl to pH 3, extracted with EtOAc (200 ml). The organic layer was washed with 5% citric acid, and brine, dried over MgSO4, filtered, evaporated. The residual powder was triturated with 4:1 hexane-EtOAc to afford the desired product (1.20 g, 96% yield) as white powder.

$^1$H NMR (CD$_3$OD) δ 2.53-2.57 (m, 1H), 2.79-2.86 (m, 1H), 3.83-3.90 (m, 2H), 4.62-4.66 (m, 1H), 5.16-5.20 (m, 2H), 7.24-7.46 (m, 8H), 7.57-7.66 (m, 6H);

LC-MS (retention time: 2.64 min, method B), MS m/z 400 (M$^+$–H2O).

Step 2

A pre-washed Potassium hydride (73.3 mg, 0.548 mmol) with hexane was stirred in DMF (2.5 mL). (2S,4R)-1-(benzyloxycarbonyl)-4-(biphenyl-4-yl)-4-hydroxypyrrolidine-2-carboxylic acid (104 mg, 0.249 mmol) was added as solid by one portion at 0° C. The formed white gel was stirred at this temperature for 30 min (became almost clear solution at this point) before addition of Allyl iodide (0.027 mL, 0.299 mmol). The final cloudy solution was stirred at this temperature for 2 h. Quenched with iced 5% citric acid, extracted with EtOAc. Washed the organic layer with brine, dried over MgSO$_4$, filtered, evaporated. Purified by prep-HPLC to afford 35 mg of the starting material, and the desired product (45 mg, 40% yield) as a white solid.

$^1$H NMR (CD$_3$OD) δ 2.56-2.57 (m, 1H), 2.81-2.84 (m, 1H), 3.82-3.87 (m, 2H), 4.69-4.73 (m, 3H), 5.14-5.23 (m, 3H), 5.30-5.41 (m, 1H), 5.87-6.01 (m, 1H), 7.34-7.46 (m, 8H), 7.57-7.66 (m, 6H);

LC-MS (retention time: 2.64 min, method B), MS m/z 458 (M$^+$+H).

Example 28

Preparation of Example 28

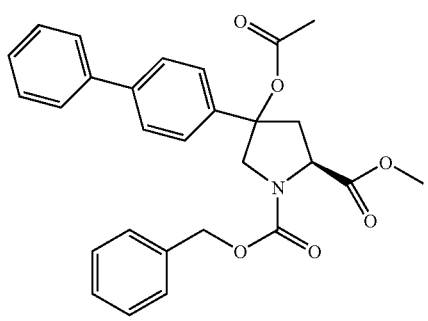

Example 28

Scheme 6

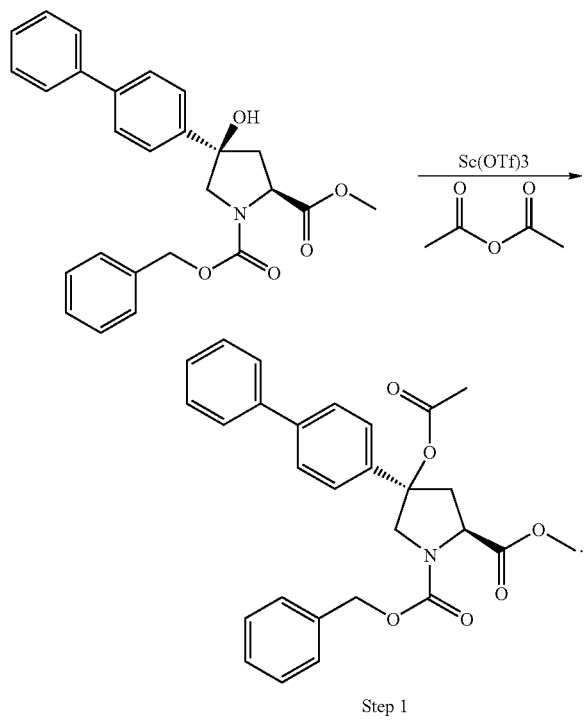

Step 1

To a solution of (2S,4R)-1-benzyl 2-methyl 4-(biphenyl-4-yl)-4-hydroxypyrrolidine-1,2-dicarboxylate (540 mg, 1.252 mmol) in Acetic anhydride (10 mL, 106 mmol) was added pre-made solution of Scandium trifluoromethanesulfonate (61.6 mg, 0.125 mmol) in acetonitrile (0.5 ml) dropwise at 0° C. The formed light pink solution was stirred at this temperature for 1 h. Quenched with sat. ammonium chloride, extracted with EtOAc. Washed the organic layer with brine, dried over $MgSO_4$, filtered, evaporated. The residue was purified by prep-HPLC to afford the desired product (290 mg, 49%) as a mixture of diastereomers.

$^1$H NMR ($CDCl_3$) δ 1.97 (s, 1/3H), 2.00 (s, 2/3H), 2.42-2.50 (m, 1/3H), 2.68-2.79 (m, 2/3H), 3.03-3.05 (m, 2/3H), 3.24-3.41 (m, 1/3H), 3.54, 3.77 (s, 1H, rotamers), 3.66, 3.79 (s, 2H, rotamers), 3.80-3.90 (m, 1/3H), 4.10-4.19 (m, 2/3H), 4.20-4.29 (m, 2/3H), 4.49-4.57 (m, 1/3H), 4.52-4.60 (m, 1H), 5.09-5.26 (m, 2H), 7.30-7.56 (m, 14H);

LC-MS (retention time: 2.78 min, method B), MS m/z 496 ($M^+$–$CH_3CO_2OH$).

Example 101

Preparation of Example 101

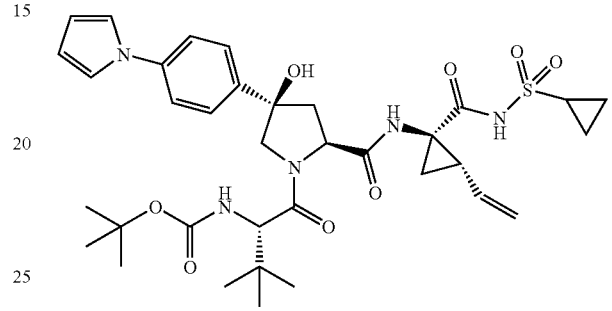

Example 101

Scheme 1

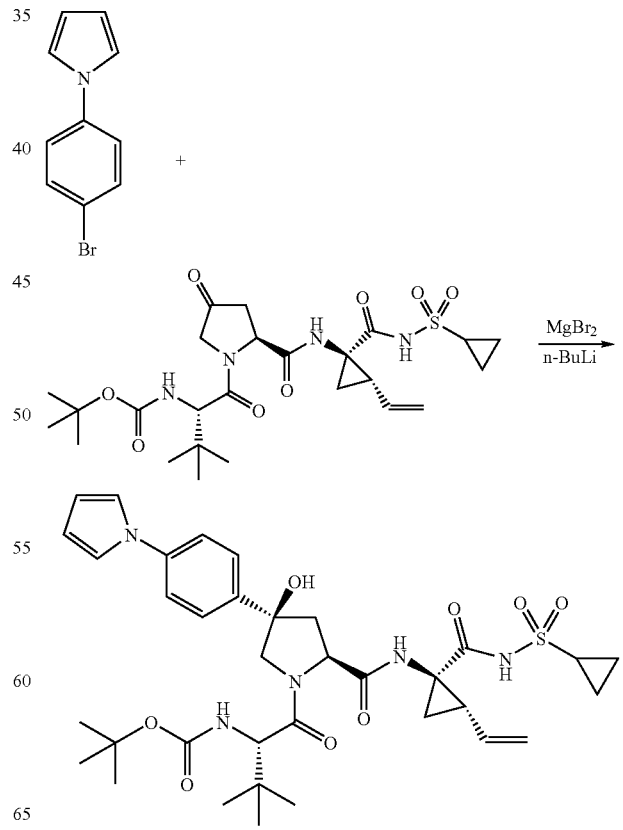

Step 1

A 2-necked flask was charged with ground magnesium bromide etherate (258 mg, 1.0 mmol). This flask was heated with an oil bath at 70° C. under high vacuum for 4 h. After cooling this flask in an ice bath, the product from Example 7, Step 4 (110 mg, 0.20 mmol) was added along with THF (5 mL), and the resulting slightly yellow slurry was vigorously stirred at room temperature overnight.

Step 2

To another 2-necked flask containing 1-(4-bromophenyl)-1H-pyrrole (239 mg, 1.0 mmol) and THF (4 mL) at −78° C. was added n-BuLi (2.5 M, 0.4 mL, 1.0 mmol) dropwise. The resulting mixture was stirred at this temperature for 15 min. The slurry was cannulated into the flask from Step 1 which had been pre-cooled to −78° C. The final mixture was stirred at this temperature for 2 h and at 0° C. for an additional 1 h. The mixture was quenched with sat. NH₄Cl, diluted with EtOAc, and the upper organic phase was separated. The organic layer was washed with brine, dried over MgSO₄, filtered and evaporated. The residue was triturated with hot hexane and was filtered. The solid obtained was purified by preparative HPLC to yield Example 101 as a white solid (16.5 mg, 12%).

$^1$H NMR (CD$_3$OD) δ 1.02-1.09 (m, 11H), 1.26-1.29 (m, 2H), 1.45-1.50 (m, 10H), 1.90-1.92 (m, 1H), 2.25-2.27 (m, 2H), 2.68-2.69 (m, 1H), 2.95-2.99 (m, 1H), 4.05-4.07 (m, 1H), 4.35-4.52 (m, 2H), 5.15 (d, J=12 Hz, 1H), 5.32 (d, J=18.5 Hz, 1H), 5.75-5.82 (m, 1H), 6.30 (m, 2H), 7.20-7.21 (m, 2H), 7.48-7.51 (m, 2H), 7.66-7.68 (m, 2H);

LC-MS (retention time: 2.81 min, method B), MS m/z 698 (M$^+$+H), 680 (M$^+$−H2O).

Example 102

Preparation of Example 102

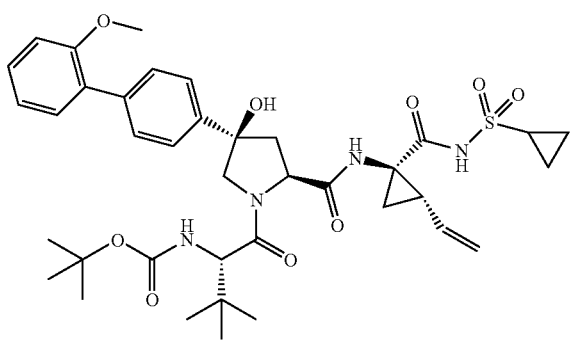

Example 102

Example 102 was prepared by the same procedure as described in Example 101, except using 4'-bromo-2-methoxybiphenyl instead of 1-(4-bromophenyl)-1H-pyrrole in Step 2.

$^1$H NMR (CD$_3$OD) δ 1.02-1.09 (m, 11H), 1.26-1.29 (m, 2H), 1.45-1.50 (m, 10H), 1.90-1.92 (m, 1H), 2.25-2.27 (m, 2H), 2.68-2.69 (m, 1H), 2.95-2.99 (m, 1H), 3.80 (s, 3H), 4.05-4.07 (m, 1H), 4.35-4.52 (m, 2H), 5.15 (d, J=12 Hz, 1H), 5.32 (d, J=18.5 Hz, 1H), 5.75-5.82 (m, 1H), 7.00-7.09 (m, 2H), 7.27-7.34 (m, 2H), 7.44-7.51 (m, 4H);

LC-MS (retention time: 2.90 min, method B), MS m/z 729 (M$^+$+H), 721 (M$^+$−H2O).

Example 103

Preparation of Example 103

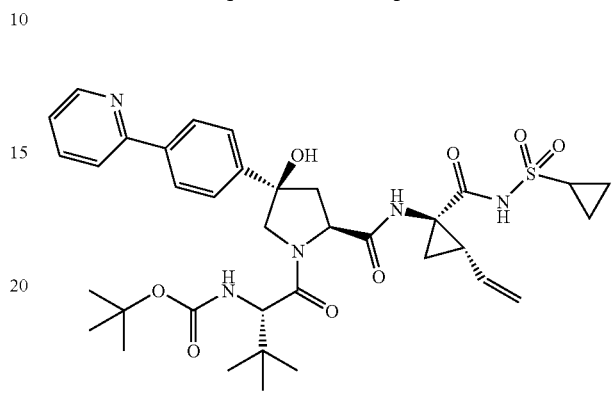

Example 103

Step 1

A 2-necked flask was charged with ground cerium (III) chloride heptahydrate (373 mg, 1.0 mmol). This flask was heated with an oil bath at 70° C. under high vacuum for 20 h, then at 100° C. for 2 h, then 120° C. for 2 h, and finally 160° C. for 16 h. After cooling this flask in an ice bath, the product from Example 7, Step 4 (110 mg, 0.20 mmol) and THF (5 mL) was added. The resulting slightly yellow slurry was vigorously stirred at room temperature for 4 h.

Step 2

To another 2-necked flask containing 2-(4-bromophenyl) pyridine (JOC, 2003, p 6959, 233 mg, 1.0 mmol) and THF (4 mL) at −78° C. was added n-BuLi (2.5 M, 0.4 mL, 1.0 mmol) dropwise and the mixture was stirred at this temperature for 15 min. The formed slurry was cannulated into the flask from Step 1 which was pre-cooled to −78° C. The final mixture was stirred at this temperature for 2 h and then at 0° C. for an additional 1 h. The mixture was quenched with sat. NH₄Cl, diluted with EtOAc, and the upper organic layer was separated. The organic layer was washed with brine, dried over MgSO₄, filtered and evaporated. The residue was triturated with hot hexane and was filtered. The solid obtained was purified by preparative HPLC to yield Example 103 as a white solid (17 mg, 12%).

$^1$H NMR (CD$_3$OD) δ 1.02-1.09 (m, 11H), 1.26-1.29 (m, 2H), 1.45-1.50 (m, 10H), 1.90-1.92 (m, 1H), 2.25-2.27 (m, 2H), 2.68-2.69 (m, 1H), 2.95-2.99 (m, 1H), 4.05-4.07 (m, 1H), 4.35-4.52 (m, 2H), 5.15 (d, J=12 Hz, 1H), 5.32 (d, J=18.5 Hz, 1H), 5.75-5.82 (m, 1H), 7.38-7.40 (m, 1H), 7.71-7.74 (m, 2H), 7.87-8.00 (m, 4H), 7.63-7.64 (m, 1H);

LC-MS (retention time: 2.24 min, method B), MS m/z 710 (M$^+$+H).

Example 104

Preparation of Example 104

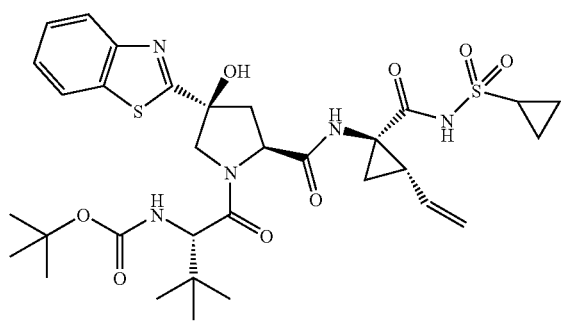

Example 104

Example 104 was prepared by the same procedure as described in Example 101, except using 2-bromobenzo[d]thiazole instead of 1-(4-bromophenyl)-1H-pyrrole in Step 2.

$^1$H NMR (CD$_3$OD) δ 1.02-1.09 (m, 11H), 1.26-1.29 (m, 2H), 1.45-1.50 (m, 10H), 1.90-1.92 (m, 1H), 2.25-2.27 (m, 2H), 2.68-2.69 (m, 1H), 2.95-2.99 (m, 1H), 3.80 (s, 3H), 4.05-4.07 (m, 1H), 4.35-4.52 (m, 2H), 5.15 (d, J=12 Hz, 1H), 5.32 (d, J=18.5 Hz, 1H), 5.75-5.82 (m, 1H), 7.43-7.52 (m, 2H), 7.93-8.01 (m, 2H);

LC-MS (retention time: 2.79 min, method B), MS m/z 690 (M$^+$+H).

Example 105

Preparation of Example 105

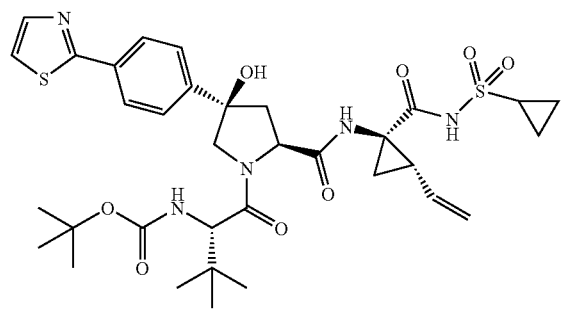

Example 105

Example 105 was prepared by the same procedure as described in Example 101, except using 2-(4-bromophenyl)thiazole instead of 1-(4-bromophenyl)-1H-pyrrole in Step 2.

$^1$H NMR (CD$_3$OD) δ 1.02-1.09 (m, 11H), 1.26-1.29 (m, 2H), 1.45-1.50 (m, 10H), 1.90-1.92 (m, 1H), 2.25-2.27 (m, 2H), 2.68-2.69 (m, 1H), 2.95-2.99 (m, 1H), 3.80 (s, 3H), 4.05-4.07 (m, 1H), 4.35-4.52 (m, 2H), 5.15 (d, J=12 Hz, 1H), 5.32 (d, J=18.5 Hz, 1H), 5.75-5.82 (m, 1H), 7.64 (m, 1H), 7.72-7.74 (m, 2H), 7.90 (m, 1H), 7.98-7.99 (m, 2H);

LC-MS (retention time: 2.67 min, method B), MS m/z 716 (M$^+$+H).

Preparation of Compounds of the Present Disclosure

Example 106

Preparation of Compound 106

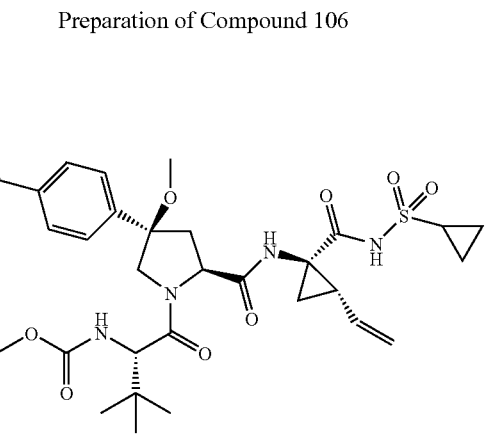

Scheme 2

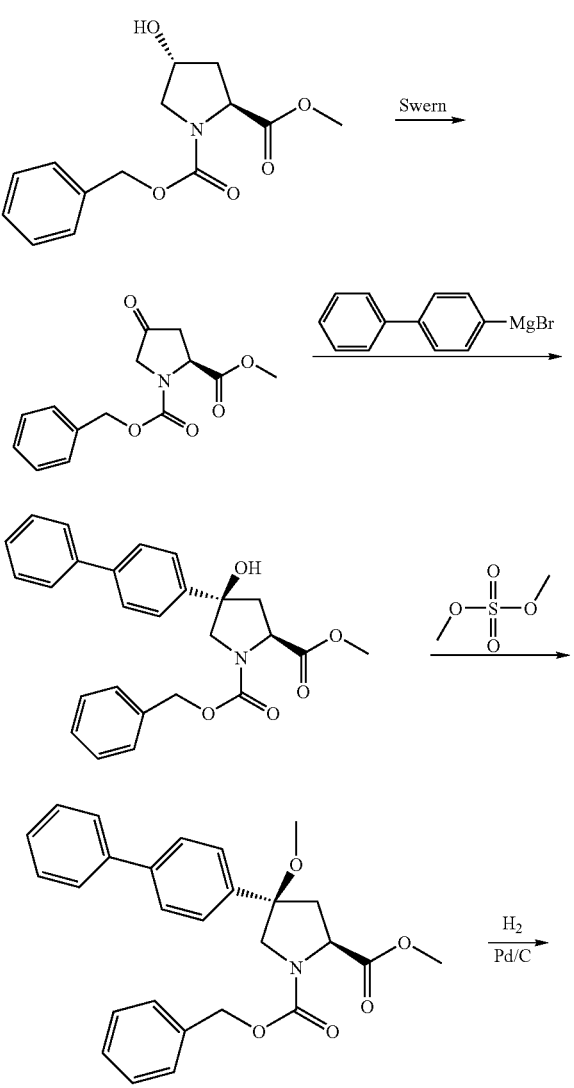

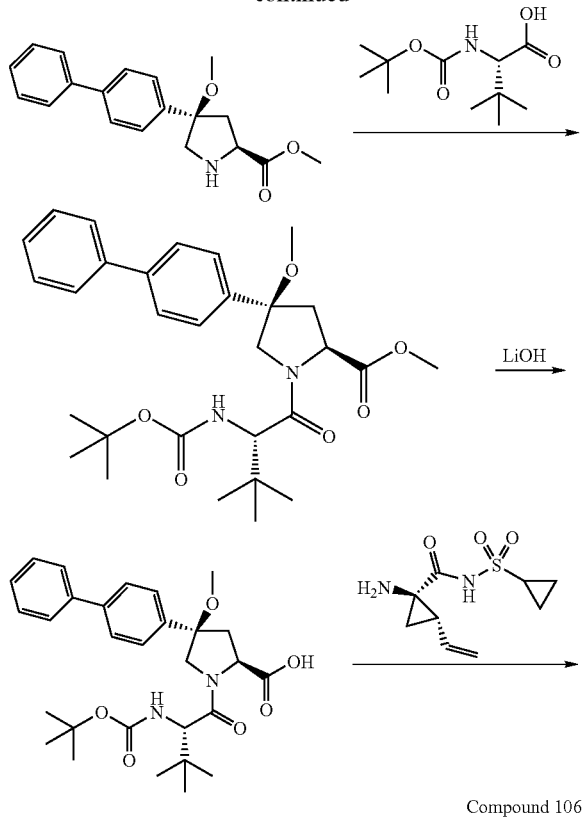

Compound 106

Step 1

To solution of methyl sulfoxide (23.90 ml, 337 mmol) in DCM (100 ml) at −78° C. was added oxalyl chloride (2 M in DCM, 84 ml, 168 mmol) dropwise. The formed solution was stirred at this temperature for 30 min. A solution of (2S,4R)-1-benzyl 2-methyl 4-hydroxypyrrolidine-1,2-dicarboxylate (21.38 g, 77 mmol) in DCM (100 ml) was added dropwise at −78° C. The formed slurry was stirred at −78° C. for 2 hr before addition of N,N-Diisopropylethylamine (66.7 ml, 383 mmol) dropwise. The final solution was stirred at room temperature 3 h. The mixture was washed with iced 1M HCl, 5% citric acid, and then brine, dried over MgSO$_4$, filtered, and evaporated. The residual light brown oil was purified by silica gel column chromatography, eluted with 4:1, 3:1, then 2:1 hexane-EtOAc to afford (S)-1-benzyl 2-methyl 4-oxopyrrolidine-1,2-dicarboxylate (14.8 g, 70% yield) as light brown viscous oil. $^1$H NMR (CDCl$_3$) δ 2.58-2.63 (m, 1H), 2.90-2.99 (m, 1H), 3.62, 3.77 (s, 3H, rotamers), 3.95-4.02 (m, 2H), 4.82-4.89 (m, 1H), 5.11-5.24 (m, 2H), 7.32-7.39 (m, 5H).

Step 2

To a solution of (S)-1-benzyl 2-methyl 4-oxopyrrolidine-1,2-dicarboxylate (14.0 g, 50.5 mmol) in toluene (500 mL) at 0° C. was added biphenyl-4-ylmagnesium bromide (152 mL, 0.5 M in THF, 75.75 mmol) dropwise. The formed light yellow solution was stirred at this temperature for 1 h. Quenched with NH$_4$Cl, separated the organic layer. The aqueous layer was extracted with EtOAc. Washed the combined organic layers with brine, dried over MgSO$_4$, filtered, and evaporated. The residue was purified by passing through a silica gel plug, eluted with 4:1, 3:1 then 2:1, and finally 3:2 hexane-EtOAc to provide 11.70 g white solid, which was recrystallized from EtOAc-Hexane (50 ml-150 ml) to afford 7.8 g of (2S,4R)-1-benzyl 2-methyl 4-(biphenyl-4-yl)-4-hydroxypyrrolidine-1,2-dicarboxylate as small needles. The mother liqor was concentrated and purified by flash column, eluted with 4:1, 3:1, then 2:1, and finally 3:2 hexane-EtOAc to yield additional 2.41 g of the desired product. $^1$H NMR (CDCl$_3$) δ 2.39-2.45 (m, 1H), 2.70-2.75 (m, 1H), 3.66, 3.86 (s, 3H, rotamers), 3.80-3.90 (m, 1H), 4.00-4.07 (m, 1H), 4.62 (dd, J$_{1,2}$=9.5, 28 Hz, 1H), 5.09-5.15 (m, 1H), 5.21-5.25 (m, 1H), 7.31-7.38 (m, 6H), 7.42-7.45 (m, 2H), 7.54-7.59 (m, 6H);

LC-MS (retention time: 2.77 min, method B), MS m/z 414 (M$^+$−H$_2$O), 370 (M$^+$−H$_2$O—CO$_2$).

Step 3

To a solution of (2S,4R)-1-benzyl 2-methyl 4-(biphenyl-4-yl)-4-hydroxypyrrolidine-1,2-dicarboxylate (8.08 g, 18.73 mmol) in DMF (150 ml) at 0° C. was added sodium hydride (0.520 g, 20.60 mmol). The formed light brown solution was stirred at this temperature for 30 min. Dimethyl sulfate (1.949 ml, 20.60 mmol) was added dropwise at 0° C. The final solution was stirred at room temperature for 2 h. Quenched with 5% citric acid, extracted with EtOAc. Washed the organic with brine, dried over MgSO$_4$, filtered, and evaporated. The residue was purified by flash column silica gel chromatography, eluted with 4:1, 3:1, then 2:1 hexane-EtOAc to yield 1.45 g of the desired product, which was recrystallized in MeOH (10 ml) to yield 1.20 g (14.38% yield) as a white solid. 4.50 g of starting material was also recovered during flash column purification.

$^1$H NMR (CDCl$_3$) δ 2.51-2.56 (m, 1H), 2.85-2.89 (m, 1H), 2.95, 2.97 (s, 3H, rotamers), 3.67, 3.80 (s, 3H, rotamers), 3.69-3.86 (m, 1H), 4.02-4.08 (m, 1H), 4.62 (dd, J$_{1,2}$=9.5, 28 Hz, 1H), 5.09-5.17 (m, 1H), 5.20-5.29 (m, 1H), 7.29-7.46 (m, 10H), 7.57-7.60 (m, 4H);

LC-MS (retention time: 2.92 min, method B), MS m/z 446 (M$^+$+H), 414 (M$^+$−MeOH), 370 (M$^+$−MeOH—CO$_2$). Step 4.

To an iced Parr shaker vessel containing solution of (2S,4R)-1-benzyl 2-methyl 4-(biphenyl-4-yl)-4-methoxypyrrolidine-1,2-dicarboxylate (1.29 g, 2.90 mmol) in MeOH (30 ml) was added Palladium (0.308 g, 0.290 mmol) on carbon (10%, wet). The vessel was placed on a Parr shaker apparatus under hydrogen with 25 psi pressure for 5 h. Quenched with celite. Filtered, evaporated to afford 0.811 g (91%) of the desired product as an off-white powder. This material was used for the next coupling reaction without further purification.

LC-MS (retention time: 1.92 min, method B), MS m/z 312 (M$^+$+H), 280 (M$^+$-MeOH).

Step 5

To a solution of (2S,4R)-methyl 4-(biphenyl-4-yl)-4-methoxypyrrolidine-2-carboxylate (500 mg, 1.606 mmol), (S)-2-(tert-butoxycarbonylamino)-3,3-dimethylbutanoic acid (409 mg, 1.77 mmol), and HATU (867 mg, 2.409 mmol) in DCM (15 ml) was added N,N-Diisopropylethylamine (0.839 ml, 4.82 mmol) at 0° C. The formed solution was stirred at room temperature for 4 h. Diluted with DCM, washed with 5% citric acid and brine, dried over MgSO$_4$, filtered, evaporated. The residue was purified by silica gel column, eluted with 2:1 hexane-acetone to afford the desired product (600 mg, 71% yield) as a white foam.

¹H NMR (CD₃OD) δ 1.11 (s, 9H), 1.42 (s, 9H), 2.61-2.66 (m, 1H), 2.71-2.75 (m, 1 H), 3.00 (s, 3H), 3.75 (s, 3H), 4.20-4.25 (m, 2H), 4.30-4.35 (m, 1H), 4.75-4.79 (m, 1H), 7.35-7.72 (m, 9H);

LC-MS (retention time: 3.04 min, method B), MS m/z 525 (M⁺+H), 493 (M⁺-MeOH).

Step 6

To a solution of (2S,4R)-methyl 4-(biphenyl-4-yl)-1-((S)-2-(tert-butoxycarbonylamino)-3,3-dimethylbutanoyl)-4-methoxypyrrolidine-2-carboxylate (600 mg, 1.144 mmol) in THF (5 ml) and MeOH (5.00 ml) was added pre-made solution of lithium hydroxide monohydrate (96 mg, 2.287 mmol) in water (5.00 ml). The formed cloudy solution was stirred at room temperature for 8 h. Removed the volatiles, diluted with 5% citric acid, extracted with EtOAc. The organic layer was washed with brine, dried over MgSO₄, filtered, and evaporated. The residual powder (534 mg, 91% yield) was recrystallized from EtOAc-Hexane (2 ml-4 ml) to yield 450 mg of the desired product as a white crystal.

LC-MS (retention time: 2.93 min, method B), MS m/z 511 (M⁺+H), 479 (M⁺-MeOH).

Step 7

To a slurry of (2S,4R)-4-(biphenyl-4-yl)-1-((S)-2-(tert-butoxycarbonylamino)-3,3-dimethylbutanoyl)-4-methoxypyrrolidine-2-carboxylic acid (255 mg, 0.499 mmol), (1R,2S)-1-amino-N-(cyclopropylsulfonyl)-2-vinylcyclopropanecarboxamide, tosylic acid, hydrate (231 mg, 0.549 mmol), and HATU (228 mg, 0.599 mmol) in CH2Cl2 (5 ml) at 0° C. was added N,N-Diisopropylethylamine (0.435 ml, 2.497 mmol). The formed light yellow solution was stirred at 0° C. for 3 hr. Diluted with EtOAc (10 mL), washed with 5% citric acid and brine, dried over MgSO4, filtered, and evaporated in vacuo. The residue was purified by preparative HPLC (Phenomenex-Luna 30×100 mm S10, 30% B to 100% B, 15 min gradient time, 20 min stop) to afford Compound 106 (248 mg, 68.7% yield) as a white solid.

¹H NMR (CD₃OD) δ 1.01-1.12 (m, 11H), 1.26-1.27 (m, 2H), 1.43-1.50 (m, 10H), 1.87-1.90 (m, 1H), 2.20-2.25 (m, 1H), 2.49-2.57 (m, 2H), 2.95-2.99 (m, 1H), 3.11 (s, 3H), 4.07-4.09 (m, 1H), 4.22-4.24 (m, 1H), 4.42 (d, J=9 Hz, 1H), 4.58-4.60 (m, 1H), 5.15 (d, J=12 Hz, 1H), 5.32 (d, J=18.5 Hz, 1H), 5.75-5.82 (m, 1H), 7.38-7.39 (m, 1H), 7.45-7.48 (m, 2H), 7.57-7.67 (m, 6H);

LC-MS (retention time: 2.96 min, method B), MS m/z 723 (M⁺+H).

Example 107

Preparation of Compound 107

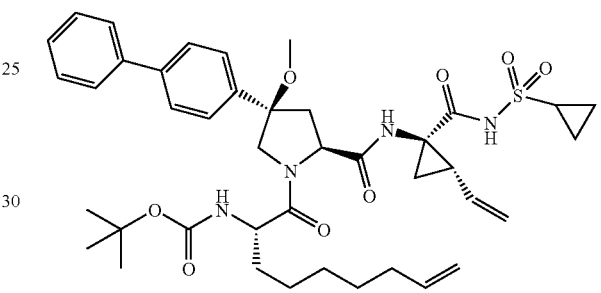

Scheme 3

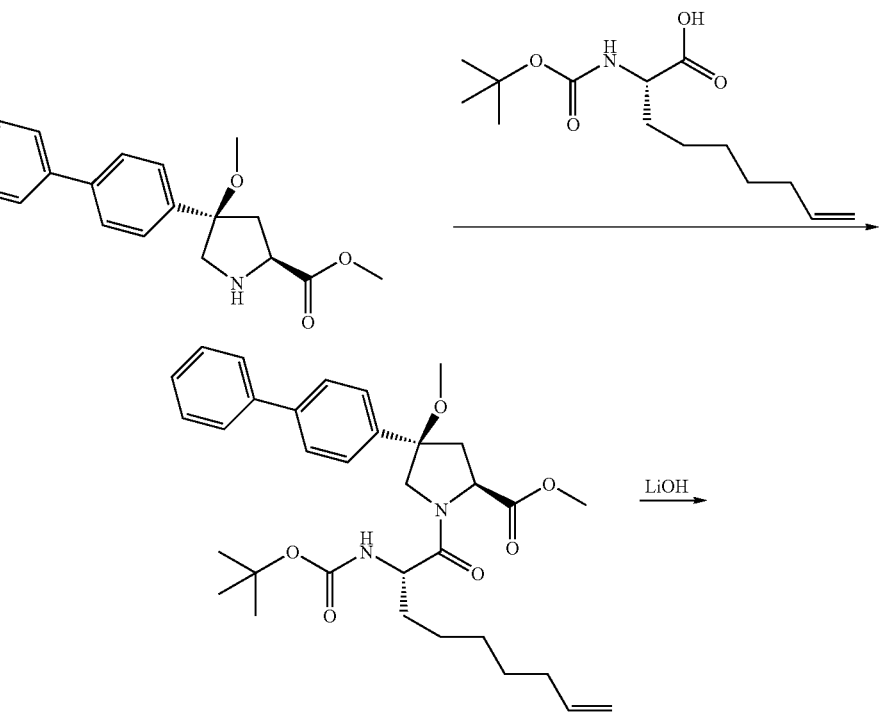

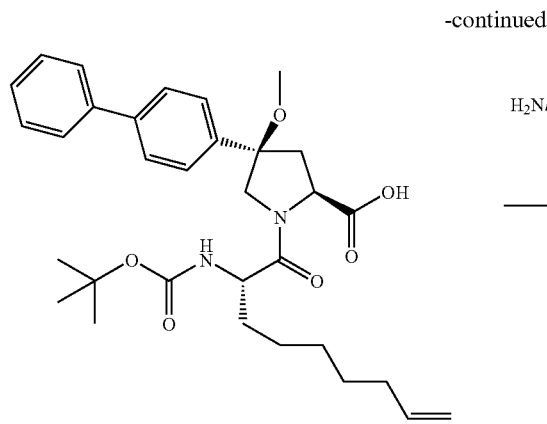

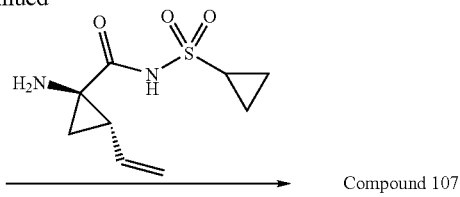

Compound 107

Step 1

To a solution of (2S,4R)-methyl 4-(biphenyl-4-yl)-4-methoxypyrrolidine-2-carboxylate (150 mg, 0.482 mmol), (S)-2-(tert-butoxycarbonylamino)non-8-enoic acid (144 mg, 0.530 mmol), and HATU (260 mg, 0.723 mmol) in DCM (5 ml) was added N,N-Diisopropylethylamine (0.252 ml, 1.445 mmol) at 0° C. The formed solution was stirred at room temperature overnight. Diluted with DCM, washed with 5% citric acid and brine, dried over MgSO$_4$, filtered and evaporated. The residue was purified by preparative HPLC to yield the desired product (140 mg, 51.5% yield) as white foam.

$^1$H NMR (CD$_3$OD) δ 1.31-1.57 (m, 15H), 1.62-1.65 (m, 1H), 1.78-1.82 (m, 1H), 2.11-2.13 (m, 2H), 2.66-2.69 (m, 1H), 2.84-2.89 (m, 1H), 3.00 (s, 3H), 3.76 (s, 3H), 4.16 (s, 2H), 4.30-4.35 (m, 1H), 4.79-4.81 (m, 1H), 4.95 (d, J=12 Hz, 1H), 5.03 (d, J=18.5 Hz, 1H), 5.83-5.87 (m, 1H), 7.32-7.39 (m, 1H), 7.45-7.56 (m, 4H), 7.64-7.71 (m, 4H);

LC-MS (retention time: 3.20 min, method B), MS m/z 565 (M$^+$+H).

Step 2

To a solution of (2S,4R)-methyl 4-(biphenyl-4-yl)-1-((S)-2-(tert-butoxycarbonylamino)non-8-enoyl)-4-methoxypyrrolidine-2-carboxylate (166 mg, 0.294 mmol) in THF (2 mL) and MeOH (2 mL) was added pre-made solution of lithium hydroxide monohydrate (37 mg, 0.882 mmol) in water (2 mL). The formed cloudy solution was stirred at room temperature overnight. Removed the volatiles in vacuo. The residue taken up in water, acidified with 1M HCl to pH 2. Extracted with EtOAc. Washed the organic layer with 5% citric acid and brine, dried over MgSO$_4$, filtered and evaporated. The residual white solid (148 mg, 91% yield) was used for the next coupling reaction without further purification.

LC-MS (retention time: 3.14 min, method B), MS m/z 551 (M$^+$+H).

Step 3

To a slurry of (2S,4R)-4-(biphenyl-4-yl)-1-((S)-2-(tert-butoxycarbonylamino)non-8-enoyl)-4-methoxypyrrolidine-2-carboxylic acid (78 mg, 0.142 mmol), (1R,2S)-1-amino-N-(cyclopropylsulfonyl)-2-vinylcyclopropanecarboxamide, tosylic acid, hydrate (65.5 mg, 0.156 mmol), and HATU (77 mg, 0.212 mmol) in DCM (3 ml) was added N,N-Diisopropylethylamine (0.074 ml, 0.425 mmol) at 0° C. The final mixture was stirred at room temperature overnight. Diluted with DCM, washed with 5% citric acid and brine, dried over MgSO$_4$, filtered and evaporated. The residue was purified by preparative HPLC to afford Compound 107 (64 mg, 59% yield) as white solid. $^1$H NMR (CD$_3$OD) δ 1.11-1.12 (m, 2H), 1.26-1.28 (m, 2H), 1.37-1.51 (m, 15H), 1.64-1.72 (m, 1H), 1.87-1.89 (m, 2H), 2.08-2.11 (m, 2H), 2.28-2.31 (m, 1H), 2.95-2.99 (m, 1H), 3.09 (s, 3H), 4.19 (d, J=9 Hz, 1H), 4.38-4.41 (m, 2H), 4.95 (d, J=12 Hz, 1H), 5.03 (d, J=18.5 Hz, 1H), 5.15 (d, J=12 Hz, 1H), 5.32 (d, J=18.5 Hz, 1H), 5.75-5.84 (m, 2H), 7.38-7.39 (m, 1H), 7.45-7.48 (m, 2H), 7.53-7.58 (m, 2H), 7.63-7.71 (m, 4H);

LC-MS (retention time: 3.15 min, method B), MS m/z 763 (M$^+$+H).

Example 108

Preparation of Compound 108

Compound 108

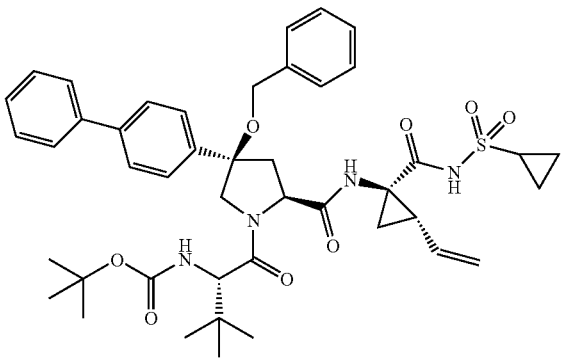

Scheme 4
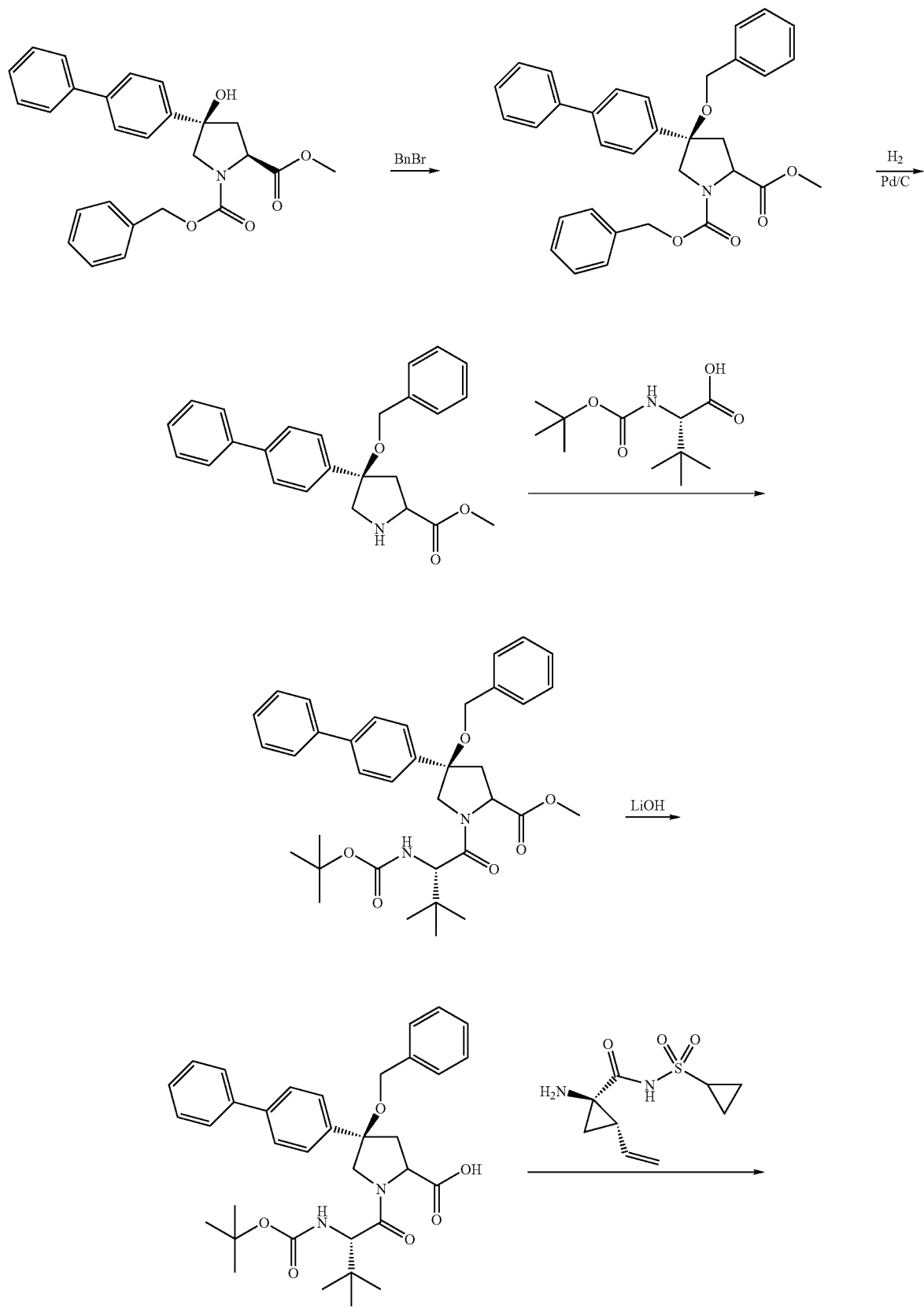

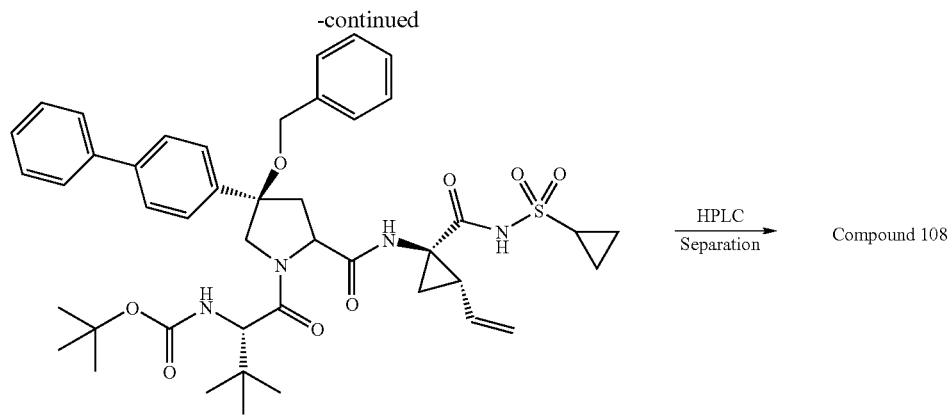

→ HPLC Separation → Compound 108

Step 1

Sodium hydride 60% oil dispersion (40.0 mg, 1.000 mmol) was rinsed with hexane and was stirred in DMF (5 mL). (2S,4R)-1-benzyl 2-methyl 4-(biphenyl-4-yl)-4-hydroxypyrrolidine-1,2-dicarboxylate (216 mg, 0.5 mmol) was added as a solid in one portion at 0° C. The formed light yellow solution was stirred at this temperature for 30 min before addition of benzyl bromide (0.072 mL, 0.600 mmol). The final solution was stirred at 0° C. for 2 h. Quenched with iced 5% citric acid, extracted with EtOAc. Washed the organic layer with brine, dried over MgSO$_4$, filtered and evaporated. The residue was purified by silica gel column, eluted with 4:1, 3:1, then 2:1 hexane-EtOAc to afford 64 mg (24% yield) of the desired product as a mixture of diastereomers and 150 mg of the starting material.

$^1$H NMR (CDCl$_3$) δ 2.28-2.34 (m, 0.5H), 2.51-2.60 (m, 0.5H), 2.90-3.02 (m, 1H), 3.41, 3.55, 3.56, 3.78 (s, 3H), 3.82-3.99 (m, 1H), 4.11-4.23 (m, 3H), 4.41-4.70 (m, 1H), 5.09-5.29 (m, 2H), 7.17-7.63 (m, 19H);

LC-MS (retention time: 3.18 min, method B), MS m/z 522 (M$^+$+H).

Step 2

To an iced Parr shaker vessel containing solution of (4R)-1-benzyl 2-methyl 4-(benzyloxy)-4-(biphenyl-4-yl)pyrrolidine-1,2-dicarboxylate (58 mg, 0.111 mmol) in ethyl acetate (1 mL) and MeOH (1 mL) was added palladium (12 mg, 0.011 mmol) on carbon (10%, wet). The vessel was placed on Parr shaker apparatus under hydrogen with 25 psi pressure for 3 h. Quenched with celite. Filtered, evaporated to afford the desired product (38 mg, 88% yield) as an off-white powder. This material was used for the following coupling reaction without further purification.

LC-MS (retention time: 2.36 min, method B), MS m/z 388 (M$^+$+H).

Step 3

To a solution of (4R)-methyl 4-(benzyloxy)-4-(biphenyl-4-yl)pyrrolidine-2-carboxylate (60 mg, 0.155 mmol), (S)-2-(tert-butoxycarbonylamino)-3,3-dimethylbutanoic acid (39.3 mg, 0.17 mmol), and HATU (84 mg, 0.232 mmol) in DCM (2 ml) was added N,N-Diisopropylethylamine (0.081 ml, 0.465 mmol) at 0° C. The formed solution was stirred at room temperature overnight. Diluted with DCM, washed with 5% citric acid and brine, dried over MgSO$_4$, filtered and evaporated. The residue was purified by silica gel column, eluted with 3:1 hexane-acetone to afford the desired product (77 mg, 83% yield) as white foam.

$^1$H NMR (CDCl$_3$) δ 1.04, 1.11 (s, 9H), 1.42, 1.43 (s, 9H), 2.38-2.40 (m, 0.5H), 2.55-2.60 (m, 0.5H), 2.90-3.02 (m, 1H), 3.52, 3.75 (s, 3H), 4.10-4.18 (m, 2H), 4.24-4.26 (m, 1H), 4.34-4.38 (m, 1H), 4.63-4.64 (m, 0.5H), 4.80-4.82 (m, 0.5H), 5.20-5.29 (m, 1H), 7.16-7.61 (m, 14H);

LC-MS (retention time: 3.28 min, method B), MS m/z 601 (M$^+$+H).

Step 4

To a solution of (4R)-methyl 4-(benzyloxy)-4-(biphenyl-4-yl)-1-((S)-2-(tert-butoxycarbonylamino)-3,3-dimethylbutanoyl)pyrrolidine-2-carboxylate (74 mg, 0.123 mmol) in THF (1 mL) and MeOH (1 mL) was added pre-made solution of lithium hydroxide monohydrate (15.5 mg, 0.370 mmol) in water (1 mL). The formed cloudy solution was stirred at room temperature overnight. Removed the volatiles in vacuo. The residue taken up in water, acidified with 1M HCl to pH 2. Extracted with EtOAc. Washed the organic layer with 5% citric acid and brine, dried over MgSO$_4$, filtered and evaporated. The residual white solid (58 mg, 80% yield) was used for the next coupling reaction without further purification.

LC-MS (retention time: 3.19 min, method B), MS m/z 587 (M$^+$+H).

Step 5

To a slurry of (4R)-4-(benzyloxy)-4-(biphenyl-4-yl)-1-((S)-2-(tert-butoxycarbonylamino)-3,3-dimethylbutanoyl)pyrrolidine-2-carboxylic acid (63 mg, 0.107 mmol), (1R,2S)-1-amino-N-(cyclopropylsulfonyl)-2-vinylcyclopropanecarboxamide, tosylic acid, hydrate (49.7 mg, 0.118 mmol), and HATU (58.0 mg, 0.161 mmol) in dichloromethane (2 mL) was added N,N-Diisopropylethylamine (0.056 mL, 0.322 mmol) at 0° C. The final mixture was stirred at room temperature overnight. Diluted with DCM, washed with 5% citric acid and brine, dried over MgSO$_4$, filtered and evaporated. The residue was purified by preparative HPLC (MeOH-water as eluent) to yield a mixture of diastereomeric products (48 mg, 55.9% yield) as white solid. This solid was re-subjected to another preparative HPLC condition (acetonitrile-water as eluent) to obtain the homochiral product (11 mg).

$^1$H NMR (CD$_3$OD) δ 1.05-1.15 (m, 11H), 1.25-1.31 (m, 2H), 1.47-1.50 (m, 10H), 1.80-1.82 (m, 1H), 2.15-2.20 (m,

1H), 2.57-2.70 (m, 2H), 2.94-2.98 (m, 1H), 4.08-4.19 (m, 2H), 4.30 (s, 2H), 4.45 (d, J=9 Hz, 1H), 4.72-4.76 (m, 1H), 5.13 (d, J=12 Hz, 1H), 5.28 (d, J=18.5 Hz, 1H), 5.75-5.82 (m, 1H), 7.29-7.34 (m, 6H), 7.38-7.40 (m, 2H), 7.63-7.69 (m, 6H);

LC-MS (retention time: 3.22 min, method B), MS m/z 799.5 (M$^+$+H).

Example 109

Preparation of Compound 109

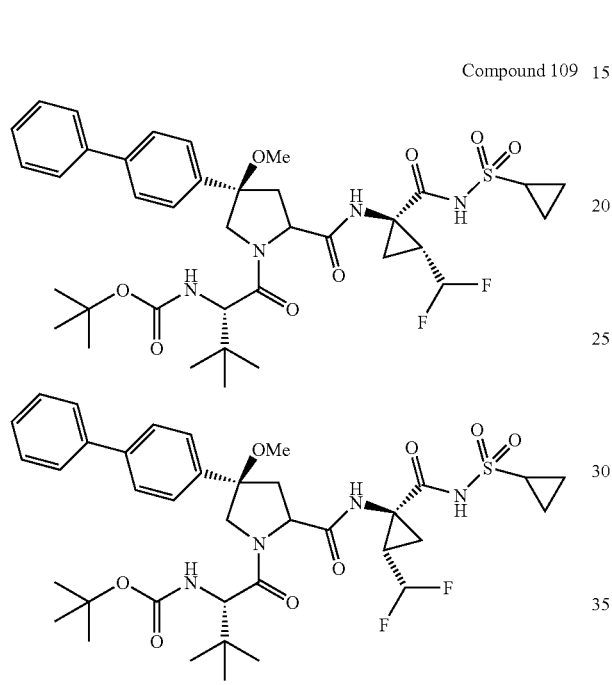

Compound 109

Approximately a 1:1 mixture of P1 isomers

Step 1: Preparation of (E/Z)methyl 2-(benzyloxycarbonylamino)-4,4-difluorobut-2-enoate

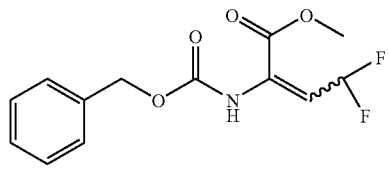

To a suspension of potassium tert-butoxide (3.91 g, 34.9 mmol) in tetrahydrofuran (50 mL) was added methyl 2-(benzyloxycarbonylamino)-2-(dimethoxyphosphoryl)acetate (10.5 g, 31.7 mmol) at −78° C. under N$_2$. It was stirred for 30 min at this temperature and then 1-ethoxy-2,2-difluoroethanol (7.99 g, 63.4 mmol) was added slowly. The resulting mixture was warmed up to rt and stirred for 18 h. It was then quenched with water, adjusted to pH=5 by adding a few drops of 1 N HCl. The mixture was extracted with EtOAc. The organic layer was dried over MgSO$_4$, filtered and concentrated to yield 10 g of the crude product as a yellow oil. Purification by Biotage eluting with 30% EtOAc/Hexane gave 7.12 g (79%) of (E/Z)methyl 2-(benzyloxycarbonylamino)-4,4-difluorobut-2-enoate as an oil. LC-MS, about 1:8 mixture of isomers. LC-MS, MS m/z 286 (M+1). Major isomer: $^1$H NMR (500 MHz, CDCl$_3$) δ ppm 3.84 (s, 3H), 5.18 (s, 2H), 6.21-6.43 (m, 1H), 6.70 (dt, J$_1$=55.2 Hz, J$_2$=5.19, 1H), 6.90-7.05 (brs, 1H), 7.31-7.50 (m, 5H).

Step 2: Preparation of (E/Z)-methyl 2-((benzyloxycarbonyl)(tert-butoxycarbonyl)amino)-4,4-difluorobut-2-enoate, shown below

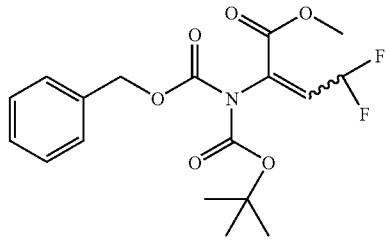

A solution of (E/Z)methyl 2-(benzyloxycarbonylamino)-4,4-difluorobut-2-enoate (19 g, 66.6 mmol), di-tert-butyl dicarbonate (29.1 g, 133 mmol) and a catalytic amount of DMAP (0.814 g, 6.66 mmol) in tetrahydrofuran (200 mL) was stirred at rt for 2 h. It was then diluted with EtOAc, washed with water, dried over MgSO$_4$, filtered and concentrated to yield 39.1 g of the crude product as a colorless oil. Purification by Biotage eluting with 25% EtOAc/hexane gave 22 g (86%) of (E/Z)-methyl 2-((benzyloxycarbonyl)(tert-butoxycarbonyl)amino)-4,4-difluorobut-2-enoate a colorless oil.

LC-MS, MS m/z 408 (M+1+Na). Major isomer: $^1$H NMR (500 MHz, CDCl$_3$) δ ppm 1.45 (s, 9H), 3.73 (s, 3H), 5.21 (s, 2H), 6.12-6.39 (dt, J$_1$=54.3 Hz, J$_2$=6.10 Hz, 1H), 6.72-6.81 (m, 1H), 7.29-7.41 (m, 5H).

Step 3: Preparation of methyl 1-((benzyloxycarbonyl)(tert-butoxycarbonyl)amino)-2-(difluoromethyl)cyclopropanecarboxylate

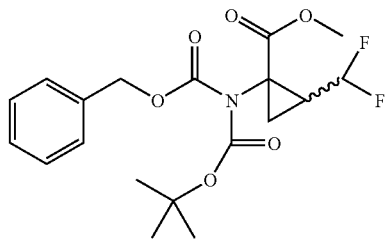

To a mixture of sodium hydride (0.850 g, 21.26 mmol) in DMSO (50 ml) was added trimethylsulfoxonium iodide (4.90 g, 22.25 mmol) and the mixture was stirred at rt for 1 h. Then (E/Z)-methyl 2-((benzyloxycarbonyl)(tert-butoxycarbonyl)amino)-4,4-difluorobut-2-enoate (6.4 g, 16.61 mmol) was added and the mixture was heated at 80° C. for 2 h. The reaction was then cooled to rt and stirred for 18 h. Water (10 mL) was added followed by 1N HCl to adjust the pH to 5. This mixture was extracted with EtOAc (3×250 mL). The organic layer was washed with water (20 mL), dried over MgSO$_4$, filtered, concentrated to yield 7 g of the crude product as a yellow oil. Purification by Biotage eluting with 15% EtOAc/ hexane gave 0.8 g of methyl 1-((benzyloxycarbonyl)(tert-butoxycarbonyl)amino)-2-(difluoromethyl)cyclopropanecarboxylate as an oil. LC-MS, MS m/z 422 (M+1+Na). Another 1.35 g of the des-Cbz product, methyl 1-(tert-butoxycarbonylamino)-2-(difluoromethyl)cyclopropanecarboxylate, was also obtained from the Biotage purification as an oil. LC-MS, MS m/z 288 (M+1+Na). The combined yield is 42%.

Step 4: Preparation of 1-(tert-butoxycarbonylamino)-2-(difluoromethyl)cyclopropanecarboxylic acid

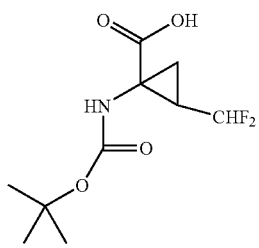

A mixture of methyl 1-((benzyloxycarbonyl)(tert-butoxycarbonyl)amino)-2-(difluoromethyl)cyclopropanecarboxylate (1.05 g, 2.63 mmol), methyl 1-(tert-butoxycarbonylamino)-2-(difluoromethyl)cyclopropanecarboxylate (1.43 g, 5.39 mmol) in MeOH (20 mL) and sodium hydroxide (10 mL, 40.0 mmol) was stirred at rt for 18 h. The reaction mixture was concentrated and adjusted to pH=4 using 1N HCl. A white solid precipitated from the solution and was collected by filteration. The filter cake was washed with water to yield 1.2 g of the crude product as a white solid. Crystallization from hexane/EtOAc gave 1.0 g (50%) of 1-(tert-butoxycarbonylamino)-2-(difluoromethyl)cyclopropanecarboxylic acid as a white solid. This intermediate was isolated as a single diastereoisomer wherein the $CF_2H$ substituent is syn to the carboxyl group.

LC-MS, MS m/z 274 (M+1+Na).
$^1$H NMR (300 MHz, d-4-MeOH) δ ppm 1.31-1.54 (m, 10H) 1.66-1.86 (m, 1H) 1.85-2.10 (m, 1H) 5.92 (t, J=55.81 Hz, 1H).

Step 5: Preparation of tert-butyl 1-(cyclopropylsulfonylcarbamoyl)-2-(difluoromethyl)cyclopropylcarbamate

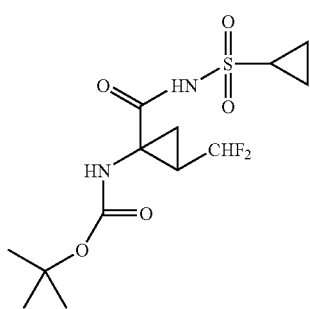

A mixture of 1-(tert-butoxycarbonylamino)-2-(difluoromethyl)cyclopropanecarboxylic acid (975 mg, 3.88 mmol) and CDI (755 mg, 4.66 mmol) in tetrahydrofuran (10 mL) was heated at reflux for 1 h. It was then cooled to rt and then cyclopropanesulfonamide (564 mg, 4.66 mmol) was added, followed by DBU (0.702 mL, 4.66 mmol). This mixture was stirred at rt for 18 h. It was then concentrated in vacuo, diluted with water and adjusted to pH=4 using 1 N HCl. The acidic solution was extracted with EtOAc, washed with water (5×15 mL), dried (MgSO$_4$), and concentrated in vacuo to yield 1.6 g of the crude product as a white solid. Recrystallization from hexane/EtOAc gave 1.15 g (84%) of tert-butyl 1-(cyclopropylsulfonylcarbamoyl)-2-(difluoromethyl)cyclopropylcarbamate as a white solid. LC-MS, MS m/z 377 (M+1+Na).

$^1$H NMR (500 MHz, d-4-MeOH) δ ppm 1.03-1.17 (m, 2H), 1.18-1.25 (m, 1H), 1.25-1.35 (m, 1H), 1.39-1.46 (m, J=5.49 Hz, 1H), 1.49 (s, 9H), 1.90-2.03 (m, 1 H), 2.04-2.20 (m, 1H), 2.99 (s, 1H), 5.50-5.89 (m, 1H).

Step 6: Preparation of 1-amino-N-(cyclopropylsulfonyl)-2-(difluoromethyl)cyclopropanecarboxamide, HCl salt

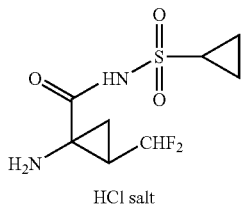

HCl salt

A mixture of tert-butyl 1-(cyclopropylsulfonylcarbamoyl)-2-(difluoromethyl)cyclopropylcarbamate (1.1 g, 3.10 mmol) and 4N HCl/dioxane (10 mL) was stirred at rt for 2 h. The reaction mixture was then concentrated to yield 0.93 g (103%) of 1-amino-N-(cyclopropylsulfonyl)-2-(difluoromethyl)cyclopropanecarboxamide, HCl salt as a white solid.

LC-MS, MS m/z 277 (M+1+Na). $^1$H NMR (500 MHz, d-4-MeOH) δ ppm 1.07-1.21 (m, 2H) 1.20-1.37 (m, 2H) 1.70-1.85 (m, 1H) 2.21-2.36 (m, 2H) 2.96-3.11 (m, 1H) 5.86-6.13 (dt, J$_1$=55.24 Hz, J$_2$=5.19 Hz, 1H).

Step 7: Preparation of Compound 109

A mixture of (2S,4R)-4-(biphenyl-4-yl)-1-((S)-2-(tert-butoxycarbonylamino)-3,3-dimethylbutanoyl)-4-methoxypyrrolidine-2-carboxylic acid (30 mg, 0.059 mmol), 1-amino-N-(cyclopropylsulfonyl)-2-(difluoromethyl)cyclopropanecarboxamide, HCl salt (17.08 mg, 0.059 mmol), HATU (26.8 mg, 0.071 mmol) and 1-methylpiperidine (29.1 mg, 0.294 mmol) in DCM (3 mL) was stirred at rt for 18 h. It was then concentrated in vacuo. The residue was partitioned between EtOAc (50 mL) and 5 mL of water adjusted to pH=4 using 1N HCl. The organic phase was then washed with water (3×5 mL), dried (MgSO$_4$), filtered and concentrated to yield 50 mg of the crude product as a white solid. Purification by preparative HPLC gave 38 mg of Compound 109 as a white solid (~1:1 mixture of two P1 diasteromers). LC-MS, MS m/z 747 (M+1).

$^1$H NMR (500 MHz, d-4-MeOH) δ ppm 0.82-1.68 (m, 23H), 1.89-1.91 (m, 2H), 2.41-2.74 (m, 2H), 2.92-3.05 (m, 1H), 3.05-3.21 (m, 3H), 3.98-4.17 (m, 1H), 4.13-4.29 (m, 1H), 4.27-4.49 (m, 1H), 4.49-4.73 (m, 1H), 5.67-6.14 (m, 1H), 7.38 (t, J=7.32 Hz, 1H), 7.47 (t, J=7.32 Hz, 2H), 7.52-7.81 (m, 6H).

Example 110
Preparation of Compound 110
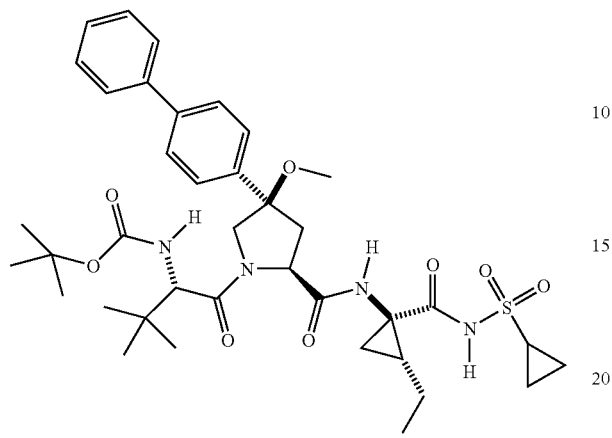
Compound 110
Intermediate 111: Preparation of Compound 111
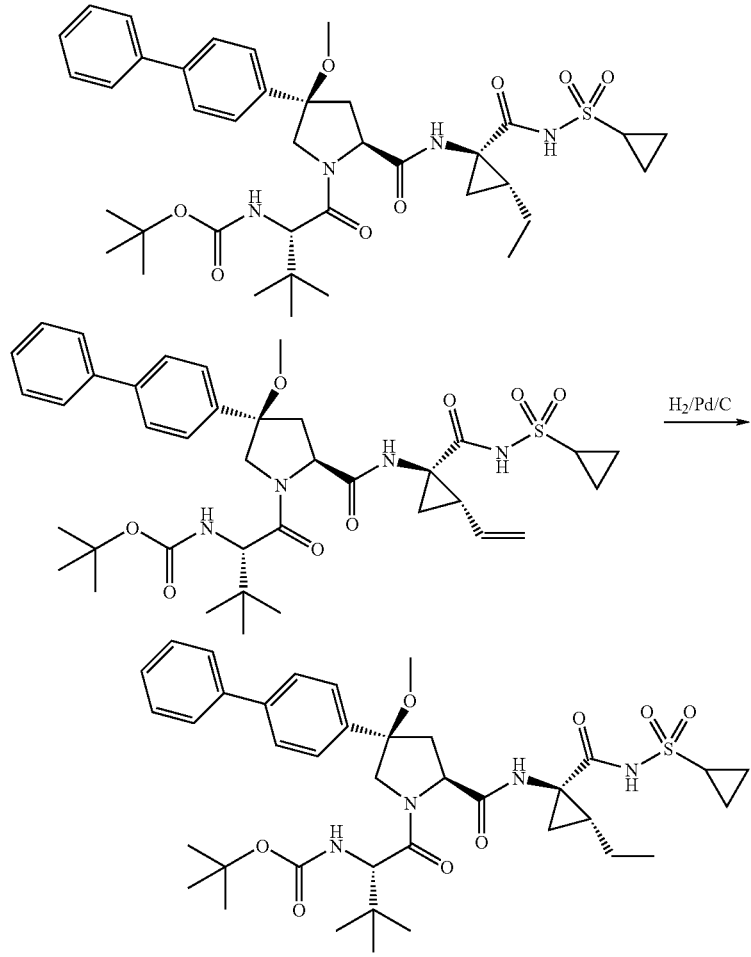
Compound 111

To an iced Parr shaker vessel containing solution of tert-butyl (S)-1-((2S,4R)-4-(biphenyl-4-yl)-2-((1R,2S)-1-(cyclopropylsulfonylcarbamoyl)-2-vinylcyclopropylcarbamoyl)-4-methoxypyrrolidin-1-yl)-3,3-dimethyl-1-oxobutan-2-ylcarbamate in EtOAc (1 mL) was added Palladium (2.061 mg, 1.937 μmol) on carbon (10%, wet). The vessel was placed on Parr shaker under hydrogen with 10 psi pressure for 2 h. Quenched with celite. Filtered, evaporated. The residue was purified by prep-HPLC to yield the desired product (6 mg, 43% yield) as a white solid. $^1$H NMR (CD$_3$OD) δ 0.98-1.02 (m, 4H), 1.10-1.14 (m, 10H), 1.26-1.35 (m, 4H), 1.29-1.62 (m, 12H), 2.48-2.51 (m, 1H), 2.55-2.61 (m, 1H), 2.95-2.99 (m, 1H), 3.11 (s, 3H), 4.07-4.09 (m, 1H), 4.22-4.24 (m, 1H), 4.42 (s, 1H), 4.58-4.60 (m, 1H), 7.38-7.39 (m, 1H), 7.45-7.48 (m, 2H), 7.57-7.67 (m, 6H);

LC-MS (retention time: 3.00 min, method B), MS m/z 725 (M$^+$+H), 693 (M$^+$-MeOH).

Example 200

Preparation of Compound 200

Compound 200

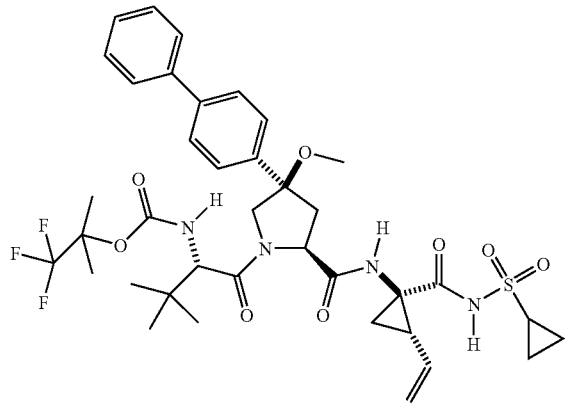

Step 1: Preparation of (S)-3,3-Dimethyl-2-(2,2,2-trifluoro-1,1-dimethyl-ethoxycarbonylamino)-butyric acid

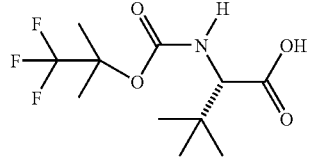

Step 1a: Preparation of carbonic acid pyridin-2-yl ester 2,2,2-trifluoro-1,1-dimethyl-ethyl ester

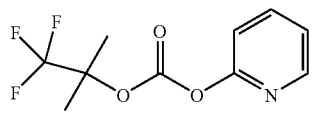

To a slurry of KH (1.03 g, 25.8 mmol) in THF (70 mL) was added 1,1,1-trifluoro-2-methylpropan-2-ol (3 g, 23.42 mmol). The reaction was stirred at 0° C. for 20 min. A solution of dipyridin-2-yl carbonate (5.06 g, 23.42 mmol) in THF (30 mL) was then added to the mixture. The mixture was stirred at rt for overnight. A lot of solid came out from the solution. The solid was filtered and washed with EtOAc (30 mL). The combined THF/EtOAc solution was washed with water. The organic layer was dried over Na$_2$SO$_4$, filtered and concentrated. The obtained white solid (1.24 g, 21%) was directly used for the next step.

Step 1b: Preparation of (S)-3,3-Dimethyl-2-(2,2,2-trifluoro-1,1-dimethyl-ethoxycarbonylamino)-butyric acid methyl ester

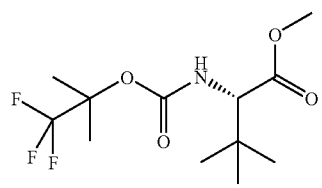

To an ice-cooled solution of (S)-methyl 2-amino-3,3-dimethylbutanoate (0.411 g, 2.262 mmol) in DCM (20 mL) was added N,N-Diisopropylethylamine (1.182 mL, 6.79 mmol). The formed solution was stirred for 5 min before addition of carbonic acid pyridin-2-yl ester 2,2,2-trifluoro-1,1-dimethyl-ethyl ester (1.24 g, 4.98 mmol, from step 1a) in DCM (10 mL). The final light yellow solution was stirred at room temperature overnight. The reaction mixture was washed with 5% citric acid aqueous solution, 0.1 M NaOH aqueous solution, and brine, then dried over Na$_2$SO$_4$, filtered, and evaporated to dryness. The residue was purified by silica gel column, eluted with (4:1) hexane-EtOAc to afford a colorless oil as the product (673 mg, 99%).

$^1$H-NMR (CDCl$_3$-d) δ 0.96 (s, 9H), 1.65 (s, 6H), 3.73 (s, 3H), 5.31 (m, 1H); LCMS RT=2.72 min, [M+Na]$^+$=322.3.

Step 1c: Preparation of (S)-3,3-Dimethyl-2-(2,2,2-trifluoro-1,1-dimethyl-ethoxycarbonylamino)-butyric acid

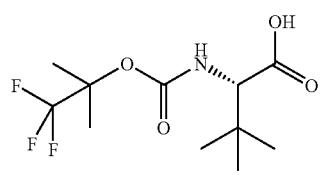

To a solution of (S)-3,3-Dimethyl-2-(2,2,2-trifluoro-1,1-dimethyl-ethoxycarbonylamino)-butyric acid methyl ester (673 mg, 2.249 mmol, from Step 1b) in THF (4 mL) was added to a pre-made solution of lithium hydroxide monohydrate (189 mg, 4.50 mmol) in water (4.00 mL). The cloudy white solution was stirred at rt for 5 hrs. Another 100 mg of LiOH in 1 mL water was added to the mixture and the solution was stirred at rt overnight. The volatiles were removed, and the reaction mixture was diluted with 5% citric acid aqueous solution, and extracted with EtOAc (3×10 mL). The organic layer was washed with brine, dried over Na$_2$SO$_4$, filtered and evaporated. The crude material (325 mg, 51%) as white solid was used in the next step reaction without further purification.

LCMS RT=2.55 min, [M+Na]$^+$=308.2.

Step 2: Preparation of (2S,4R)-4-Biphenyl-4-yl-1-[(S)-3,3-dimethyl-2-(2,2,2-trifluoro-1,1-dimethyl-ethoxycarbonylamino)-butyryl]-4-methoxy-pyrrolidine-2-carboxylic acid methyl ester

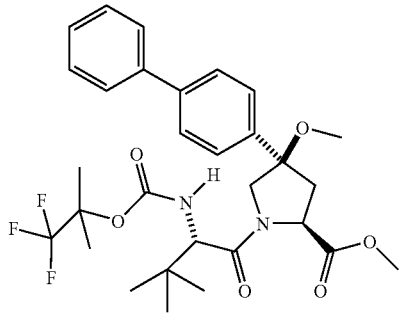

This material was prepared by the same procedure as described in Example 106, except using (S)-3,3-Dimethyl-2-(2,2,2-trifluoro-1,1-dimethyl-ethoxycarbonylamino)-butyric acid instead of (S)-2-(tert-butoxycarbonylamino)-3,3-dimethylbutanoic acid as starting material in step 5.

$^1$H NMR (CD$_3$OD) δ 1.11 (s, 9H), 1.57 (s, 3H), 1.62 (s, 3H), 2.59 (m, 1H), 2.76 (m, 1H), 2.94 (s, 3H), 3.71 (s, 3H), 4.12 (m, 1H), 4.21 (m, 1H), 4.29 (m, 1H), 4.72 (m, 1H), 7.31-7.68 (m, 9H); LCMS RT=3.33 min, [M+Na]$^+$=601.2.

Step 3: Preparation of (2S,4R)-4-Biphenyl-4-yl-1-[(S)-3,3-dimethyl-2-(2,2,2-trifluoro-1,1-dimethyl-ethoxycarbonylamino)-butyryl]-4-methoxy-pyrrolidine-2-carboxylic acid

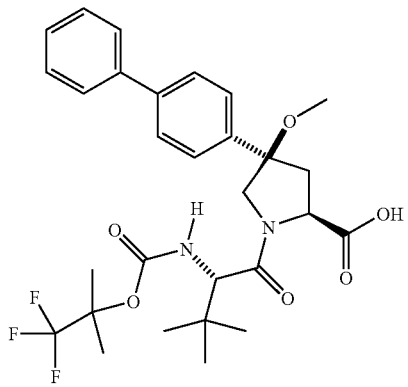

This material was prepared by the same procedure as described in Example 106 step 6 except using (2S,4R)-4-Biphenyl-4-yl-1-[(S)-3,3-dimethyl-2-(2,2,2-trifluoro-1,1-dimethyl-ethoxycarbonylamino)-butyryl]-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.26 min, [M+Na]$^+$=587.2.

Step 4: Preparation of {(S)-1-[(2S,4R)-4-Biphenyl-4-yl-2-((S)-(1R,2S)-1-cyclopropanesulfonylaminocarbonyl-2-vinyl-cyclopropylcarbamoyl)-4-methoxy-pyrrolidine-1-carbonyl]-2,2-dimethyl-propyl}-carbamic acid 2,2,2-trifluoro-1,1-dimethyl-ethyl ester Compound 200

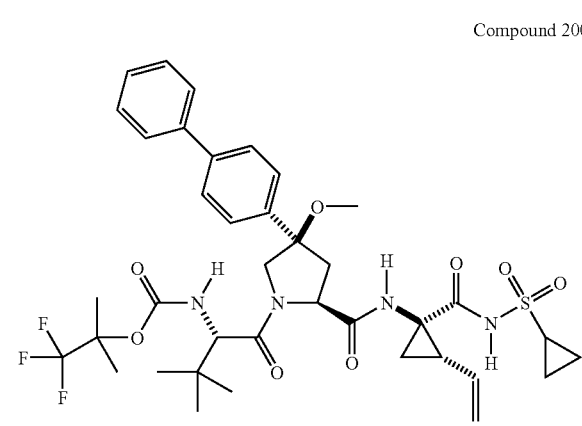

Compound 200 was prepared by the same procedure as described in Example 106 step 7 except using (2S,4R)-4-Biphenyl-4-yl-1-[(S)-3,3-dimethyl-2-(2,2,2-trifluoro-1,1-dimethyl-ethoxycarbonylamino)-butyryl]-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

$^1$H NMR (CD$_3$OD) δ 1.12 (s, 9H), 1.30-1.26 (m, 4H), 1.43 (m, 1H), 1.64 (s, 3H), 1.69 (s, 3H), 1.88 (m, 1H), 2.22 (m, 1H), 2.49 (m. 1H), 2.62 (m, 1H), 2.96 (m, 1H), 3.11 (s, 3H), 4.07 (m, 1H), 4.23 (m, 1H), 4.42 (d, J=9 Hz, 1H), 4.56 (m, 1H), 5.15 (d, J=12 Hz, 1H), 5.32 (d, J=18.5 Hz, 1H), 5.74 (m, 1H), 7.36-7.70 (m, 9H);

LCMS RT=3.24 min, [M+Na]$^+$=799.3.

Example 201

Preparation of Compound 201

Compound 201

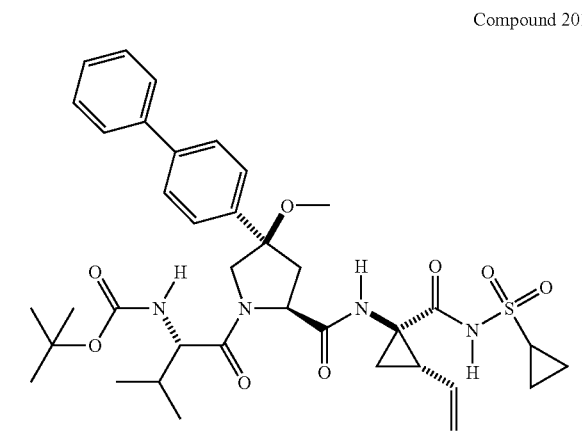

Step 1: Preparation of (2S,4R)-4-Biphenyl-4-yl-1-((S)-2-tert-butoxycarbonylamino-3-methyl-butyryl)-4-methoxy-pyrrolidine-2-carboxylic acid methyl ester

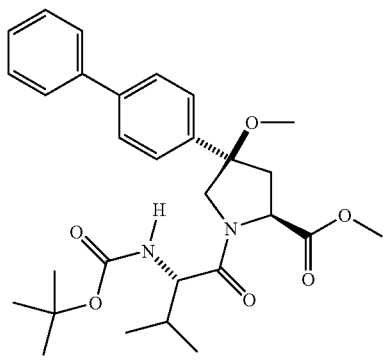

This material was prepared by the same procedure as described in Example 106, except using (S)-2-(tert-butoxycarbonylamino)-3-methylbutanoic acid (commercially available from Aldrich) instead of (S)-2-(tert-butoxycarbonylamino)-3,3-dimethylbutanoic acid as starting material in step 5.

LCMS RT=3.22 min, [M+Na]⁺=533.4.

Step 2: Preparation of (2S,4R)-4-Biphenyl-4-yl-1-((S)-2-tert-butoxycarbonylamino-3-methyl-butyryl)-4-methoxy-pyrrolidine-2-carboxylic acid

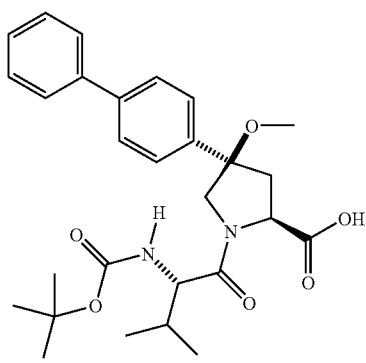

This material was prepared by the same procedure as described in Example 106 step 6 except using (2S,4R)-4-Biphenyl-4-yl-1-((S)-2-tert-butoxycarbonylamino-3-methyl-butyryl)-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.07 min, [M+H]⁺=497.4.

Step 3: Preparation of {(S)-1-[(2S,4R)-4-Biphenyl-4-yl-2-((S)-(1R,2S)-1-cyclopropanesulfonylaminocarbonyl-2-vinyl-cyclopropylcarbamoyl)-4-methoxy-pyrrolidine-1-carbonyl]-2-methyl-propyl}-carbamic acid tert-butyl ester

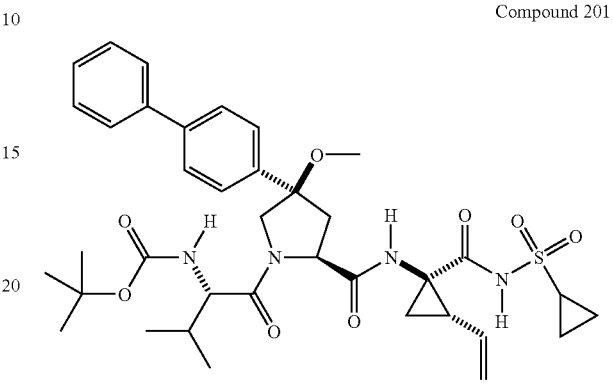

Compound 201

Compound 201 was prepared by the same procedure as described in Example 106 step 7 except using (2S,4R)-4-Biphenyl-4-yl-1-((S)-2-tert-butoxycarbonylamino-3-methyl-butyryl)-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

¹H NMR (CD₃OD) δ 0.87 (m, 1H), 0.93 (m, 1H), 1.00 (m, 4H), 1.07 (m, 2H), 1.18-1.30 (m, 4H), 1.38 (m, 2H), 1.43 (m, 6H), 1.85 (m, 1H), 2.08 (m, 1H), 2.22 (m, 1H), 2.49 (m, 1H), 2.53 (m, 1H), 2.96 (m, 1H), 3.07 (s, 3H), 4.06 (m, 1H), 4.12 (m, 1H), 4.22 (t, 1H), 4.54 (d, J=9 Hz, 1H), 5.10 (d, J=12 Hz, 1H), 5.27 (d, J=18.5 Hz, 1H), 5.74 (m, 1H), 7.36-7.70 (m, 9H); LCMS RT=3.11 min, [M+Na]⁺=731.2.

Example 202

Preparation of Compound 202

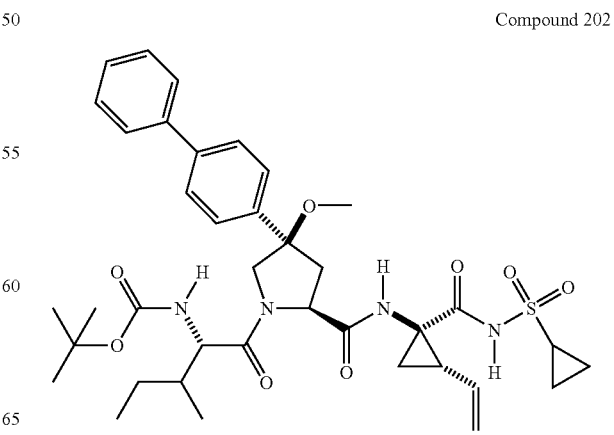

Compound 202

Step 1: Preparation of (2S,4R)-4-Biphenyl-4-yl-1-((S)-2-tert-butoxycarbonylamino-3-methyl-pentanoyl)-4-methoxy-pyrrolidine-2-carboxylic acid methyl ester

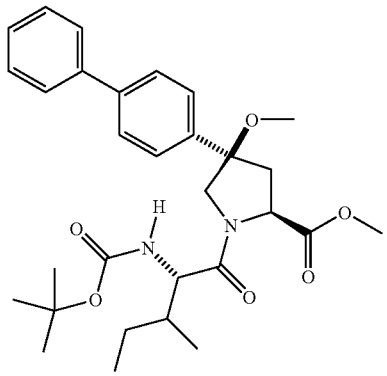

This material was prepared by the same procedure as described in Example 106, except using (2S)-2-(tert-butoxycarbonylamino)-3-methylpentanoic acid (commercial available material from Aldrich) instead of (S)-2-(tert-butoxycarbonylamino)-3,3-dimethylbutanoic acid as starting material in step 5.

LCMS RT=3.27 min, [M+Na]⁺=547.4.

Step 2: Preparation of (2S,4R)-4-Biphenyl-4-yl-1-((S)-2-tert-butoxycarbonylamino-3-methyl-pentanoyl)-4-methoxy-pyrrolidine-2-carboxylic acid

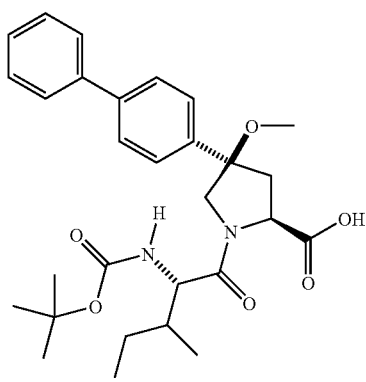

This material was prepared by the same procedure as described in Example 106 step 6 except using (2S,4R)-4-Biphenyl-4-yl-1-((S)-2-tert-butoxycarbonylamino-3-methyl-butyryl)-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.15 min, [M+H]⁺=511.5.

Step 3: Preparation of {(S)-1-[(2S,4R)-4-Biphenyl-4-yl-2-((S)-(1R,2S)-1-cyclopropanesulfonylaminocarbonyl-2-vinyl-cyclopropylcarbamoyl)-4-methoxy-pyrrolidine-1-carbonyl]-2-methyl-butyl}-carbamic acid tert-butyl ester

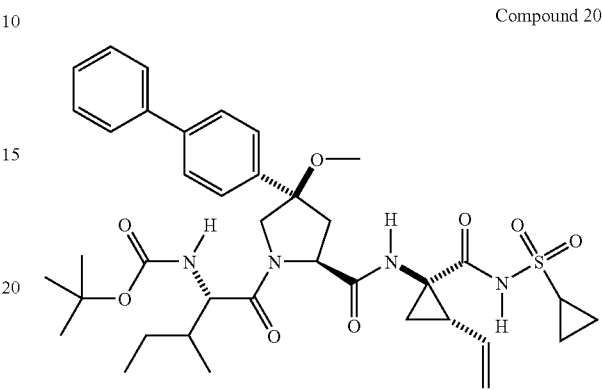

Compound 202

Compound 202 was prepared by the same procedure as described in Example 106 step 7 except using (2S,4R)-4-Biphenyl-4-yl-1-((S)-2-tert-butoxycarbonylamino-3-methyl-pentanoyl)-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

¹H NMR (CD₃OD) δ 0.91-0.97 (m, 4H), 1.03 (m, 2H), 1.10 (m, 2H), 1.20-1.34 (m, 5H), 1.40-1.50 (m, 9H), 1.68 (m, 1H), 1.88 (m, 1H), 2.25 (m. 1H), 2.56 (m, 2H), 2.98 (m, 1H), 3.11 (s, 3H), 4.10 (m, 1H), 4.22 (m, 2H), 4.63 (d, J=9 Hz, 1H), 5.15 (d, J=12 Hz, 1H), 5.32 (d, J=18.5 Hz, 1H), 5.74 (m, 1H), 7.36-7.70 (m, 9H); LCMS RT=3.24 min, [M+Na]+=745.3.

Example 203

Preparation of Compound 203

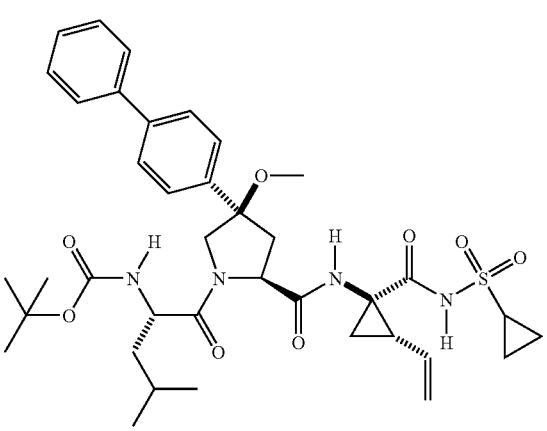

Compound 203

Step 1: Preparation of (2S,4R)-4-Biphenyl-4-yl-1-((S)-2-tert-butoxycarbonylamino-4-methyl-pentanoyl)-4-methoxy-pyrrolidine-2-carboxylic acid methyl ester

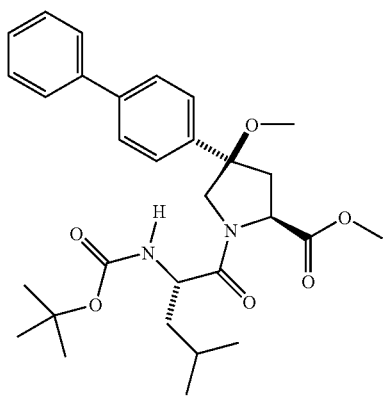

This material was prepared by the same procedure as described in Example 106, except using (S)-2-(tert-butoxycarbonylamino)-4-methylpentanoic acid (commercially available from Aldrich) instead of (S)-2-(tert-butoxycarbonylamino)-3,3-dimethylbutanoic acid as starting material in step 5.

LCMS RT=3.26 min, [M+Na]⁺=547.4.

Step 2: Preparation of (2S,4R)-4-Biphenyl-4-yl-1-((S)-2-tert-butoxycarbonylamino-4-methyl-pentanoyl)-4-methoxy-pyrrolidine-2-carboxylic acid

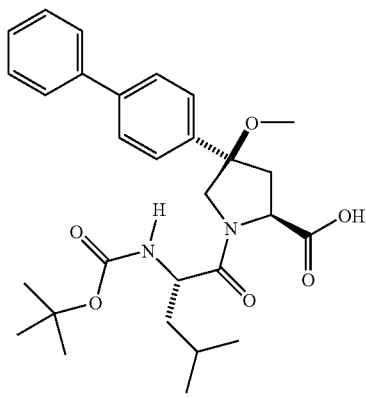

This material was prepared by the same procedure as described in Example 106 step 6 except using (2S,4R)-4-Biphenyl-4-yl-1-((S)-2-tert-butoxycarbonylamino-3-methyl-butyryl)-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.16 min, [M+Na]⁺=533.5.

Step 3: Preparation of {(S)-1-[(2S,4R)-4-Biphenyl-4-yl-2-((S)-(1R,2S)-1-cyclopropanesulfonylaminocarbonyl-2-vinyl-cyclopropylcarbamoyl)-4-methoxy-pyrrolidine-1-carbonyl]-3-methyl-butyl}-carbamic acid tert-butyl ester

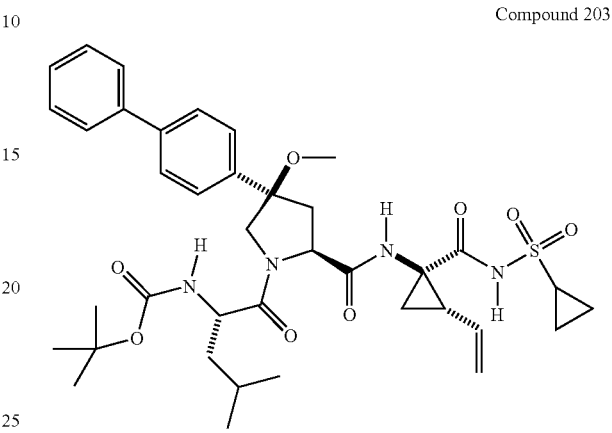

Compound 203

Compound 203 was prepared by the same procedure as described in Example 106 step 7 except using (2S,4R)-4-Biphenyl-4-yl-1-((S)-2-tert-butoxycarbonylamino-4-methyl-pentanoyl)-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

$^1$H NMR (CD$_3$OD) δ 0.91-0.98 (m, 2H), 1.02 (m, 4H), 1.24-1.32 (m, 6H), 1.39-1.48 (m, 9H), 1.64 (m, 1H), 1.76 (m, 1H), 1.88 (m, 1H), 2.30 (m. 1H), 2.62 (m, 2H), 2.98 (m, 1H), 3.11 (s, 3H), 4.11 (m, 1H), 4.18 (d, J=9 Hz, 1H), 4.37 (m, 1H), 4.49 (m, 1H), 5.15 (d, J=12 Hz, 1H), 5.32 (d, J=18.5 Hz, 1H), 5.74 (m, 1H), 7.36-7.70 (m, 9H); LCMS RT=3.24 min, [M+Na]⁺=745.3.

Example 204

Preparation of Compound 204

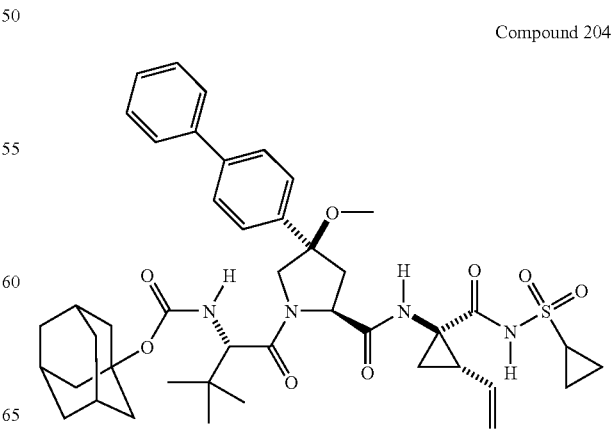

Compound 204

Step 1a: Preparation of (S)-2-(Adamantan-1-yloxy-carbonylamino)-3,3-dimethyl-butyric acid methyl ester

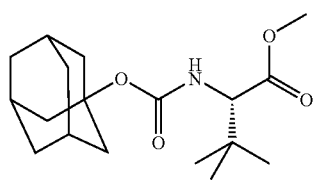

To a mixture of (S)-methyl 2-amino-3,3-dimethylbutanoate (200 mg, 1.377 mmol) and DIEA (0.481 mL, 2.75 mmol) in DCM (2 mL) solution was add 1-adamantyl fluoroformate (334 mg, 1.515 mmol). The reaction mixture was stirred at rt overnight. The compound was purified by silica gel column chromatography (20% EtOAc/80% hexane) to give a colorless oil (358 mg, 68%) as product.

$^1$H-NMR (CDCl$_3$-d) δ 0.94 (s, 9H), 1.62 (s, 6H), 2.07 (s, 6H), 2.13 (s, 3H), 3.70 (s, 3H), 4.07 (d, J=9 Hz, 1H), 5.09 (broad s, 1H, NH); LCMS RT=3.05 min, [M+H]$^+$=324.4.

Step 1b: Preparation of (S)-2-(Adamantan-1-yloxy-carbonylamino)-3,3-dimethyl-butyric acid

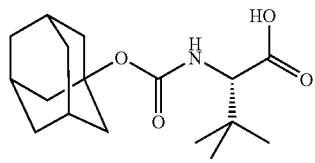

To a solution of (S)-2-(Adamantan-1-yloxycarbonylamino)-3,3-dimethyl-butyric acid methyl ester (358 mg, 1.107 mmol) in THF (4 mL) and MeOH (4 mL) was added a pre-made solution of lithium hydroxide monohydrate (93 mg, 2.214 mmol) in water (4.00 mL). The cloudy white solution was stirred at rt for 5 hrs. The volatiles were removed, and the reaction mixture was diluted with dilute citric acid solution and extracted with EtOAc (3×10 mL). The organic layer was washed with brine, dried over Na$_2$SO$_4$, filtered and evaporated to obtain a white solid (291.4 mg, 85%) as product. The crude material was used without further purification.

LCMS RT=2.91 min, [M+H]$^+$=310.4.

Step 2: Preparation of (2S,4R)-1-[(S)-2-(Adamantan-1-yloxycarbonylamino)-3,3-dimethyl-butyryl]-4-biphenyl-4-yl-4-methoxy-pyrrolidine-2-carboxylic acid methyl ester

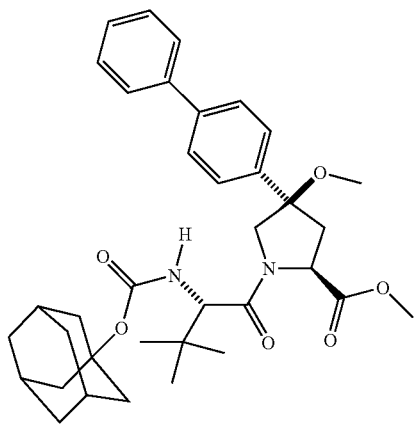

This material was prepared by the same procedure as described in Example 106 step 5, except using (S)-2-(Adamantan-1-yloxycarbonylamino)-3,3-dimethyl-butyric acid instead of (S)-2-(tert-butoxycarbonylamino)-3,3-dimethylbutanoic acid LCMS RT=3.63 min, [M+Na]$^+$=625.4.

Step 3: Preparation of (2S,4R)-1-[(S)-2-(Adamantan-1-yloxycarbonylamino)-3,3-dimethyl-butyryl]-4-biphenyl-4-yl-4-methoxy-pyrrolidine-2-carboxylic acid

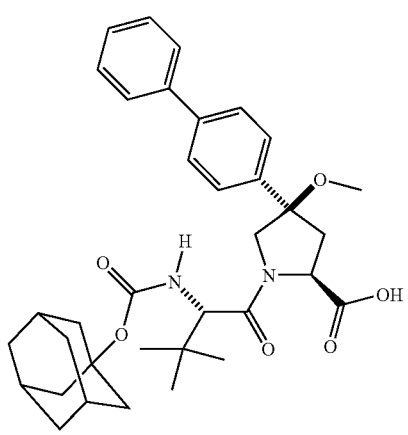

This material was prepared by the same procedure as described in Example 106 step 6 except using (2S,4R)-1-[(S)-2-(Adamantan-1-yloxycarbonylamino)-3,3-dimethyl-butyryl]-4-biphenyl-4-yl-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.16 min, [M+Na]$^+$=611.3.

Step 4: Preparation of {(S)-1-[(2S,4R)-4-Biphenyl-4-yl-2-((S)-(1R,2S)-1-cyclopropanesulfonylaminocarbonyl-2-vinyl-cyclopropylcarbamoyl)-4-methoxy-pyrrolidine-1-carbonyl]-2,2-dimethyl-propyl}-carbamic acid adamantan-1-yl ester Compound 204

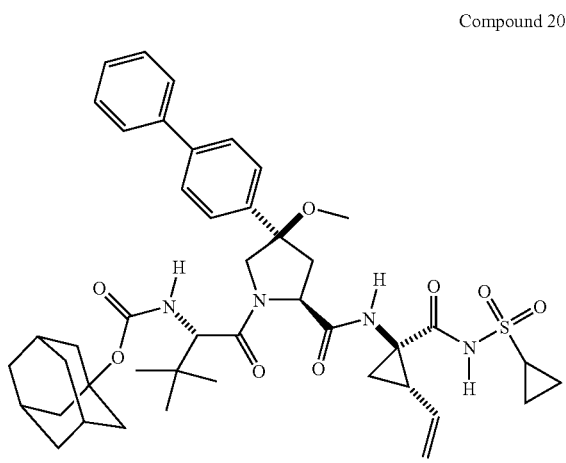

Compound 204 was prepared by the same procedure as described in Example 106 step 7 except using (2S,4R)-1-[(S)-2-(Adamantan-1-yloxycarbonylamino)-3,3-dimethyl-butyryl]-4-biphenyl-4-yl-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

$^1$H NMR (CD$_3$OD) δ 1.00-1.10 (m, 10H), 1.22-1.31 (m, 3H), 1.43 (m, 1H), 1.64-1.71 (m, 6H), 1.88 (m, 1H), 1.97-2.22 (m, 10H), 2.50 (m. 1H), 2.63 (m, 1H), 2.98 (m, 1H), 3.11 (s, 3H), 4.04 (d, J=9 Hz, 1H), 4.23 (m, 1H), 4.38 (m, 1H), 4.57 (m, 1H), 5.12 (d, J=12 Hz, 1H), 5.32 (d, J=18.5 Hz, 1H), 5.77 (m, 1H), 7.33-7.67 (m, 9H);

LCMS RT=3.43 min, [M+H]$^+$=801.4.

Example 205

Preparation of Compound 205

Compound 205

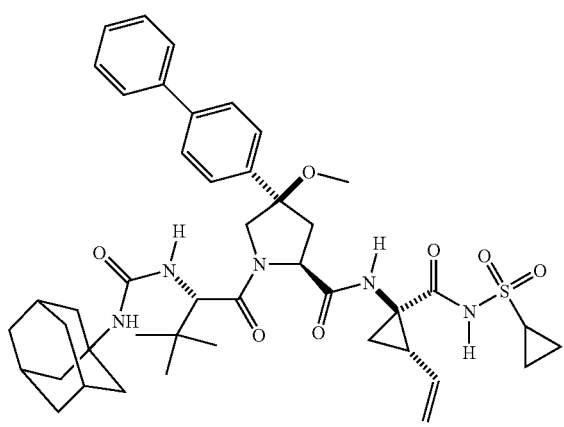

Step 1a: Preparation of (S)-2-(3-Adamantan-1-yl-ureido)-3,3-dimethyl-butyric acid methyl ester

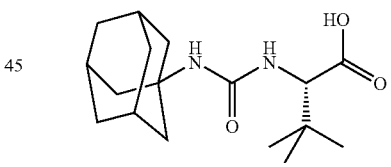

To a mixture of (S)-methyl 2-amino-3,3-dimethylbutanoate (200 mg, 1.377 mmol) and DIEA (0.481 mL, 2.75 mmol) in DCM (2 mL) solution was added 1-adamantyl isocyanate (334 mg, 1.515 mmol). The reaction mixture was stirred at rt overnight. The compound was purified by silica gel column chromatography (20% EtOAc/80% hexane) to give a white solid (265 mg, 59%) as product.

$^1$H-NMR (CDCl$_3$-d) δ 0.94 (s, 9H), 1.64 (s, 6H), 1.93 (s, 6H), 2.04 (s, 3H), 3.70 (s, 3H), 4.24 (d, J=9 Hz, 1H), 4.34 (broad s, 1H, NH), 4.88 (broad s, 1H, NH); LCMS RT=2.87 min, [M+H]$^+$=323.4.

Step 1b: Preparation of (S)-2-(3-Adamantan-1-yl-ureido)-3,3-dimethyl-butyric acid To a solution of (S)-2-(3-Adamantan-1-yl-ureido)-3,3-dimethyl-butyric acid methyl ester (265 mg, 0.822 mmol) in THF (4 mL) and MeOH (4 mL) was added a pre-made solution of lithium hydroxide monohydrate (69 mg, 1.644 mmol) in water (4.00 mL). The cloudy white solution was stirred at rt for 5 hrs. The volatiles were removed, and the reaction mixture was diluted with dilute citric acid solution and extracted with EtOAc (3×10 mL). The organic layer was washed with brine, dried over Na$_2$SO$_4$, filtered, evaporated to obtain white solid (232 mg, 92%) as product. The crude material was used without further purification.

LCMS RT=3.09 min, [M+H]$^+$=309.4.

Step 2: Preparation of (2S,4R)-1-[(S)-2-(3-Adamantan-1-yl-ureido)-3,3-dimethyl-butyryl]-4-biphenyl-4-yl-4-methoxy-pyrrolidine-2-carboxylic acid methyl ester

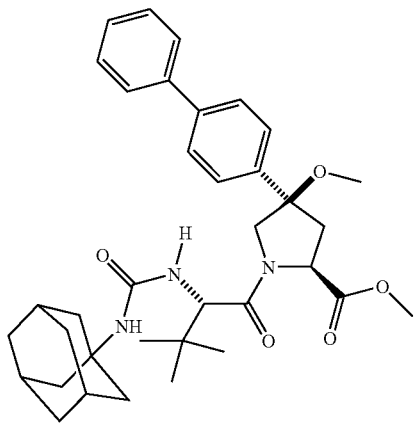

This material was prepared by the same procedure as described in Example 106 step 5, except using (S)-2-(3-Adamantan-1-yl-ureido)-3,3-dimethyl-butyric acid instead of (S)-2-(tert-butoxycarbonylamino)-3,3-dimethylbutanoic acid.

LCMS RT=3.51 min, [M+Na]$^+$=624.4.

Step 3: Preparation of (2S,4R)-1-[(S)-2-(3-Adamantan-1-yl-ureido)-3,3-dimethyl-butyryl]-4-biphenyl-4-yl-4-methoxy-pyrrolidine-2-carboxylic acid

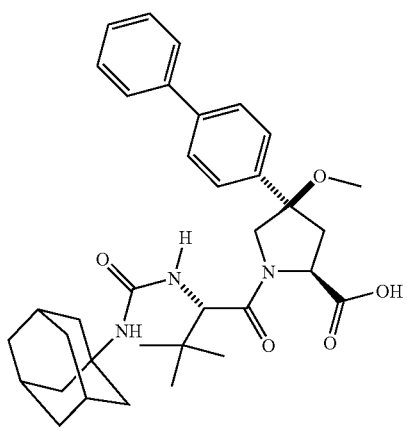

This material was prepared by the same procedure as described in Example 106 step 6 except using (2S,4R)-1-[(S)-2-(3-Adamantan-1-yl-ureido)-3,3-dimethyl-butyryl]-4-biphenyl-4-yl-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.42 min, [M+H]$^+$=588.3.

Step 4: Preparation of (2S,4R)-1-[(S)-2-(3-Adamantan-1-yl-ureido)-3,3-dimethyl-butyryl]-4-biphenyl-4-yl-4-methoxy-pyrrolidine-2-carboxylic acid ((1R, 2S)-1-cyclopropanesulfonylaminocarbonyl-2-vinyl-cyclopropyl)-amide Compound 205

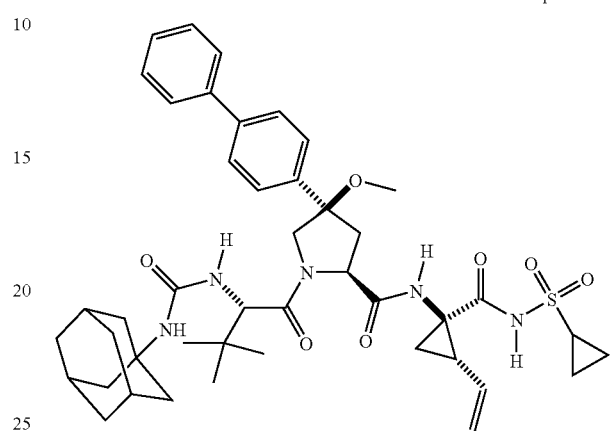

Compound 205 was prepared by the same procedure as described in Example 106 step 7 except using (2S,4R)-1-[(S)-2-(3-Adamantan-1-yl-ureido)-3,3-dimethyl-butyryl]-4-biphenyl-4-yl-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

$^1$H NMR (CD$_3$OD) δ 1.05-1.11 (m, 9H), 1.23-1.33 (m, 5H), 1.41 (m, 1H), 1.72 (s, 6H), 1.87 (m, 1H), 1.97-2.05 (m, 8H), 2.21 (m, 1H), 2.56 (m. 1H), 2.63 (m, 1H), 2.95 (m, 1H), 3.11 (s, 3H), 4.06 (d, J=9 Hz, 1H), 4.21 (m, 1H), 4.46 (m, 1H), 4.67 (m, 1H), 5.12 (d, J=12 Hz, 1H), 5.28 (d, J=18.5 Hz, 1H), 5.77 (m, 1H), 7.33-7.67 (m, 9H); LCMS RT=3.40 min, [M+Na]$^+$=800.5.

Example 206

Preparation of Compound 206

Compound 206

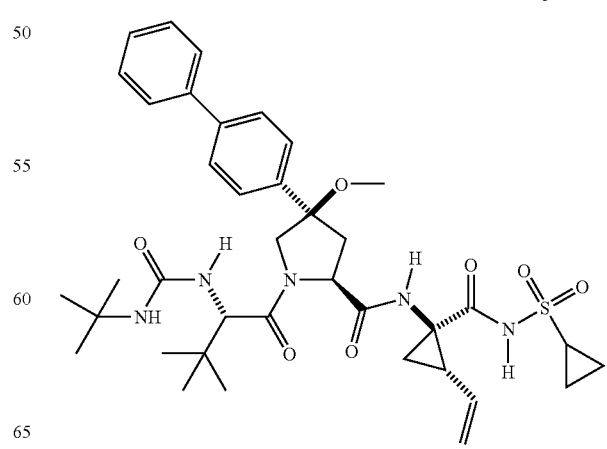

Step 1a: Preparation of (S)-2-(3-tert-Butyl-ureido)-3,3-dimethyl-butyric acid methyl ester

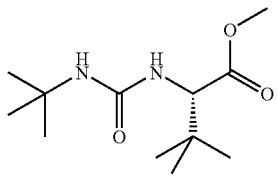

This material was prepared by the same procedure as described in Example 205 step 1a except using tert-butyl isocyanate instead of 1-adamantyl isocyanate.

LCMS RT=2.24 min, [M+H]$^+$=245.2.

Step 1b: Preparation of (S)-2-(3-tert-Butyl-ureido)-3,3-dimethyl-butyric acid

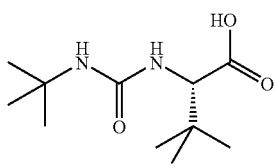

This material was prepared by the same procedure as described in Example 205 step 1b except using (S)-2-(3-tert-Butyl-ureido)-3,3-dimethyl-butyric acid methyl ester instead of (S)-2-(3-Adamantan-1-yl-ureido)-3,3-dimethyl-butyric acid methyl ester $^1$H-NMR (CDCl$_3$-d) C1.00 (s, 9H), 1.56 (s, 9H), 3.49 (s, 1H); LCMS RT=0.96 min, [M+H]$^+$=231.3.

Step 2: Preparation of (2S,4R)-4-Biphenyl-4-yl-1-[(S)-2-(3-tert-butyl-ureido)-3,3-dimethyl-butyryl]-4-methoxy-pyrrolidine-2-carboxylic acid methyl ester

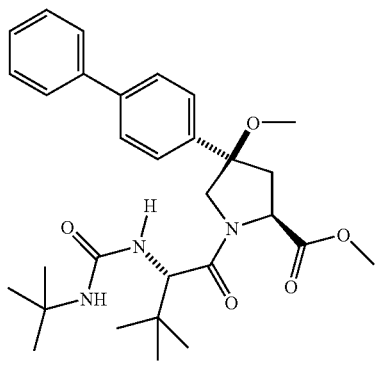

This material was prepared by the same procedure as described in Example 106, except using (S)-2-(3-tert-Butyl-ureido)-3,3-dimethyl-butyric acid as starting material in step 5.

LCMS RT=3.26 min, [M+Na]$^+$=546.3.

Step 2: Preparation of (2S,4R)-4-Biphenyl-4-yl-1-[(S)-2-(3-tert-butyl-ureido)-3,3-dimethyl-butyryl]-4-methoxy-pyrrolidine-2-carboxylic acid

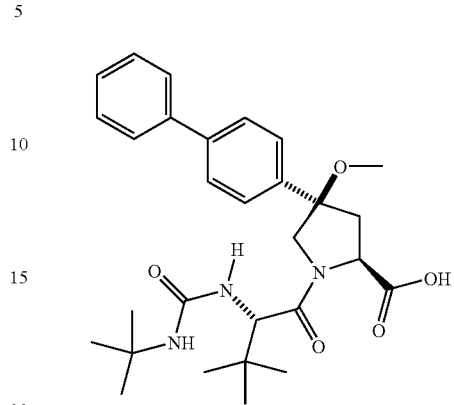

This material was prepared by the same procedure as described in Example 106 step 6 except using (2S,4R)-4-Biphenyl-4-yl-1-[(S)-2-(3-tert-butyl-ureido)-3,3-dimethyl-butyryl]-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.14 min, [M+Na]$^+$=532.3.

Step 3: Preparation of (2S,4R)-4-Biphenyl-4-yl-1-[(S)-2-(3-tert-butyl-ureido)-3,3-dimethyl-butyryl]-4-methoxy-pyrrolidine-2-carboxylic acid ((1R,2S)-1-cyclopropanesulfonylaminocarbonyl-2-vinyl-cyclopropyl)-amide Compound 206

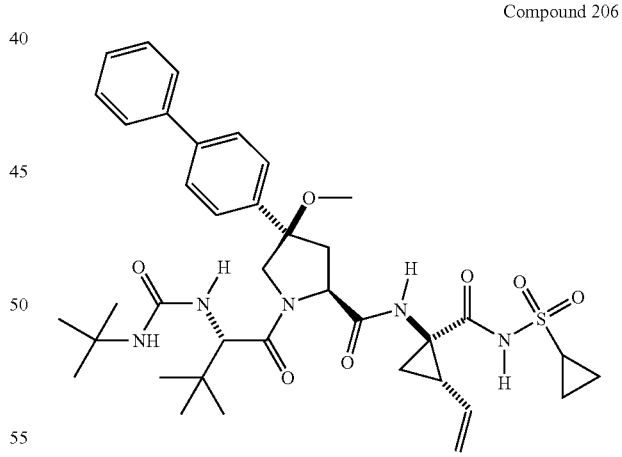

Compound 206 was prepared by the same procedure as described in Example 106 step 7 except using (2S,4R)-4-Biphenyl-4-yl-1-[(S)-2-(3-tert-butyl-ureido)-3,3-dimethyl-butyryl]-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid.

$^1$H NMR (CDCl$_3$-d) δ 1.03-1.08 (m, 12H), 1.23-1.38 (m, 11H), 1.75 (m, 1H), 1.92 (m, 1H), 2.08 (m. 1H), 2.47 (m, 1H), 2.96 (m, 1H), 3.11 (s, 3H), 4.10 (m, 1H), 4.49 (m, 1H), 4.53

(d, J=9 Hz, 1H), 4.80 (m, 1H), 5.11 (d, J=12 Hz, 1H), 5.28 (d, J=18.5 Hz, 1H), 5.74 (m, 1H), 7.57-7.61 (m, 4H), 7.40-7.46 (m, 5H); LCMS RT=3.26 min, [M+H]$^+$=722.4.

Example 207

Preparation of Compound 207 and Compound 208

Compound 207

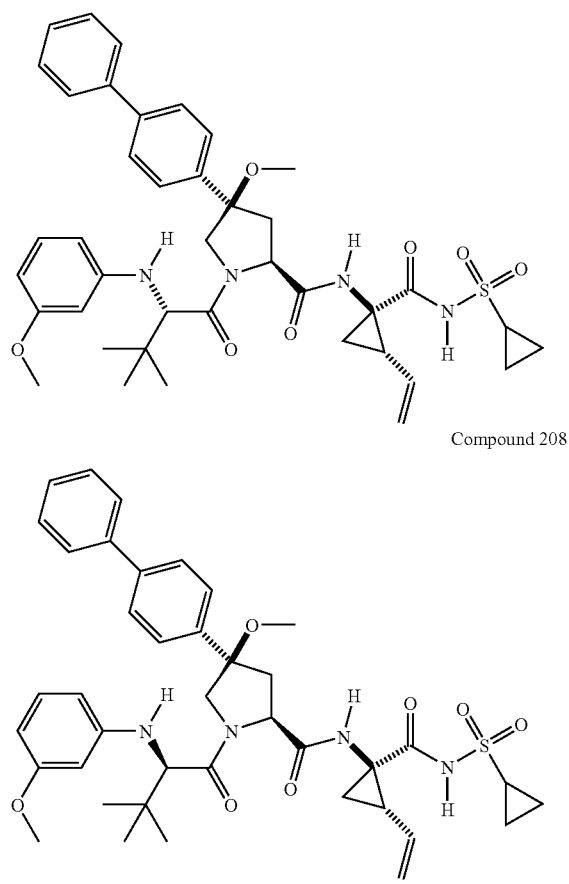

Compound 208

Step 1: Preparation of 2-(3-Methoxy-phenylamino)-3,3-dimethyl-butyric acid

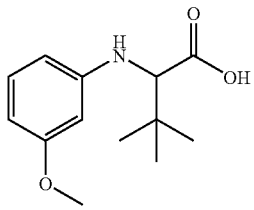

To a mixture of 3-methoxyaniline (100 mg, 0.812 mmol) and trimethylpyruvic acid (211 mg, 1.624 mmol) in methanol (3 mL) at rt was added acetic acid (0.930 mL, 16.24 mmol). The mixture was stirred for 30 min at rt then heated at 70° C. for 2 hrs. The mixture was cooled down to rt before adding sodium cyanotrihydroborate (1.624 mL, 1.624 mmol). The mixture was stirred overnight at rt. Water (10 mL) was added, and the mixture was extracted with ethyl acetate (3×10 mL). The organic layer was washed with sat. NaHCO$_3$ and brine solution, and then dried over Na$_2$SO$_4$, filtered, and evaporated to dryness. The residue was purified by preparative HPLC to get a white solid (30.5 mg, 16%) as product.

LCMS RT=3.46 min, [M+H]$^+$=238.2.

Step 2: Preparation of (2S,4R)-4-Biphenyl-4-yl-1-[(S)-2-(3-tert-butyl-ureido)-3,3-dimethyl-butyryl]-4-methoxy-pyrrolidine-2-carboxylic acid methyl ester

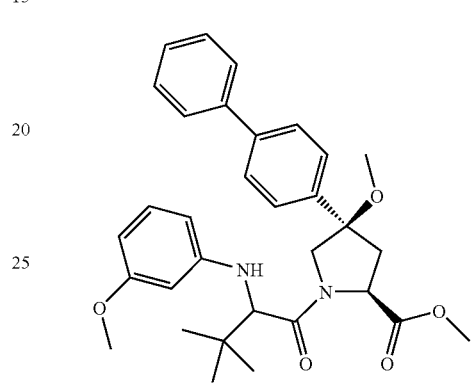

This material was prepared by the same procedure as described in Example 106 step 5 except using 2-(3-Methoxy-phenylamino)-3,3-dimethyl-butyric acid instead of (S)-2-(tert-butoxycarbonylamino)-3,3-dimethylbutanoic acid.

LCMS RT=3.31 min, [M+H]$^+$=531.5.

Step 2: Preparation of (2S,4R)-4-Biphenyl-4-yl-4-methoxy-1-[2-(3-methoxy-phenylamino)-3,3-dimethyl-butyryl]-pyrrolidine-2-carboxylic acid

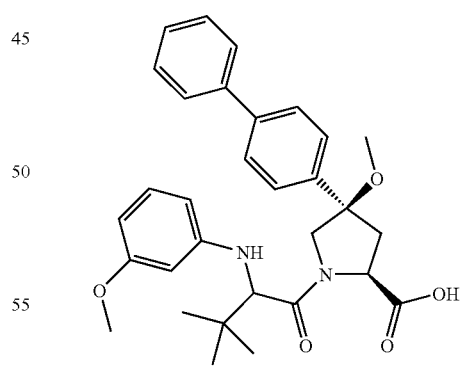

This material was prepared by the same procedure as described in Example 106 step 6 except using (2S,4R)-4-Biphenyl-4-yl-1-[(S)-2-(3-tert-butyl-ureido)-3,3-dimethyl-butyryl]-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.20 min, [M+H]$^+$=517.3.

Example 207

Preparation of Compound 207 and Compound 208

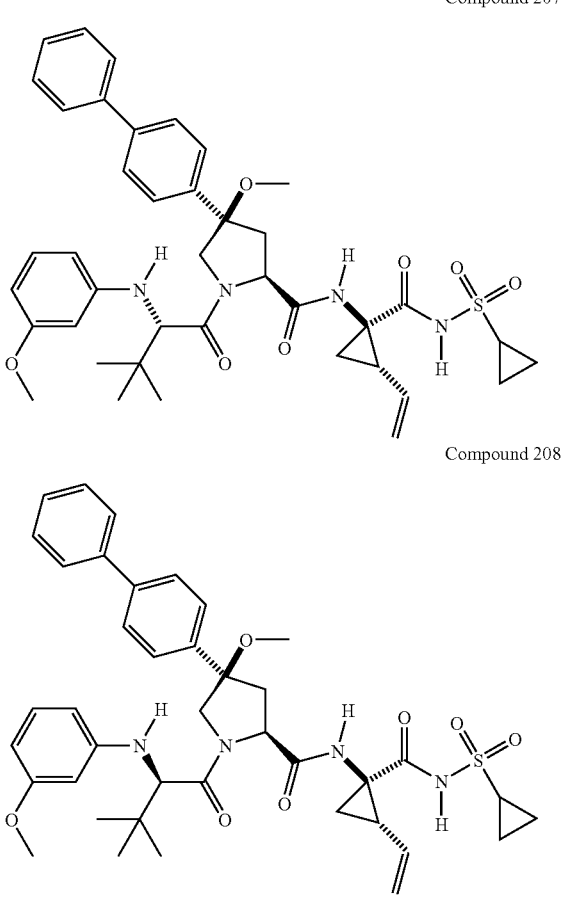

Compound 207

Compound 208

Compound 207 and Compound 208 were prepared by the same procedure as described in Example 106 step 7 except using (2S,4R)-4-Biphenyl-4-yl-4-methoxy-1-[2-(3-methoxy-phenylamino)-3,3-dimethyl-butyryl]-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid. The reaction mixture was separated by preparative HPLC to yield Compound 207 (2S,4R)-4-Biphenyl-4-yl-4-methoxy-1-[(S)-2-(3-methoxy-phenylamino)-3,3-dimethyl-butyryl]-pyrrolidine-2-carboxylic acid ((1R,2S)-1-cyclopropanesulfonylaminocarbonyl-2-vinyl-cyclopropyl)-amide and Compound 208 (2S,4R)-4-Biphenyl-4-yl-4-methoxy-1-[(R)-2-(3-methoxy-phenylamino)-3,3-dimethyl-butyryl]-pyrrolidine-2-carboxylic acid ((1R,2S)-1-cyclopropanesulfonylaminocarbonyl-2-vinyl-cyclopropyl)-amide Compound 207:

$^1$H NMR (CDCl$_3$-d) δ 1.00-1.10 (m, 2H), 1.14 (s, 9H), 1.31-1.43 (m, 3H), 1.92 (m, 1H), 2.03 (m, 1H), 2.44 (m, 1H), 2.91-2.98 (m, 2H), 3.00 (s, 3H), 3.69 (s, 3H), 3.75 (m, 1H), 3.95 (d, J=10 Hz, 1H), 4.36 (d, J=9 Hz, 1H), 4.57 (d, J=9 Hz, 1H), 5.15 (d, J=12 Hz, 1H), 5.28 (d, J=18.5 Hz, 1H), 5.72 (m, 1H), 6.17 (s, 1H), 6.21 (d, J=9.0 Hz, 1H), 6.25 (d, J=9.0 Hz, 1H), 7.00 (t, 1H), 7.34 (m, 3H), 7.45 (m, 2H), 7.58 (m, 4H); LCMS RT=3.29 min, [M+H]$^+$=729.4.

Compound 208:
$^1$H NMR (CDCl$_3$-d) δ 1.09 (s, 9H), 1.30 (m, 2H), 1.44 (m, 1H), 1.56 (m, 2H), 1.95 (m, 1H), 2.64 (m, 1H), 2.72 (m, 1H), 2.86 (m, 2H), 2.90 (s, 3H), 3.77 (m, 1H), 3.80 (s, 3H), 4.01 (d, J=10 Hz, 1H), 4.60 (d, J=9 Hz, 1H), 4.66 (d, J=9 Hz, 1H), 5.11 (d, J=12 Hz, 1H), 5.28 (d, J=18.5 Hz, 1H), 5.86 (m, 1H), 6.36 (s, 1H), 6.37 (d, J=9.0 Hz, 1H), 6.43 (d, J=9.0 Hz, 1H), 7.12 (t, 1H), 7.39 (t, 1H), 7.44-7.48 (m, 4H), 7.59 (d, J=9 Hz, 2H), 7.66 (d, J=9 Hz, 2H); LCMS RT=3.37 min, [M+H]$^+$=729.4

Example 208

Preparation of Compound 209 and Compound 210

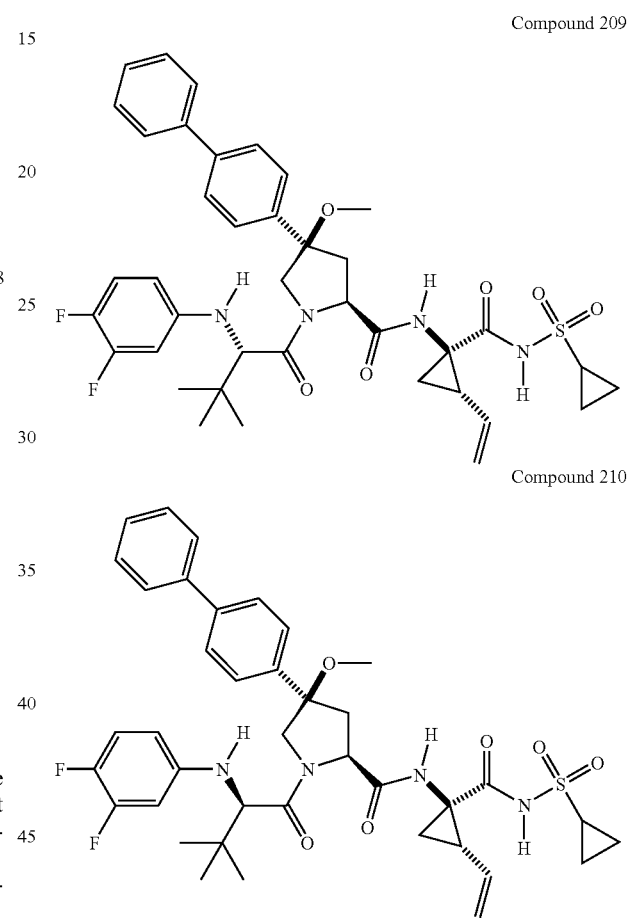

Compound 209

Compound 210

Step 1: Preparation of 2-(3,4-Difluoro-phenylamino)-3,3-dimethyl-butyric acid

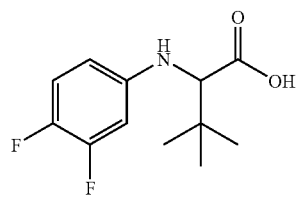

This material was prepared by the same procedure as described in Example 207 step 1 except using 3,4-difluoroaniline instead of 3-methoxyaniline.

LCMS RT=2.64 min, [M+H]$^+$=244.2.

139

Step 2: Preparation of (2S,4R)-4-Biphenyl-4-yl-1-[2-(3,4-difluoro-phenylamino)-3,3-dimethyl-butyryl]-4-methoxy-pyrrolidine-2-carboxylic acid methyl ester

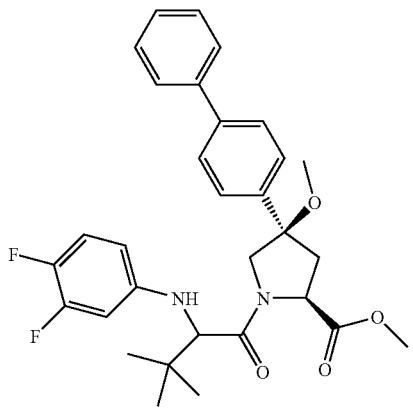

This material was prepared by the same procedure as described in Example 207 step 2 except using 2-(3,4-difluoro-phenylamino)-3,3-dimethyl-butyric acid instead of 2-(3-Methoxy-phenylamino)-3,3-dimethyl-butyric acid.

LCMS RT=3.37 min, [M+H]$^+$=537.5.

Step 2: Preparation of (2S,4R)-4-Biphenyl-4-yl-1-[2-(3,4-difluoro-phenylamino)-3,3-dimethyl-butyryl]-4-methoxy-pyrrolidine-2-carboxylic acid

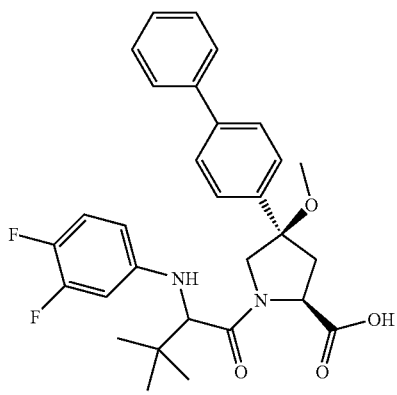

This material was prepared by the same procedure as described in Example 106 step 6 except using (2S,4R)-4-Biphenyl-4-yl-1-[2-(3,4-difluoro-phenylamino)-3,3-dimethyl-butyryl]-4-methoxy-pyrrolidine-2-carboxylic acid methyl ester instead of (2S,4R)-methyl 4-(biphenyl-4-yl)-1-((S)-2-(tert-butoxycarbonylamino)-3,3-dimethylbutanoyl)-4-methoxypyrrolidine-2-carboxylate.

LCMS RT=3.26 min, [M+H]$^+$=523.3.

140

Example 208

Preparation of Compound 209 and Compound 210

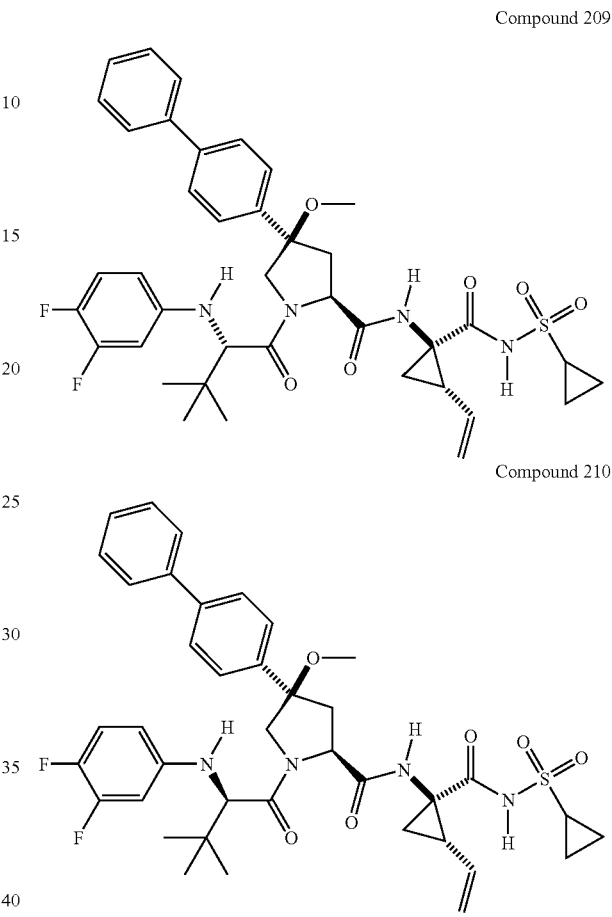

Compound 209 and Compound 210 were prepared by the same procedure as described in Example 106 step 7 except using (2S,4R)-4-Biphenyl-4-yl-1-[2-(3,4-difluoro-phenylamino)-3,3-dimethyl-butyryl]-4-methoxy-pyrrolidine-2-carboxylic acid instead of (2S,4R)-4-(biphenyl-4-yl)-1-((S)-2-(tert-butoxycarbonylamino)-3,3-dimethylbutanoyl)-4-methoxypyrrolidine-2-carboxylic acid. The reaction mixture was separated by preparative HPLC to yield Compound 209 (2S,4R)-4-Biphenyl-4-yl-1-[(S)-2-(3,4-difluoro-phenylamino)-3,3-dimethyl-butyryl]-4-methoxy-pyrrolidine-2-carboxylic acid ((1R,2 S)-1-cyclopropanesulfonylaminocarbonyl-2-vinyl-cyclopropyl)-amide and Compound 210 (2S,4R)-4-Biphenyl-4-yl-1-[(R)-2-(3,4-difluoro-phenylamino)-3,3-dimethyl-butyryl]-4-methoxy-pyrrolidine-2-carboxylic acid ((1R,2S)-1-cyclopropanesulfonylaminocarbonyl-2-vinyl-cyclopropyl)-amide Compound 209:

$^1$H NMR (CDCl$_3$-d) δ 1.00-1.10 (m, 2H), 1.14 (s, 9H), 1.31-1.43 (m, 3H), 1.92 (m, 1H), 2.03 (m, 1H), 2.44 (m, 1H), 2.91-2.98 (m, 2H), 3.00 (s, 3H), 3.71 (d, J=10 Hz, 1H), 3.80 (d, J=10 Hz, 1H), 4.36 (d, J=9 Hz, 1H), 4.57 (d, J=9 Hz, 1H), 5.15 (d, J=12 Hz, 1H), 5.28 (d, J=18.5 Hz, 1H), 5.74 (m, 1H), 6.26 (s, 1H), 6.41 (m, 1H), 6.86 (q, 1H), 7.26 (m, 1H), 7.29-7.39 (m, 2H), 7.45 (t, 2H), 7.58 (t, 4H); LCMS RT=3.05 min, [M+Na]+=757.3.

Compound 210:

$^1$H NMR (CDCl$_3$-d) δ 1.00-1.10 (m, 3H), 1.07 (s, 9H), 1.48 (m, 2H), 1.65 (m, 1H), 2.03 (m, 1H), 2.69 (m, 1H), 2.87 (m, 1H), 2.90 (s, 3H), 3.71 (d, J=10 Hz, 1H), 3.90 (d, J=10 Hz, 1H), 4.34 (d, J=9 Hz, 1H), 4.61 (d, J=9 Hz, 1H), 4.66 (d, J=9 Hz, 1H), 5.15 (d, J=12 Hz, 1H), 5.28 (d, J=18.5 Hz, 1H), 5.89 (m, 1H), 6.28 (s, 1H), 6.60 (m, 1H), 7.03 (q, 1H), 7.39 (t, 1H), 7.44-7.48 (m, 4H), 7.59 (d, J=9 Hz, 2H), 7.66 (d, J=9 Hz, 2H); LCMS RT=3.13 min, [M+H]$^+$=757.3.

Example 209

Preparation of Compound 211

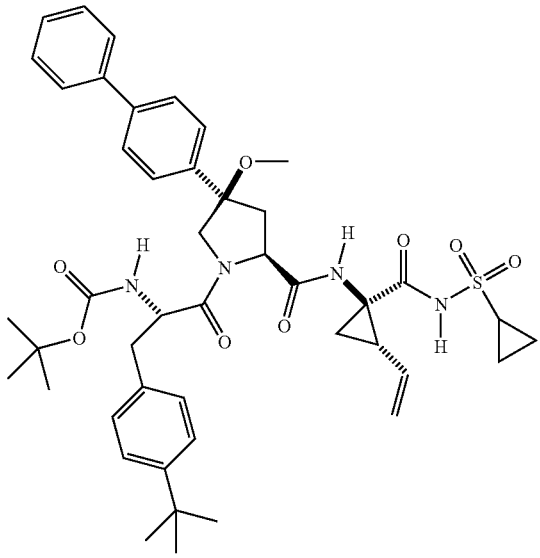

Compound 211

Biological Studies

HCV NS3/4A protease complex enzyme assays and cell-based HCV replicon assays were utilized in the present disclosure, and were prepared, conducted and validated as follows:

Generation of Recombinant HCV NS3/4a Protease Complex

HCV NS3 protease complexes, derived from the BMS strain, H77 strain or J4L6S strain, were generated, as described below. These purified recombinant proteins were generated for use in a homogeneous assay (see below) to provide an indication of how effective compounds of the present disclosure would be in inhibiting HCV NS3 proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR(RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493-1503 (1993)). The amino acid sequence of the nonstructural region, NS2-5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738-8743 (1997); AF054247, see Yanagi, M., St Claire, M., Shapiro, M., Emerson, S. U., Purcell, R. H. and Bukh, J, Virology 244 (1), 161-172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620-32, (1999)). Briefly, a three-lysine solubilizing tail was added at the 3'-end of the NS4A coding region. The cysteine in the P1 position of the NS4A-NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8):6758-69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)piperazine-N'-(2-Ethane Sulfonic acid) (HEPES), pH 7.5, 20% glycerol, 500 mM Sodium Chloride (NaCl), 0.5% Triton X-100, 1 microgram/milliliter ("μg/mL") lysozyme, 5 mM Magnesium Chloride (MgCl$_2$), 1 μg/ml DnaseI, 5 mM β-Mercaptoethanol (βME), Protease inhibitor-Ethylenediamine Tetraacetic acid (EDTA) free (Roche), homogenized and incubated for 20 minutes (min) at 4° C. The homogenate was sonicated and clarified by ultracentrifugation at 235000 g for 1 hour (h) at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton X-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS- PAGE and mass spectrometry analyses. The enzyme was stored at −80° C., thawed on ice and diluted prior to use in assay buffer.

FRET Peptide Assay to Monitor HCV NS3/4a Proteolytic Activity

The purpose of this in vitro assay was to measure the inhibition of HCV NS3 protease complexes, derived from the BMS strain, H77 strain or J4L6S strain, as described above, by compounds of the present disclosure. This assay provides an indication of how effective compounds of the present disclosure would be in inhibiting HCV NS3 proteolytic activity.

In order to monitor HCV NS3/4A protease activity, an NS3/4A peptide substrate was used. The substrate was RET S1 (Resonance Energy Transfer Depsipeptide Substrate; AnaSpec, Inc. cat #22991)(FRET peptide), described by Taliani et al. in Anal. Biochem. 240(2):60-67 (1996). The sequence of this peptide is loosely based on the NS4A/NS4B natural cleavage site for the HCV NS3 protease except there is an ester linkage rather than an amide bond at the cleavage site. The peptide also contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent.

The peptide substrate was incubated with one of the three recombinant NS3/4A protease complexes, in the absence or presence of a compound of the present disclosure. The inhibitory effects of a compound were determined by monitoring the formation of fluorescent reaction product in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol; 10 mM βME. Substrate: 2 µM final concentration (from a 2 mM stock solution in DMSO stored at −20° C.). HCV NS3/4A protease type 1a (1b), 2-3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 µM.

The assay was performed in a 96-well polystyrene black plate from Falcon. Each well contained 25 µl NS3/4A protease complex in assay buffer, 50 µl of a compound of the present disclosure in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100 - [(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel XLfit software using the equation, $y = A + ((B-A)/(1+((C/x)^D)))$.

All of the compounds tested were found to inhibit the activity of the NS3/4A protease complex with IC50's of 1.6 µM or less. Further, compounds of the present disclosure, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present disclosure in inhibiting HCV NS3/4A protease complex as compared to other serine or cysteine proteases.

The specificities of compounds of the present disclosure were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using a fluorometric Amino-Methyl-Coumarin (AMC) substrate specific for each enzyme was used as described previously (PCT Patent Application No. WO 00/09543) with some modifications to the serine protease assays. All enzymes were purchased from Sigma, EMDbiosciences while the substrates were from Bachem, Sigma and EMDbiosciences.

Compound concentrations varied from 100 to 0.4 µM depending on their potency. The enzyme assays were each initiated by addition of substrate to enzyme-inhibitor pre-incubated for 10 min at room temperature and hydrolysis to 15% conversion as measured on cytofluor.

The final conditions for each assay were as follows:

50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with 5 µM LLVY-AMC and 1 nM Chymotrypsin.

50 mM Tris-HCl, pH 8.0, 50 mM NaCl, 0.1 mM EDTA, 3% DMSO, 0.02% Tween-20, 5 µM succ-AAPV-AMC and 20 nM HNE or 8 nM PPE;

100 mM NaOAC (Sodium Acetate) pH 5.5, 3% DMSO, 1 mM TCEP (Tris(2-carboxyethyl)phosphine hydrochloride), 5 nM Cathepsin B (enzyme stock activated in buffer containing 20 mM TCEP before use), and 2 µM Z-FR-AMC diluted in $H_2O$.

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel XLfit software.

Generation of HCV Replicon

An HCV replicon whole cell system was established as described by Lohmann V, Korner F, Koch J, Herian U, Theilmann L, Bartenschlager R., Science 285(5424): 110-3 (1999). This system enabled us to evaluate the effects of our HCV Protease compounds on HCV RNA replication. Briefly, using the HCV strain 1b sequence described in the Lohmann paper (Assession number: AJ238799), an HCV cDNA was synthesized by Operon Technologies, Inc. (Alameda, Calif.), and the full-length replicon was then assembled in plasmid pGem9zf(+) (Promega, Madison, Wis.) using standard molecular biology techniques. The replicon consists of (i) the HCV 5' UTR fused to the first 12 amino acids of the capsid protein, (ii) the neomycin phosphotransferase gene (neo), (iii) the IRES from encephalomyocarditis virus (EMCV), and (iv) HCV NS3 to NS5B genes and the HCV 3' UTR. Plasmid DNAs were linearized with ScaI and RNA transcripts were synthesized in vitro using the T7 MegaScript transcription kit (Ambion, Austin, Tex.) according to manufacturer's directions. In vitro transcripts of the cDNA were transfected into the human hepatoma cell line, HUH-7. Selection for cells constitutively expressing the HCV replicon was achieved in the presence of the selectable marker, neomycin (G418). Resulting cell lines were characterized for positive and negative strand RNA production and protein production over time.

HCV Replicon FRET Assay

The HCV replicon FRET assay was developed to monitor the inhibitory effects of compounds described in the disclosure on HCV viral replication. HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin (Gibco-BRL), 1:100 L-glutamine and 5% DMSO in the dilution plate (0.5% DMSO final concentration in the assay). Compound/DMSO mixes were added to the cells and incubated for 4 days at 37° C. After 4 days, cells were first assessed for cytotoxicity using alamar Blue (Trek Diagnotstic Systems) for a $CC_{50}$ reading. The toxicity of compound ($CC_{50}$) was determined by adding $\frac{1}{10}^{th}$ volume of alamar Blue to the media incubating the cells. After 4 h, the fluorescence signal from each well was read, with an excitation wavelength at 530 nm and an emission wavelength of 580 nm, using the Cytofluor Series 4000 (Perspective Biosystems). Plates were then rinsed thoroughly with Phosphate-Buffered Saline (PBS) (3 times 150 µl). The cells were lysed with 25 µl of a lysis assay reagent containing an HCV protease substrate (5× cell Luciferase cell culture lysis reagent (Promega #E153A) diluted to 1× with distilled water, NaCl added to 150 mM final, the FRET peptide substrate (as described for the enzyme assay above) diluted to 10 µM final from a 2 mM stock in 100% DMSO. The plate was then placed into the Cytofluor 4000 instrument which had been set to 340 nm excitation/490 nm emission, automatic mode for 21 cycles and the plate read in a kinetic mode. $EC_{50}$ determinations were carried out as described for the $IC_{50}$ determinations.

HCV Replicon Luciferase Reporter Assay

As a secondary assay, $EC_{50}$ determinations from the replicon FRET assay were confirmed in a replicon luciferase reporter assay. Utilization of a replicon luciferase reporter assay was first described by Krieger et al (Krieger N, Lohmann V, and Bartenschlager R, J. Virol. 75(10):4614-4624 (2001)). The replicon construct described for our FRET assay was modified by inserting cDNA encoding a humanized form of the *Renilla luciferase* gene and a linker sequence fused directly to the 3'-end of the luciferase gene. This insert was introduced into the replicon construct using an Asc1 restriction site located in core, directly upstream of the neomycin marker gene. The adaptive mutation at position 1179 (serine to isoleucine) was also introduced (Blight K J, Kolykhalov, A A, Rice, C M, Science 290(5498):1972-1974). A stable cell line constitutively expressing this HCV replicon construct was generated as described above. The luciferase reporter assay was set up as described for the HCV replicon FRET assay with the following modifications. Following 4 days in a 37° C./5% $CO_2$ incubator, cells were analyzed for *Renilla Luciferase* activity using the Promega Dual-Glo Luciferase Assay System. Media (100 µl) was removed from each well containing cells. To the remaining 50 µl of media, 50 µl of Dual-Glo Luciferase Reagent was added, and plates rocked for 10 min to 2 h at room temperature. Dual-Glo Stop & Glo Reagent (50 µl) was then added to each well, and plates were rocked again for an additional 10 min to 2 h at room temperature. Plates were read on a Packard TopCount NXT using a luminescence program.

The percentage inhibition was calculated using the formula below:

$$\% \text{ control} = \frac{\text{average luciferase signal in experimental wells (+ compound)}}{\text{average luciferase signal in DMSO control wells (- compound)}}$$

The values were graphed and analyzed using XLfit to obtain the $EC_{50}$ value.

Representative compounds of the disclosure were assessed in the HCV enzyme assays, HCV replicon cell assay and/or in several of the outlined specificity assays. For example, Compound 3 was found to have an $IC_{50}$ of 4.4 nanomolar (nM) against the NS3/4A BMS strain in the enzyme assay. Similar potency values were obtained with the published H77 ($IC_{50}$ of 1.6 nM) and J4L6S ($IC_{50}$ of 1.1 nM) strains. The $EC_{50}$ value in the replicon FRET assay was 11 nM and 1.4 nM in the replicon Luciferase assay.

In the specificity assays, the same compound was found to have the following activity: HLE=82 µM; PPE>100 µM; Chymotrypsin=75 µM; Cathepsin B>100 µM. These results indicate this family of compounds is highly specific for the NS3 protease and many of these members inhibit HCV replicon replication.

The compounds of the current disclosure were tested and found to have activities in the ranges as follow:

$IC_{50}$ Activity Ranges (NS3/4A BMS Strain): A is 1 nM to 50 nM; B is >50 nM to 100 nM to 500 nM; C is >500 nM.

$EC_{50}$ Activity Range (for compounds tested): A is 1 nM to 50 nM; B is >50 nM to 100 nM to 500 nM; C is >500 nM.

Note that by using the Patent compound number shown in Table 2 the structures of compounds can be found herein.

TABLE 2

| Compound | HCV Protease (IC50) | HCV Pro Replicon (EC50) |
|---|---|---|
| Cmpd 106 | 1.00 | 11.00 |
| Cmpd 107 | B | C |
| Cmpd 108 | A | A |
| Cmpd 109 | A | B |
| Cmpd 110 | A | B |
| Cmpd 200 | A | A |
| Cmpd 201 | A | B |
| Cmpd 202 | A | B |
| Cmpd 203 | A | B |

TABLE 2-continued

| Compound | HCV Protease (IC50) | HCV Pro Replicon (EC50) |
| --- | --- | --- |
| Cmpd 204 | A | A |
| Cmpd 205 | A | A |
| Cmpd 206 | A | A |
| Cmpd 207 | A | A |
| Cmpd 208 | 315.00 | 1,303 |
| Cmpd 209 | A | A |
| Cmpd 210 | C | C |
| Cmpd 211 | 1600.00 | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

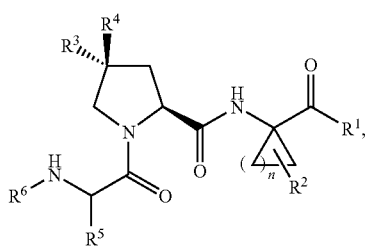

(I)

or a pharmaceutically acceptable salt thereof, wherein
n is 1, 2, or 3;
$R^1$ is selected from hydroxy and —NHSO$_2$R$^7$;
$R^2$ is selected from hydrogen, alkenyl, alkyl, cyanoalkyl, cycloalkyl, and haloalkyl;
$R^3$ is selected from alkenyl, alkyl, aryl, arylalkyl, cycloalkyl, (cycloalkyl)alkyl, heterocyclyl, and heterocyclylalkyl;
$R^4$ is —OR$^8$;
$R^5$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, hydroxyalkyl, (NR$^a$R$^b$)alkyl, and (NR$^a$R$^b$)carbonylalkyl;
$R^6$ is selected from alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, (NR$^a$R$^b$)carbonyl, and (NR$^a$R$^b$)sulfonyl; or
$R^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —NR$^g$R$^h$, (NR$^j$R$^k$)carbonyl, (NR$^j$R$^k$)sulfonyl, and oxo;
$R^7$ is selected from alkyl, aryl, cycloalkyl, (cycloalkyl)alkyl, heterocyclyl, and —NR$^c$R$^d$;
$R^8$ is selected from alkoxyalkyl, alkyl, alkylcarbonyl, arylalkyl, cycloalkyl, (cycloalkyl)alkyl, cycloalkylcarbonyl, haloalkoxyalkyl, haloalkyl, (NR$^e$R$^f$)carbonyl, and —P(O)(OR')$_2$; wherein R$^e$ and R$^f$ are independently selected from hydrogen, alkyl, and arylalkyl; or R$^e$ and R$^f$, together with the nitrogen atom to which they are attached, form a five or six-membered monocyclic heterocyclic ring optionally containing one additional heteroatom selected from O, NR$^x$, and S; wherein R$^x$ is selected from hydrogen and alkyl; and wherein R' is selected from hydrogen and alkyl;
$R^a$ and $R^b$ are independently selected from hydrogen, alkoxy, alkoxyalkyl, alkyl, aryl, arylalkyl, cycloalkyl, haloalkoxyalkyl, haloalkyl, heterocyclyl, and heterocyclylalkyl;
$R^c$ and $R^d$ are independently selected from alkoxy, alkyl, aryl, arylalkyl, cycloalkyl, (cycloalkyl)alkyl, heterocyclyl, and heterocyclylalkyl; or R$^c$ and R$^d$ together with the nitrogen atom to which they are attached form a five or six-membered monocyclic heterocyclic ring;
$R^g$ and $R^h$ are independently selected from hydrogen, alkoxyalkyl, alkoxycarbonyl, alkyl, alkylcarbonyl, arylalkyl, and haloalkyl; and
$R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

2. A compound of formula (II)

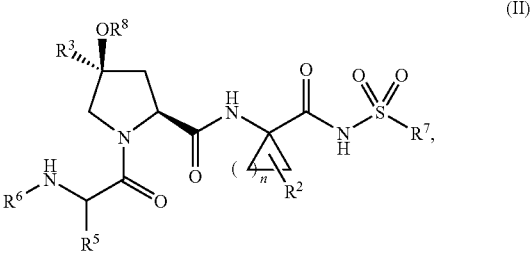

(II)

or a pharmaceutically acceptable salt thereof, wherein
n is 1, 2, or 3;
$R^2$ is selected from hydrogen, alkenyl, alkyl, cyanoalkyl, cycloalkyl, and haloalkyl;
$R^3$ is selected from alkenyl, alkyl, aryl, arylalkyl, cycloalkyl, (cycloalkyl)alkyl, heterocyclyl, and heterocyclylalkyl;
$R^5$ is selected from alkenyl, alkoxyalkyl, alkoxycarbonylalkyl, alkyl, arylalkyl, carboxyalkyl, cyanoalkyl, cycloalkyl, (cycloalkyl)alkyl, haloalkoxyalkyl, haloalkyl, hydroxyalkyl, (NR$^a$R$^b$)alkyl, and (NR$^a$R$^b$)carbonylalkyl;
$R^6$ is selected from alkoxycarbonyl, alkyl, alkylcarbonyl, alkylsulfonyl, cycloalkyloxycarbonyl, cycloalkyl, haloalkoxycarbonyl, haloalkyl, haloalkylcarbonyl, $(NR^aR^b)$carbonyl, and $(NR^aR^b)$sulfonyl; or $R^6$ is selected from phenyl and a five- or six-membered partially or fully unsaturated ring optionally containing one, two, three, or four heteroatoms selected from nitrogen, oxygen, and sulfur; wherein each of the rings is optionally substituted with one, two, three, or four substitutents independently selected from alkoxy, alkoxycarbonyl, alkyl, alkylcarbonyl, alkylsulfanyl, carboxy, cyano, cycloalkyl, cycloalkyloxy, halo, haloalkyl, haloalkoxy, —$NR^gR^h$, $(NR^jR^k)$carbonyl, $(NR^jR^k)$sulfonyl, and oxo;

$R^7$ is selected from alkyl, aryl, cycloalkyl, (cycloalkyl)alkyl, heterocyclyl, and —$NR^cR^d$;

$R^8$ is selected from alkoxyalkyl, alkyl, alkylcarbonyl, arylalkyl, cycloalkyl, (cycloalkyl)alkyl, cycloalkylcarbonyl, haloalkoxyalkyl, haloalkyl, $(NR^eR^f)$carbonyl, and —$P(O)(OR')_2$; wherein $R^e$ and $R^f$ are independently selected from hydrogen, alkyl, and arylalkyl; or $R^e$ and $R^f$, together with the nitrogen atom to which they are attached, form a five or six-membered monocyclic heterocyclic ring optionally containing one additional heteroatom selected from O, $NR^x$, and S; wherein $R^x$ is selected from hydrogen and alkyl; and wherein R' is selected from hydrogen and alkyl;

$R^a$ and $R^b$ are independently selected from hydrogen, alkoxy, alkoxyalkyl, alkyl, aryl, arylalkyl, cycloalkyl, haloalkoxyalkyl, haloalkyl, heterocyclyl, and heterocyclylalkyl;

$R^c$ and $R^d$ are independently selected from alkoxy, alkyl, aryl, arylalkyl, cycloalkyl, (cycloalkyl)alkyl, heterocyclyl, and heterocyclylalkyl; or $R^c$ and $R^d$ together with the nitrogen atom to which they are attached form a five or six-membered monocyclic heterocyclic ring;

$R^g$ and $R^h$ are independently selected from hydrogen, alkoxyalkyl, alkoxycarbonyl, alkyl, alkylcarbonyl, arylalkyl, and haloalkyl; and $R^j$ and $R^k$ are independently selected from hydrogen, alkyl, aryl, arylalkyl, and heterocyclyl; wherein the aryl, the aryl part of the arylalkyl, and the heterocyclyl are optionally substituted with one or two substituents independently selected from alkoxy, alkyl, and halo.

3. A compound of claim 2, or a pharmaceutically acceptable salt thereof, wherein n is 1;

$R^2$ is selected from alkenyl, alkyl, and haloalkyl;

$R^3$ is selected from alkenyl, alkyl, aryl, arylalkyl, cycloalkyl, (cycloalkyl)alkyl, heterocyclyl, and heterocyclylalkyl;

$R^5$ is selected from alkenyl, alkyl, and arylalkyl;

$R^6$ is selected from alkoxycarbonyl, cycloalkyloxycarbonyl, haloalkoxycarbonyl, $(NR^aR^b)$carbonyl; or $R^6$ is phenyl optionally substituted with one or two substitutents independently selected from alkoxy and halo; and $R^7$ is cycloalkyl.

4. A compound of claim 3, or a pharmaceutically acceptable salt thereof, wherein $R^3$ is selected from aryl and heterocyclyl.

5. A compound of claim 4, or a pharmaceutically acceptable salt thereof, wherein $R^3$ is aryl.

6. A compound selected from

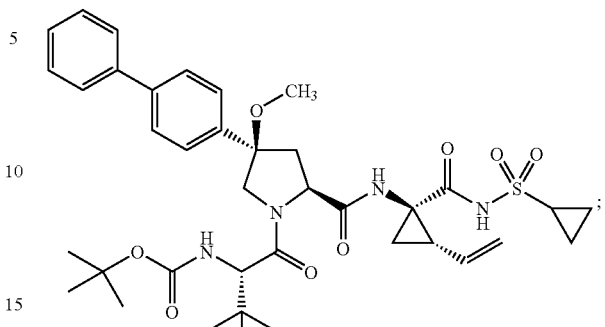

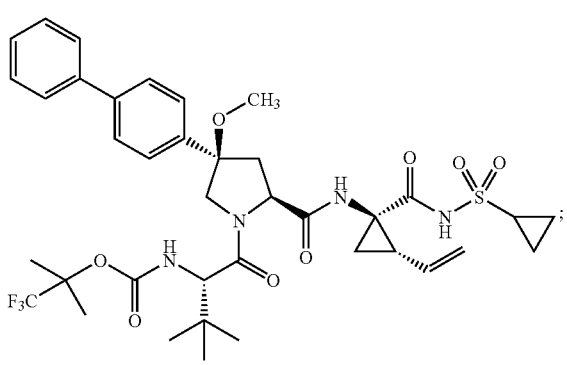

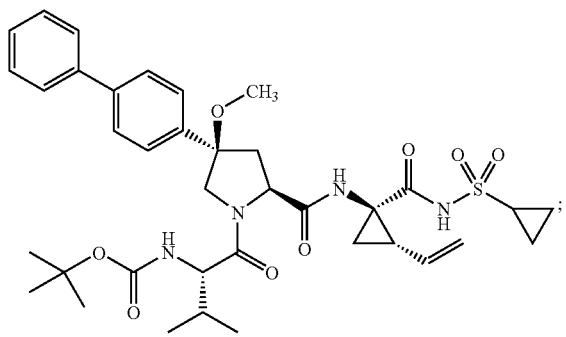

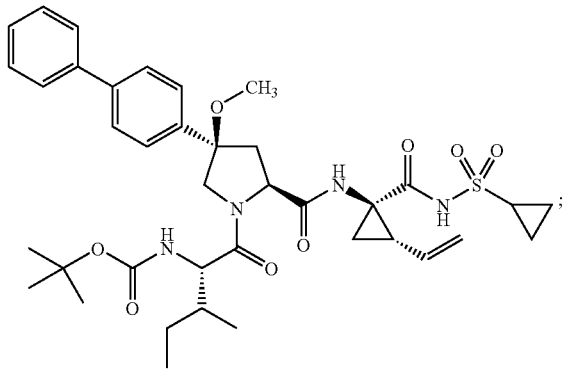

151
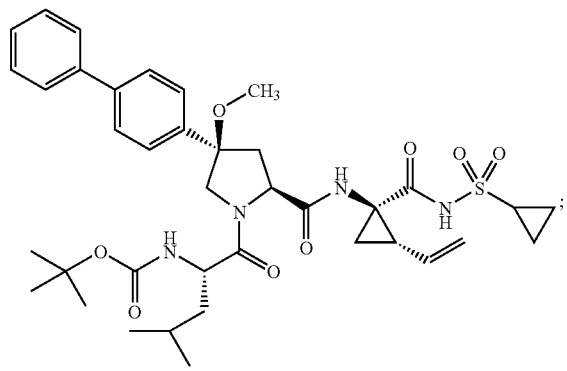
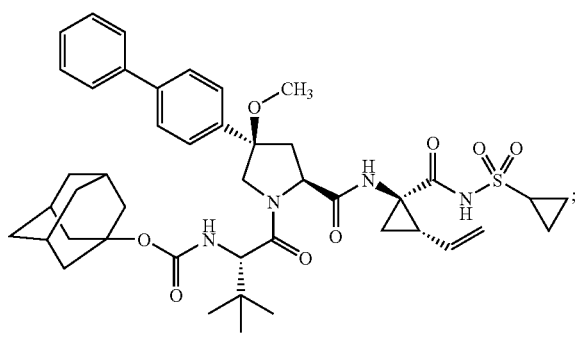
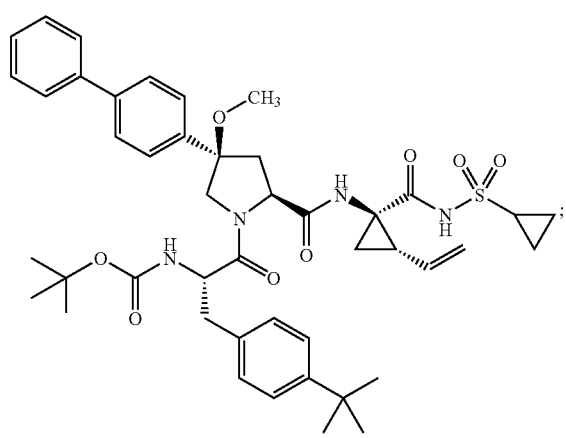
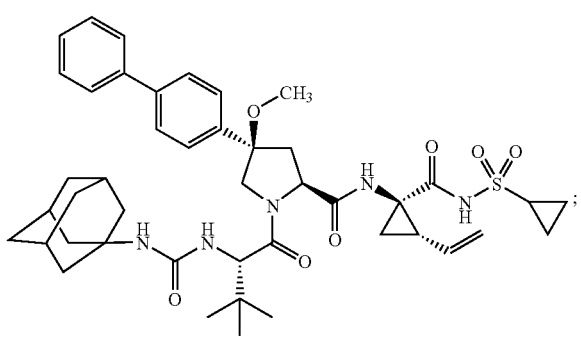
152
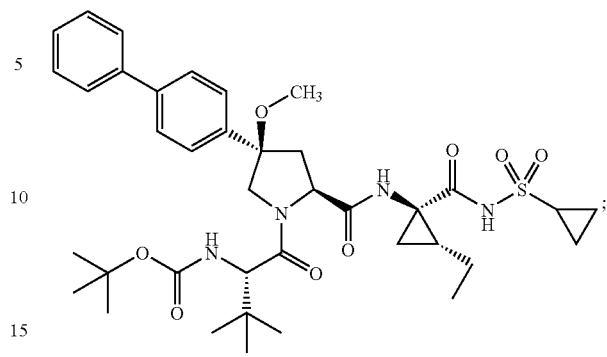
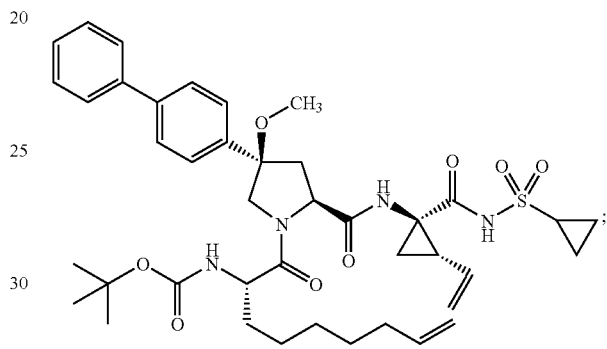
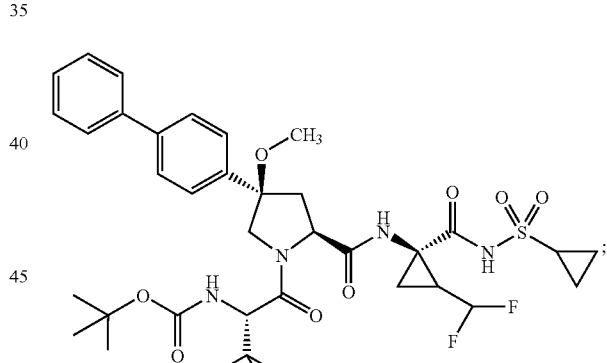
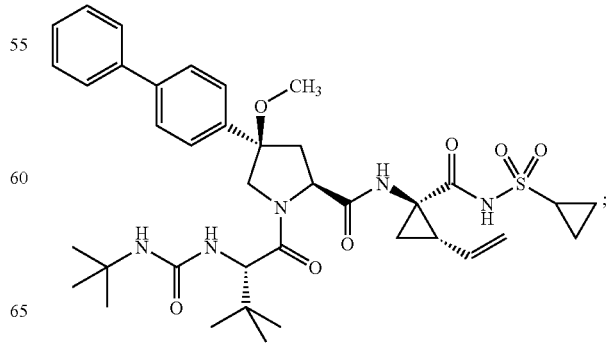

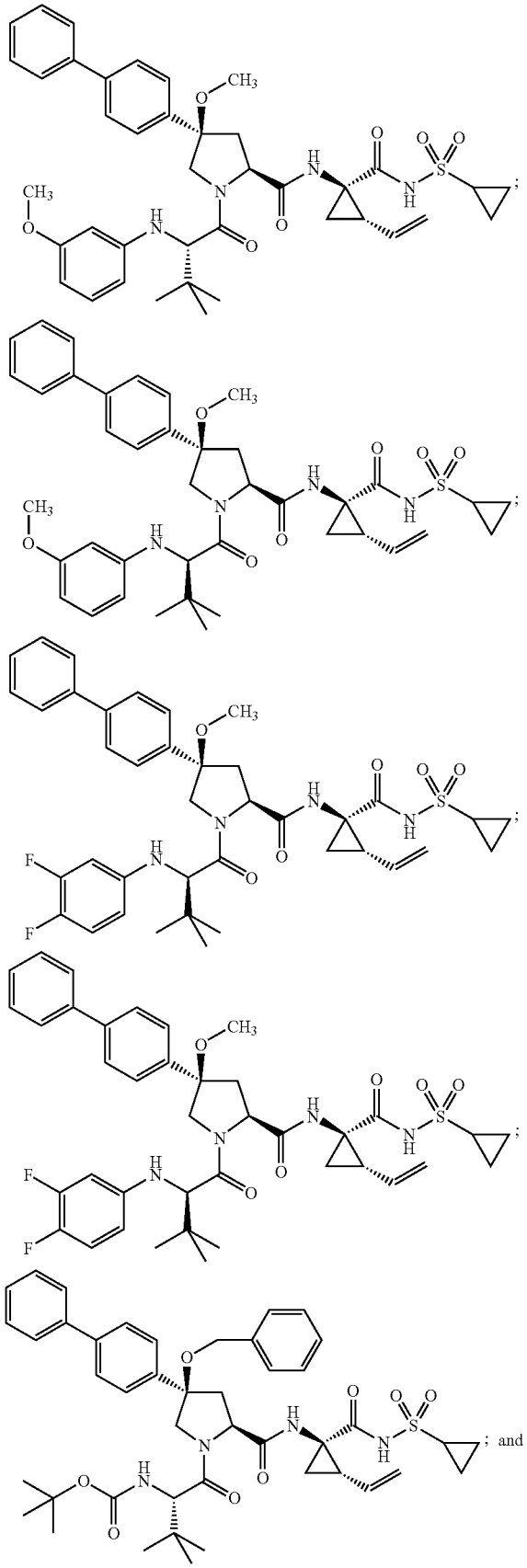

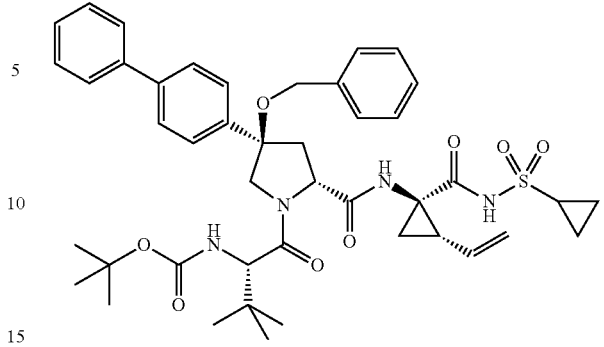

or a pharmaceutically acceptable salt thereof.

7. A composition comprising the compound of claim 1, or a pharmaceutically acceptable salt thereof, and a pharmaceutically acceptable carrier.

8. The composition of claim 7 further comprising at least one additional compound having anti-HCV activity.

9. The composition of claim 8 wherein at least one of the additional compounds is an interferon or a ribavirin.

10. The composition of claim 9 wherein the interferon is selected from interferon alpha 2B, pegylated interferon alpha, consensus interferon, interferon alpha 2A, and lymphoblastiod interferon tau.

11. The composition of claim 8 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5′-monophospate dehydrogenase inhibitor, amantadine, and rimantadine.

12. The composition of claim 8 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

13. A method of treating an HCV infection in a patient, comprising administering to the patient a therapeutically effective amount of a compound of claim 1, or a pharmaceutically acceptable salt thereof.

14. The method of claim 13 further comprising administering at least one additional compounds having anti-HCV activity prior to, after, or simultaneously with the compound of claim 1, or a pharmaceutically acceptable salt thereof.

15. The method of claim 14 wherein at least one of the additional compounds is an interferon or a ribavirin.

16. The method of claim 15 wherein the interferon is selected from interferon alpha 2B, pegylated interferon alpha, consensus interferon, interferon alpha 2A, and lymphoblastiod interferon tau.

17. The method of claim 14 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5′-monophospate dehydrogenase inhibitor, amantadine, and rimantadine.

18. The method of claim 14 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

| | | |
|---|---|---|
| PATENT NO. | : 7,888,464 B2 | Page 1 of 1 |
| APPLICATION NO. | : 11/939780 | |
| DATED | : February 15, 2011 | |
| INVENTOR(S) | : Alan Xiangdong Wang et al. | |

It is certified that error appears in the above-identified patent and that said Letters Patent is hereby corrected as shown below:

In the Specification:

Column 5, line 2, change "lymphoblastiod" to -- lymphoblastoid --.

Column 5, line 11, change "Imiqimod" to -- Imiquimod --.

Column 5, line 12, change "5'-monophospate" to -- 5'-monophosphate --.

Column 5, line 39, change "lymphoblastiod" to -- lymphoblastoid --.

Column 5, line 51, change "Imiqimod" to -- Imiquimod --.

Column 5, line 52, change "5'-monophospate" to -- 5'-monophosphate --.

In the Claims:

Claim 10:

Column 154, lines 26 and 27, change "lymphoblastiod" to -- lymphoblastoid --.

Claim 11:

Column 154, line 32, change "Imiqimod" to -- Imiquimod --.

Column 154, lines 32 and 33, change "5'-monophospate" to -- 5'-monophosphate --.

Claim 16:

Column 154, lines 52 and 53, change "lymphoblastiod" to -- lymphoblastoid --.

Claim 17:

Column 154, lines 56 and 57, after "response", delete "interfering RNA, anti-sense RNA,".

Column 154, line 57, change "Imiqimod" to -- Imiquimod --.

Column 154, lines 57 and 58, change "5'-monophospate" to -- 5'-monophosphate --.

Signed and Sealed this
Sixth Day of December, 2011

David J. Kappos
*Director of the United States Patent and Trademark Office*